US012560591B2

(12) United States Patent
Young et al.

(10) Patent No.: US 12,560,591 B2
(45) Date of Patent: Feb. 24, 2026

(54) METHODS OF TREATMENT WITH CD8 T CELL-MEDIATED IMMUNE THERAPY

(71) Applicant: Providence Health & Services—Oregon, Portland, OR (US)

(72) Inventors: Kristina Young, Portland, OR (US); Andrew Gunderson, Portland, OR (US)

(73) Assignee: Providence Health & Services—Oregon, Portland, OR (US)

( * ) Notice: Subject to any disclaimer, the term of this patent is extended or adjusted under 35 U.S.C. 154(b) by 1021 days.

(21) Appl. No.: 17/642,549

(22) PCT Filed: Sep. 11, 2020

(86) PCT No.: PCT/US2020/050487
§ 371 (c)(1),
(2) Date: Mar. 11, 2022

(87) PCT Pub. No.: WO2021/050936
PCT Pub. Date: Mar. 18, 2021

(65) Prior Publication Data

US 2022/0390433 A1 Dec. 8, 2022

Related U.S. Application Data

(60) Provisional application No. 62/899,630, filed on Sep. 12, 2019.

(51) Int. Cl.

| | |
|---|---|
| ***G01N 33/50*** | (2006.01) |
| ***A61K 40/11*** | (2025.01) |
| ***A61K 40/42*** | (2025.01) |

(52) U.S. Cl.
CPC .......... *G01N 33/5011* (2013.01); *A61K 40/11* (2025.01); *A61K 40/42* (2025.01); *G01N 33/505* (2013.01); *A61K 2239/50* (2023.05)

(58) Field of Classification Search
CPC .. G01N 33/5011; G01N 33/505; A61K 40/11; A61P 35/00
See application file for complete search history.

(56) References Cited

U.S. PATENT DOCUMENTS

| | | | |
|---|---|---|---|
| 2014/0255341 | A1 | 9/2014 | Kalinski et al. |
| 2016/0166685 | A1 | 6/2016 | Cheung et al. |
| 2018/0195133 | A1 | 7/2018 | Huseni |
| 2020/0216551 | A1 | 7/2020 | Li et al. |

OTHER PUBLICATIONS

Allison et al, (Heterogeneity and Cancer, retrieved from: https://www.cancernetwork.com/view/heterogeneity-and-cancer (2014); at paragraph 1 of the Introduction (Year: 2014).*

Ravindran et al (Tumor-promoting role of TGFβ1 signaling in ultraviolet B-induced skin carcinogenesis is associated with cutaneous inflammation and lymph node migration of dermal dendritic cells. Carcinogenesis. Apr. 2014;35(4):959-66. doi: 10.1093/carcin/bgt486. Epub Dec. 20, 2013) (Year: 2013).*

Groom et al (CXCR3 in T cell function. Exp Cell Res. Mar. 10, 2011;317(5):620-31. doi: 10.1016/j.yexcr.2010.12.017. PMID: 21376175; PMCID: PMC3065205) (Year: 2011).*

Gunderson et al (TGFβR1 Antagonism Improves Radiation Efficacy by Relieveing CXCR3 Suppression and Enhancing Tumor Recruitment of CD8+ T Cells, obtained from: https://doi.org/10.1016/j.ijrobp.2019.06.558, pub Sep. 14, 2019) (Year: 2019).*

Young et al (inhibition prior to hypofractionated radiation enhances efficacy in preclinical models. Cancer Immunol Res. Oct. 2014;2(10):1011-22. doi: 10.1158/2326-6066.CIR-13-0207. Epub Jul. 21, 2014) (Year: 2014).*

Young et al (TGFβ inhibition improves the efficacy of radiation therapy. Oncoimmunology. Sep. 14, 2014;4(3):e955696. doi: 10.4161/21624011.2014.955696) [hereinafter referred to as K Young et al] (Year: 2014).*

Abron et al (Differential role of CXCR3 in inflammation and colorectal cancer. Oncotarget. 2018; 9: 17928-17936. Retrieved from https://www.oncotarget.com/article/24730/text/) (Year: 2018).*

Gunderson et al 2020 (TGFβ suppresses CD8+ T cell expression of CXCR3 and tumor trafficking. Nat Commun. Apr. 9, 2020;11(1): 1749. doi: 10.1038/s41467-020-15404-8) (Year: 2020).*

Takaku et al (Blockade of TGF-beta enhances tumor vaccine efficacy mediated by CD8(+) T cells. Int J Cancer. Apr. 1, 2010;126(7): 1666-74. doi: 10.1002/ijc.24961.) (Year: 2010).*

Kuo et al (he Role of CXCR3 and Its Chemokine Ligands in Skin Disease and Cancer. Front Med (Lausanne). Sep. 25, 2018;5:271. doi: 10.3389/fmed.2018.00271) (Year: 2018).*

Elhalawani et al., "Initial report of imaging correlates for the tumor microenvironment in a Phase II study of TGFβRI inhibition with chemoradiation in locally advanced rectal adenocarcinoma," Poster, *ASTRO-SITC-NCI Immunotherapy Workshop,* Bethesda, Maryland, Jun. 15-16, 2017 (1 page).

Han et al., "Role of CXCR3 Signaling in Response to Anti-PD-1 Therapy," *eBioMedicine,* vol. 48, pp. 169-177, 2019.

NCT02688712, "ExIST Study of LY2157299 (Galunisertib) in Rectal Cancer," available at https://clinicaltrials.gov/ct2/show/NCT02688712, retrieved on Jun. 26, 2019 (9 pages).

* cited by examiner

*Primary Examiner* — Gregory S Emch
*Assistant Examiner* — Ashley H. Gao
(74) *Attorney, Agent, or Firm* — Klarquist Sparkman, LLP

(57) ABSTRACT

Methods of treating a subject with cancer with CD8 T cell-mediated immune therapy are provided. The methods include measuring an amount of CXCR3-positive T cells in a peripheral blood sample or a tumor sample from a subject with cancer following treatment of the subject with at least one dose of the CD8 T cell-mediated therapy and comparing the amount of CXCR3-positive T cells in the sample to a control. Responsiveness of the cancer to the CD8 T cell-mediated therapy is predicted based on whether there is an increase or decrease in the amount of CXCR3-positive T cells in the sample. Methods further including treating the subject with at least one additional dose of the CD8 T cell-mediated immune therapy are also provided.

21 Claims, 40 Drawing Sheets

Specification includes a Sequence Listing.

Non-transgenic allele: 150 bp
Floxed allele: 300 bp
Cre excised allele: 400 bp

CT26 s.c.
BALB/C d7-13
LY3200882 d14-d19
RT 5Gyx5
+ 5-FU
~25 mm² tumors

CT26
cured d75
CT26
and 4T1
rechallenge

*tumor growth* of tumors rejected

CT26   6/6

4T1   0/6 tumor size (mm²)

days

*isolate naive CD8⁺ T cells*

C57BL/6 SJL *CD45.1⁺*     ALK5^ΔCD8 *CD45.2⁺*

*CFSE label*

*Adoptive co-transfer* d14     MC38 d21 *harvest tumor LN, and spleen for FACS*

METHODS OF TREATMENT WITH CD8 T CELL-MEDIATED IMMUNE THERAPY

CROSS REFERENCE TO RELATED APPLICATION

This is the § 371 U.S. National Stage of International Application No. PCT/US2020/050487, filed Sep. 11, 2020, which was published in English under PCT Article 21(2), which in turn claims the benefit of U.S. Provisional Application No. 62/899,630, filed Sep. 12, 2019, which is incorporated herein in its entirety.

FIELD

This disclosure relates to methods for treating a subject with CD8 T cell-mediated immune therapy, particularly a subject with cancer.

BACKGROUND

The most broadly successful cancer immunotherapy to date is immune-checkpoint blockade (ICB). While responses to ICB have challenged cancer care paradigms, only a small subset of patients have durable, complete responses to these treatments. Within immunogenic tumor types (e.g., melanoma and renal cell carcinoma), about 50% of patients will respond to ICB (Hodi et al., *Proc.* $107^{th}$ Ann. Meet. *Am. Assoc. Cancer Res*. CT001, 2016; Robert et al., *N. Engl. J. Med.* 327:320-330, 2015), but within less immunogenic tumor types, response rates are closer to 5% (e.g., pancreatic cancer; Yarchoan et al., *N. Engl. J. Med.* 377:2500-2501, 2017). One notable exception are patients whose tumors have a mismatch repair (MMR) deficiency, where response rates to ICB are greater than 50%, independent of cancer type (Le et al., *Science* 357:409-413, 2017). Consistent with these data, response to ICB in colorectal cancer is dichotomous with MMR intact tumors exhibiting response rates less than 5% (Yarchoan et al., *N. Engl. J. Med.* 377:2500-2501, 2017). For patients with locally advanced rectal adenocarcinoma, immune therapy is not yet a part of curative intent treatment. For these patients, mesorectal excision, along with chemotherapy and radiation are still the backbone of treatment. Despite increased understanding of the mechanisms of therapeutic cell death and tumor cell resistance to cytotoxic therapy in the preclinical setting, successful combination of immunotherapy with chemo- and/or radiation therapy have been slower to gain clinical traction (Antonia et al., *N. Engl. J. Med.* 377:1919-1929, 2017; Ngwa et al., *Nature Rev. Cancer* 18:2018).

SUMMARY

There remains a need to improve responses to cancer therapies, including identifying subjects likely to successfully respond to treatment strategies and developing treatment regimens to improve response rate.

Disclosed herein are methods of treating a subject with cancer with CD8 T cell-mediated immune therapy. In particular embodiments, the methods include assessing or predicting response of a cancer in a subject to treatment with a CD8 T cell-mediated immune therapy. Exemplary CD8 T cell-mediated immune therapies include inhibition of TGFβR1 signaling, immune checkpoint blockade, adoptive T cell transfer therapies, and chimeric antigen receptor (CAR)-T cell therapies.

In some embodiments, the methods include measuring an amount of CXCR3-positive T cells in a peripheral blood sample (e.g. whole blood, plasma, or serum) from a subject following treatment of the subject with at least one dose of a CD8 T cell-mediated immune therapy, comparing the amount of CXCR3-positive T cells in the peripheral blood sample to a control, and predicting that the cancer will respond (e.g., has an increased likelihood of response) to the CD8 T cell-mediated immune therapy if the amount of CXCR3-positive T cells in the peripheral blood sample is decreased compared to the control or that the cancer will not respond (e.g., has a decreased likelihood of response) to the CD8 T cell-mediated immune therapy if the amount of CXCR3-positive T cells in the peripheral blood sample is unchanged or increased compared to the control. In some examples, the control is an amount of CXCR3-positive T cells in a peripheral blood sample from the subject prior to treatment with the CD8 T cell-mediated immune therapy.

In other embodiments, the methods include measuring an amount of CXCR3-positive T cells in a tumor sample from the subject following treatment of a subject with at least one dose of a CD8 T cell-mediated immune therapy, comparing the amount of CXCR3-positive T cells in the tumor sample to a control, and predicting that the cancer will respond (e.g., has increased likelihood of response) to the CD8 T cell-mediated immune therapy if the amount of CXCR3-positive T cells is increased in the tumor sample compared to the control or that the cancer will not respond (e.g., has decreased likelihood of response) to the CD8 T cell-mediated immune therapy if the amount of CXCR3-positive T cells in the tumor sample is unchanged or increased compared to the control. In some examples, the control is an amount of CXCR3-positive T cells in a tumor sample from the subject prior to treatment with the CD8 T cell-mediated immune therapy.

In some non-limiting examples, the CD8 T cell-mediated immune therapy is a TGFβR1 inhibitor, such as galunisertib (LY2157299) or LY320088230. In other non-limiting examples, the CD8 T cell-mediated immune therapy is an immune checkpoint inhibitor (such as an anti-CTLA-4 antibody, an anti-PD-L1 antibody, or an anti-PD-1 antibody). In particular examples, the subject is administered 1-14 doses (such as 1, 2, 3, 4, 5, 6, 7, 8, 9, 10, 11, 12, 13, or 14 daily doses) of therapy. The subject may also be administered a chemotherapy, surgery, and/or radiation therapy following or concurrently with the inhibitor of TGFβR1 signaling.

In some embodiments, the methods, also selecting a subject with a decreased amount of CXCR3-positive T cells in the peripheral blood sample compared to the control or selecting a subject with an increased amount of CXCR3-positive T cells in the tumor sample compared to the control. In some examples, the methods include administering at least one additional dose of the CD8 T cell-mediated immune therapy (such as the inhibitor of TGFβR1 signaling or the immune checkpoint inhibitor) to the subject if the cancer is predicted to respond to the therapy, such a subject with a decreased amount of CXCR3-positive T cells in the peripheral blood sample compared to the control or a subject with an increased amount of CXCR3-positive T cells in the tumor sample compared to the control. In other examples, the methods include discontinuing treatment with the CD8 T cell-mediated immune therapy (such as the inhibitor of TGFβR1 signaling or the immune checkpoint inhibitor) if the cancer is predicted not to respond to the therapy.

In some embodiments, the subject has a solid tumor. Exemplary tumors include colorectal tumors, lung tumors, head and neck squamous cell carcinomas, renal cell carcinomas, or melanomas.

The foregoing and other features of the disclosure will become more apparent from the following detailed description, which proceeds with reference to the accompanying figures.

BRIEF DESCRIPTION OF THE DRAWINGS

FIG. 1A is a treatment schema in the CT26 tumor model. Six to eight week old BALB/c mice were implanted subcutaneously in the left flank with 2×10$^5$ CT26 tumor cells. Seven days following implant, animals were randomized based on tumor size, and vehicle control or LY2157299 compound were administered by oral gavage twice daily every 12 hours at 150 mg/kg for 7 consecutive days. At day 14, some mice received five consecutive radiation treatments of 5 Gy targeted to tumor tissue along with 25 mg/kg injections of 5-fluorouracil (5FU) chemotherapy administered intraperitoneally on days 14, 16, and 18. LY treatment groups resumed BID oral dosing from days 21-27. Mean tumor growth (i) and survival (ii) were assessed three times per week up to 100 days or death (FIG. 1B). FIG. 1C shows representative phospho-SMAD2 and CD8a$^+$ co-immunofluorescent images from tumors harvested from mice at day 14 prior to cytotoxic therapy. Arrows identify pSMAD2$^+$ CD8$^+$ cells in vehicle mice. FIG. 1D shows mean tumor size (i) and survival (ii) of CT26 tumor bearing mice receiving the indicated treatment combinations and either anti-CD4 or anti-CD8a monoclonal antibodies to deplete CD4$^+$ and CD8α$^+$ cells prior to therapy. NS=not significant, *=p<0.05, =p<0.01, *=p<0.001.

FIG. 3B shows ALK5 PCR on DNA from FACS purified Foxp3$^+$ Tregs and Foxp3$^-$ conventional CD4$^+$ T cells harvested from 21-day MC38 tumors in ALK5$^{flox/flox}$ single transgenic (n=3) or Foxp3-eGFPCreERT2/ALK5$^{flox/flox}$ mice (n=2). Tamoxifen was administered for 5 consecutive days prior to implant to induce Cre recombination. White arrowheads identify Cre excised alleles. FACS analysis was carried out on single cell suspensions prepared from colons and tumors of single transgenic negative littermates or double transgenic ALK5$^{\Delta Foxp3}$ mice when tumors reached 144 mm$^2$ (FIG. 3C). Shown is the expression of the transcription factors Tbet and GATA3 in Foxp3$^+$ Tregs in the indicated tissue.

FIG. 4A shows survival and individual growth curves of MC38 tumor bearing mice on C57BL/6 (n=6-7) or CD8αCre-ALK5$^{flox/flox}$ (ALK5$^{\Delta CD8}$) (n=10-15) backgrounds. At day 14 or when average tumor size was ~25 mm$^2$, mice received tumor-directed radiation at 10 Gy ×2. Survival was tracked in mice when tumors reached 144 mm$^2$. Shown is one representative experiment of three total independent experiments. FIG. 4B shows tumor growth and survival as was measured in FIG. 4A, for MC38 tumors implanted subcutaneously into the left flank of non-transgenic littermate control (LM) or double transgenic Foxp3-eGFP-CreERT2/ALK5$^{flox/flox}$ (ALK5$^{\Delta Foxp3}$) mice. Prior to tumor implantation, all mice received five consecutive daily i.p. injections (1 mg/injection) of tamoxifen emulsified in sunflower oil. As before, mice received radiation in two doses of 10 Gy on consecutive days when tumors were ~25 mm$^2$. i-iv) Individual tumor growth curves for mice in each study group. v) Tumor area at day 16 in LM vs ALK5$^{\Delta Foxp3}$ mice. Shown is one representative experiment reflective of two independent experiments. FIG. 4C shows MC38 tumor growth and survival followed in C57BL/6 (n=10-12/group) and Lyz2Cre-ALK5$^{flox/flox}$ (ALK5$^{\Delta Lyz2}$) mice (n=9-12/group). Mice received radiation in two consecutive doses at 10 Gy when tumors were 25 mm$^2$. Shown is the compilation of two independent experiments. The number of mice with tumor cure/total number of mice per group is noted in the individual growth curves. *=p<0.05, **=p<0.01.

FIG. 5A is a schematic showing the treatment strategy in the MC38 tumor model. C57BL/6 Wild-type (n=6-9/group) and ALK5$^{\Delta CD8}$ (n=4-10/group) mice were implanted subcutaneously with MC38 tumor cells followed four days later by injection of some groups with anti-CD8a mAb to specifically deplete CD8$^+$ T cells. In other groups, mice also received LY2157299 via oral gavage twice daily (150 mg/kg) for seven days. Survival of mice was monitored until day 90 (FIG. 5B). FIG. 5C shows individual tumor growth curves for mice in each study group. The number of tumors cured over the total number of tumor-bearing mice is shown in the top right of each graph. Data from a representative experiment is shown reflective of two independent experiments total. ***=p<0.001.

FIG. 6A shows representative FACS plots from spleens of MC38 tumor bearing mice injected with depleting anti-CD8α or IgG1 isotype control harvested 14 days following injection. FIG. 6B shows survival and individual tumor growth curves in CT26 tumor bearing mice treated with i) vehicle control, ii) chemoradiation (RT/5-FU) on days 14-19, or iii) chemoradiation+LY3200882 from d7-13 and d21-27 (RT/5-FU/LY3200882). The number of mice cured over the total number of mice in each group is indicated in the top right corner. One representative experiment is shown reflective of two independent experiments. The treatment schema for FIGS. 6B and 6D is shown in FIG. 6C. Mice who eradicated their tumors were rechallenged with CT26 and 4T1 tumors. CT26 tumor cells were rechallenged on the opposite flank as from the original cured tumor. In FIG. 6D, 4T1 and CT26 tumor establishment and growth was followed for up to 60 days post re-challenge. The number of tumors rejected per total mice rechallenged in each tumor type is indicated in the top right portion of the graph. ***=p<0.001

FIG. 7A shows the quantification of $CD8^+$ T cells in lymph nodes and tumors by frequency (on left), and by absolute cell number in the lymph node or per $mm^2$ in the tumor (on right). The frequency of p15E tetramer positive $CD8^+$ T cells determined by FACS analysis in lymph nodes and tumors of WT and $ALK5^{\Delta CD8}$ mice is shown in FIG. 7B. FIG. 7C shows the frequency of effector memory ($CD44^{hi}/CD62L^-$), central memory ($CD44^{hi}/CD62L^+$), naïve ($CD44^{lo}/CD62L^+$), or effector ($CD44^{lo}/CD62L^-$) $CD8^+$ T cells. In FIG. 7D, the frequency of $Ly6C^+CD62L^-$ $CD8^+$ T cells in MC38 tumors or tumor draining inguinal lymph nodes from C57BL/6 or $ALK5^{\Delta CD8}$ mice is shown. The median fluorescent intensity of granzyme B (GnzB) expression gated on $CD44^{lo}CD62L^-$ $CD8^+$ T cells in MC38 tumors is shown in FIG. 7E. FIG. 7F shows the specific cytotoxic killing of tumor cells measured with the Incucyte live cell imaging system in co-cultures of MCA205-OVA or Panc02 tumor cells with CFSE-labeled C57BL/6 WT and $ALK5^{\Delta CD8+}$ T cells isolated from spleens of ΔactA-OVA vaccinated mice. Shown is the cumulative % dead tumor cells as determined by cytotox red reagent uptake of total tumor cells seeded following 24 hours of co-culture. FIG. 7G shows $CD8^+$ T cells purified from spleens of naïve WT and $ALK5^{\Delta CD8}$ mice and activated with increasing amounts of plate bound anti-CD3 and 10 μg/ml anti-CD28. i) Proliferation index measured by CFSE dye dilution, ii) IFN-γ secretion, and iii) TNF-α secretion. Each graph is reflective of at least two independent experiments. Representative t-distributed stochastic neighbor embedding (tSNE) plots of $CD8^+$ T cells were generated by FACS analysis of MC38 tumors from C57BL/6 or $ALK5^{\Delta CD8}$ mice (FIG. 7H). Gates are populations of Ly6C+/−$CD62L^+$/− overlaid in color on far left. Heat maps represent the minimum to maximum MFI value for each marker. *=p<0.05, =p<0.01, *=p<0.001, ****=p<0.0001. Error bars in each subpanel are standard deviations. DL=detection level.

In FIG. 8B, FACS analysis of myeloid cell subsets in the tumor of WT and $ALK5^{\Delta CD8}$ mice is shown. FIG. 8C shows IFN-$\gamma^+$ or TNF-$\alpha^+$ $CD8^+$ T cells in MC38 tumors determined by FACS intracellular cytokine staining analysis. Overlays of $CD8^+$ T cell tSNEs plots generated from FACS analysis of MC38 tumors of WT and $ALK5^{\Delta CD8}$ mice (FIG. 8D). FIG. 8E shows FACS analysis of tumors from vehicle and LY treated mice harvested on day 14, 24 hours after last LY dose. Shown is the frequency of total $CD3^+$ T cells, $CD8^+$ T cells, $CD4^+$ T cells, $CD11b^+$ cells of viable cells, and Tregs of $CD4^+$ T cells and macrophages of total $CD11b^+$ myeloid cells. FIG. 8F shows FACS analysis of lymph nodes, spleens, and tumors from CT26 tumor bearing mice treated with vehicle control or LY3200882 for 7 days. Shown is the percent EOMES (D) or Tbet (E) positive of $CD8^+$ T cells. NS=not significant, *=p<0.05, **=p<0.01.

FIG. 9A is a diagram showing the experimental schema for adoptive co-transfer of congenic C57BL/6 WT and $ALK5^{\Delta CD8+}$ T cells into MC38 tumor-bearing mice. FIG. 9B shows the frequency of transferred CD45.1 WT and CD45.2 $ALK5^{\Delta CD8}$ $CD8^+$ T cells (n=9 recipients) analyzed in the spleen, lymph node, and tumor, displayed as the mean averages in each specific tissue; each symbol represents one mouse. CD45.1 WT transferred T cells are represented by black circles and CD45.2 $ALK5^{\Delta CD8}$ transferred T cells are white boxes. A compilation of two independent experiments is shown. FIG. 9C shows the percent of $CFSE^{low}$ cells gated on CD45.1 WT or CD45.2 $ALK5^{\Delta CD8}$ transferred T cells in spleen, lymph node, and MC38 tumors. FIG. 9D shows in vitro proliferation of CFSE-labeled naïve $CD8^+$ T cells isolated from spleens of C57BL/6 or $ALK5^{\Delta CD8}$ mice induced by plate bound αCD3/αCD28 for 68 hours; n=3 replicates/group. Where indicated, groups were treated with 1 or 10 ng/ml TGFβ1 at the beginning of the assay. One representative experiment is shown, reflective of three independent experiments. The percent of $CXCR3^+$ transferred $CD8^+$ T cells is shown as assessed by FACS analysis 7 days post transfer in tumor bearing mice (FIG. 9E). FIG. 9F shows the frequency of $CXCR3^+CD8^+$ T cells in vitro following 68 hours of plate bound αCD3/αCD28 stimulation and +/−TGFβ1 treatment (n=3) as in FIG. 9D. One experiment is shown, reflective of three independent experiments. FIG. 9G shows the in vitro migration assay of WT and $ALK5^{\Delta CD8}$ $CD8^+$ T cells in response to given concentrations of CXCL10 treatment in the bottom chamber. FIG. 9H shows chromatin immunoprecipitation carried out using human Jurkat cells (i) and mouse primary $CD8^+$ T cells (ii) with anti-SMAD2 and anti-SMAD3 antibodies+/−TGFβ1 treatment, performed in triplicate. Experiment shown is representative of at least two independent experiments. NS=not significant, *=p<0.05, =p<0.01, *=p<0.001, ****=p<0.0001. Error bars in each subpanel are standard deviations FIG. 10A shows representative histograms of CFSE fluorescence in transferred $CD8^+$ T cells of WT and KO cells, overlaid and compared to the CSFE fluorescence of the mixed population prior to pre-transfer. $Ki67^+CD8^+$ T cells was determined by FACS analysis of lymph nodes and MC38 tumors of WT and $ALK5^{\Delta CD8}$ mice (FIG. 10B). FIG. 10C shows $CXCR6^+$ $CD8^+$ T cells as determined by FACS analysis of spleen, lymph nodes and MC38 tumors from adoptively transferred WT and $ALK5^{\Delta CD8}$ $CD8^+$ T cells from FIG. 9A. FIG. 10D shows in vitro migration of WT and ALK5-deficient $CD8^+$ T cells in response to CXCL10 and CXCL16 treatment in the bottom chamber. FIG. 10E shows FACS analysis of $CXCR3^+CD8^+$ T cells from lymph nodes, spleens, and tumors from CT26 tumor bearing mice treated with vehicle control or LY3200882 for 7 days.

*=p<0.05, =p<0.01, *=p<0.001.

Figure 11A:
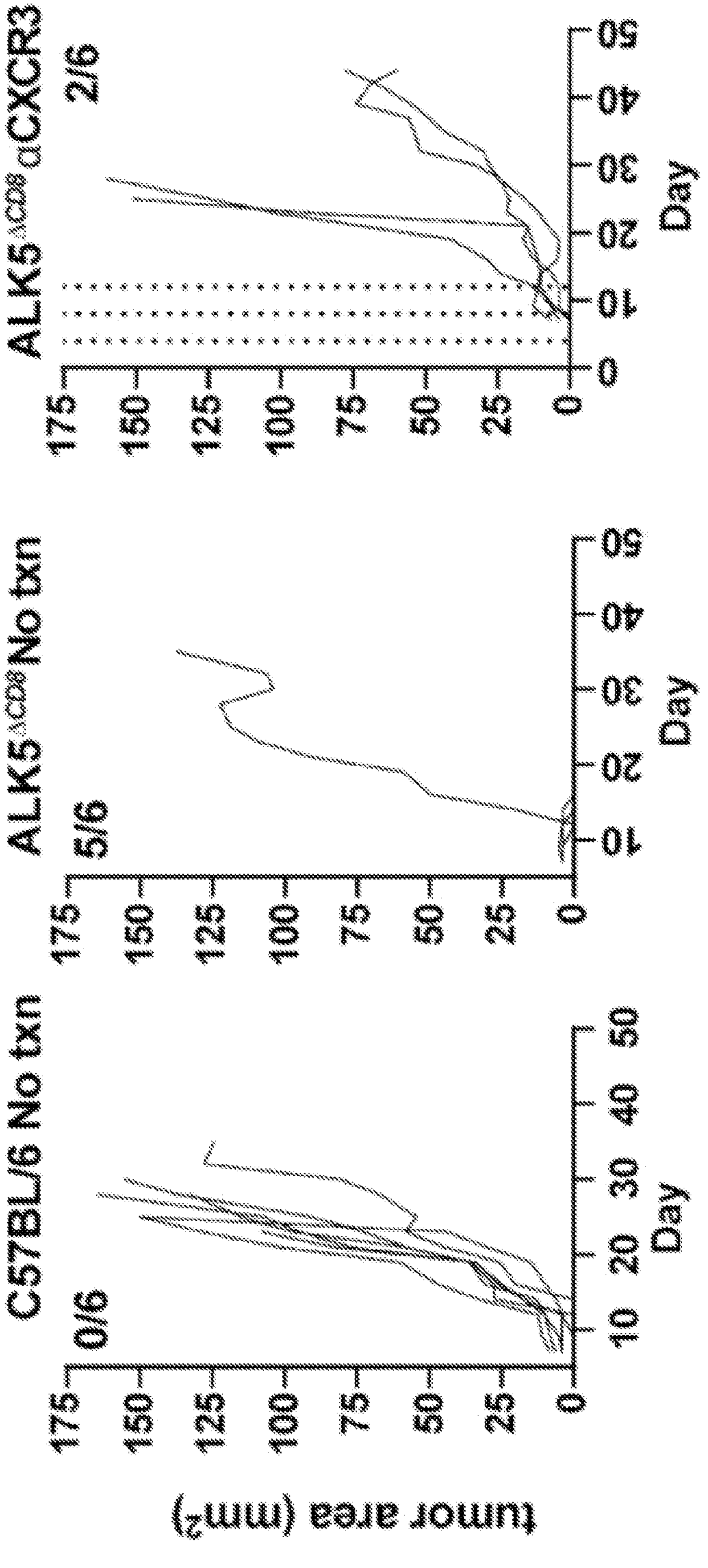
Figure 11B:
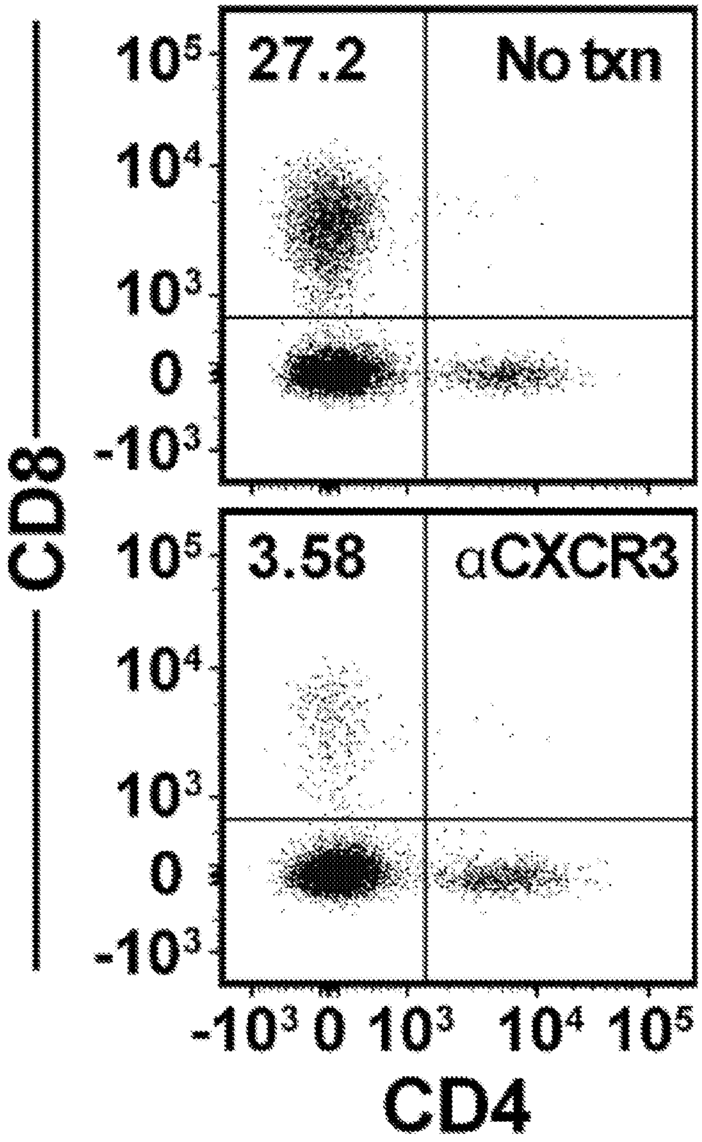

FIGS. 11A and 11B are a series of panels showing tumor rejection in $ALK5^{\Delta CD8}$ mice is dependent on CXCR3-dependent $CD8^+$ T cell chemotaxis. FIG. 11A shows MC38 tumor growth curves and survival in WT and $ALK5^{\Delta CD8}$ mice+/−αCXCR3 blocking antibody. One experiment is shown, reflective of two independent experiments. FIG. 11B shows representative FACS plots of tumors from a control C57BL/6 mouse or a C57BL/6 mouse treated with αCXCR3, harvested 4 days after the last dose. Shown is CD4 and CD8 expression gated on viable $CD45^+$ cells.

Figure 12A:
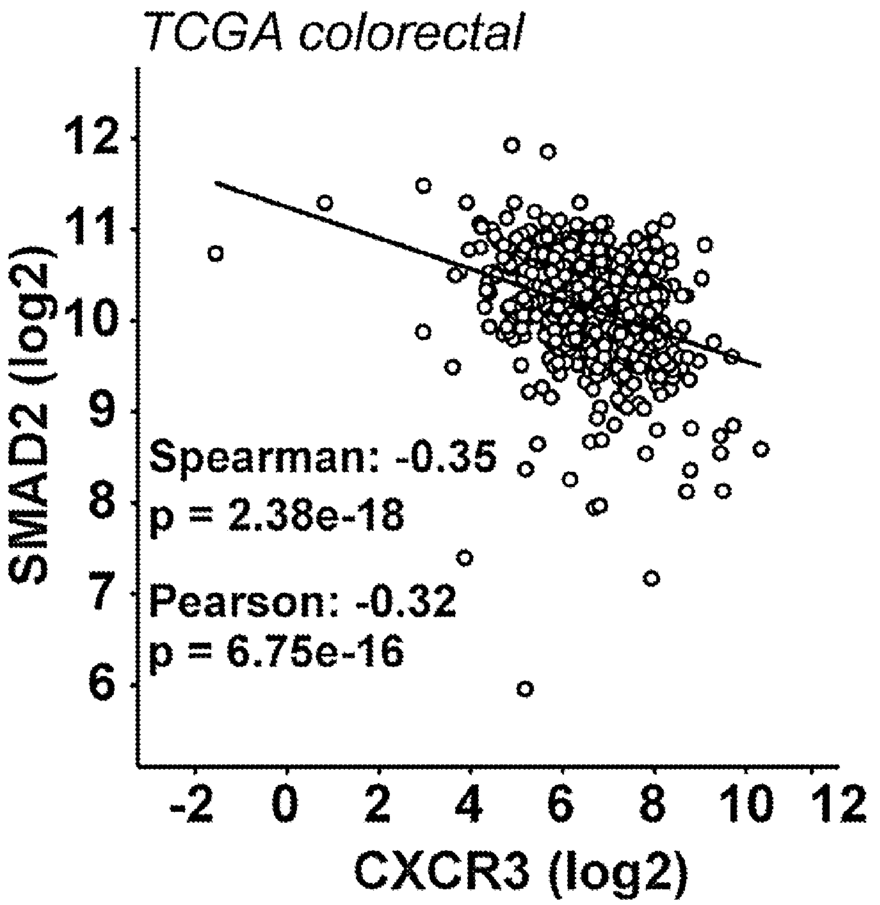
Figure 12B:
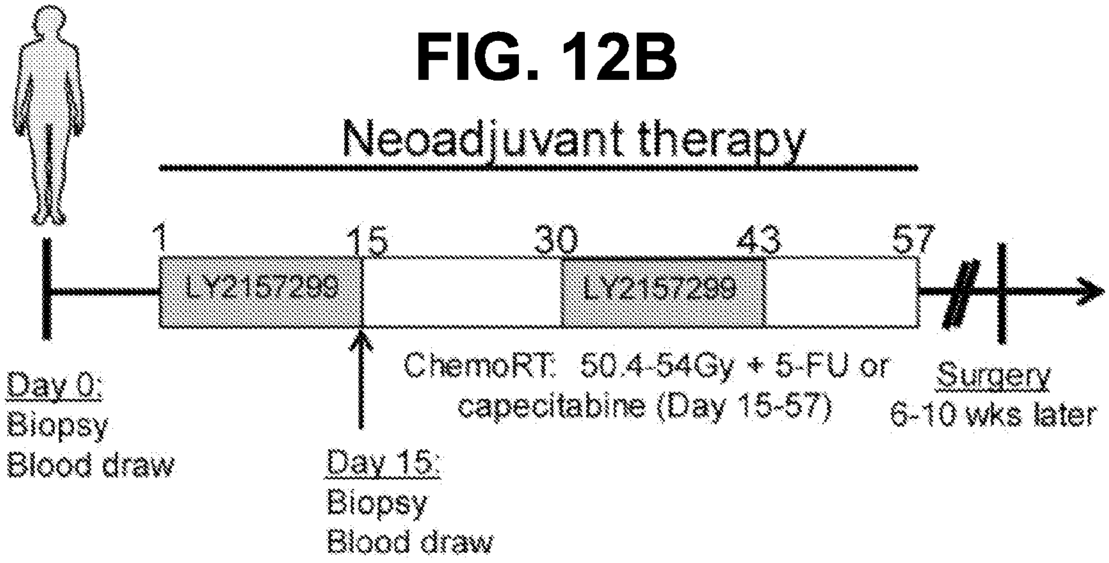
Figure 12C:
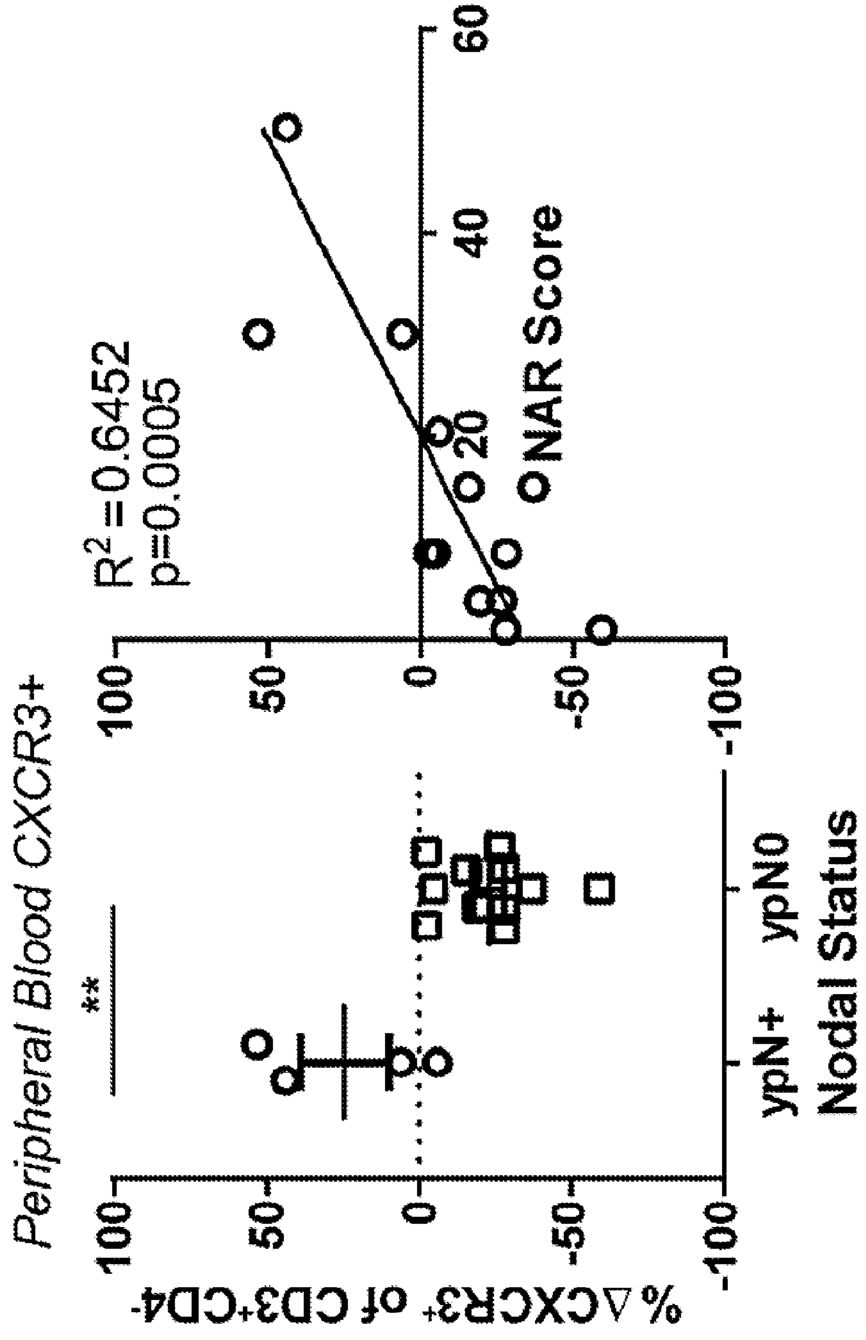
Figure 12D:
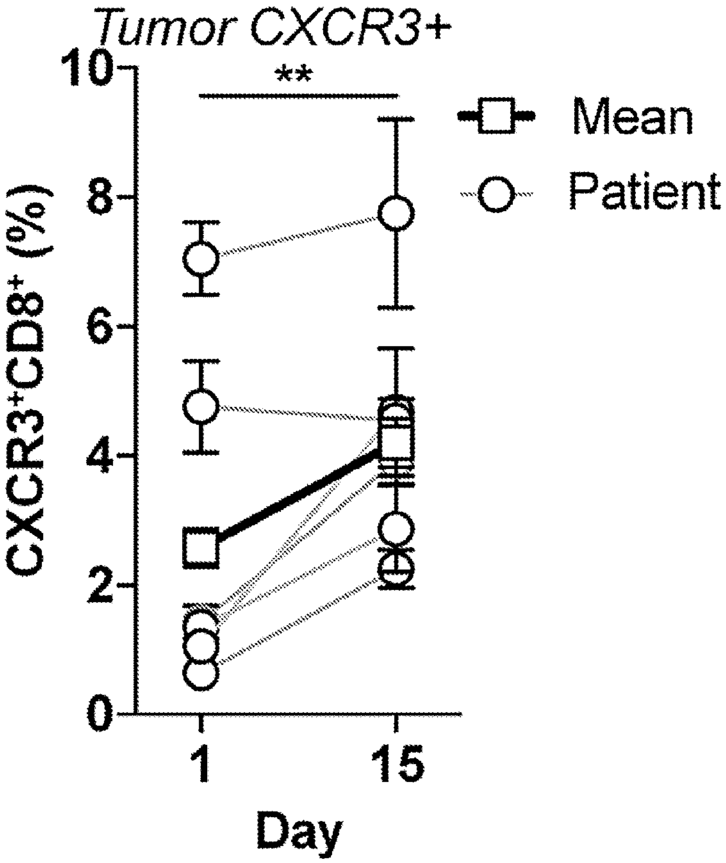
Figure 12E:
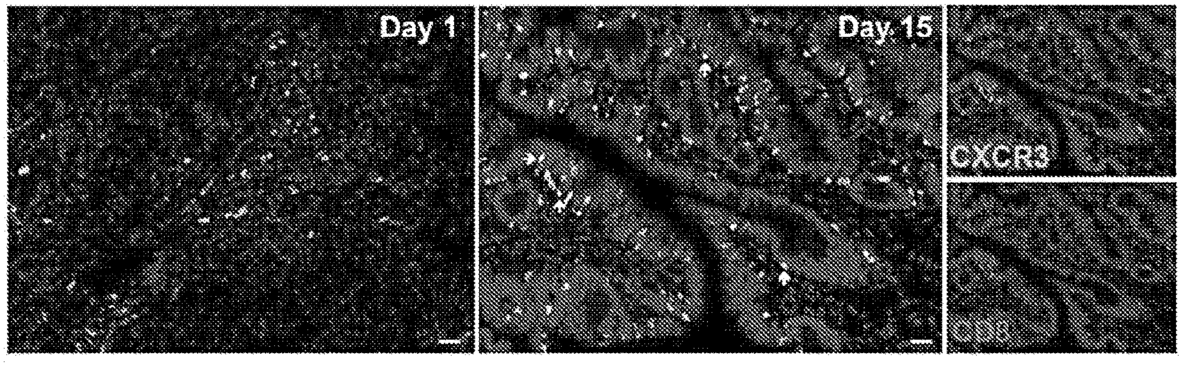

FIGS. 12A-12E are a series of panels showing TGFβ-mediated suppression of CXCR3-dependent $CD8^+$ T cell chemotaxis is relieved by LY2157299 in human patients with rectal cancer. FIG. 12A shows a linear regression analysis of SMAD2 and CXCR3 gene expression levels from a cohort of TCGA colorectal cancer patients. FIG. 12B illustrates the clinical trial schema for a phase II clinical trial of rectal cancer patients and sample collection intervals. Patients receive two cycles of LY2157299 on days 1-14 and again on days 30-43 while receiving standard of care chemoradiation on days 15-57 prior to surgery. FIG. 12C shows FACS analysis of peripheral blood cells from patients enrolled on trial showing the percent change in frequency of $CXCR3^+CD3^+CD4^-$ T cells between days 1 and 15 (left). Patients are grouped by nodal status following neoadjuvant treatment (ypN). On the right, percent change in frequency of $CXCR3^+CD3^+CD4^-$ T cells between days 1 and 15 is shown versus the neoadjuvant rectal (NAR) score. FIG. 12D shows the percent $CXCR3^+CD8^+$ tumor-infiltrating T cells of total DAPI cells in patient tumor biopsies. Each patient is shown (thin gray lines) along with the mean of all patients (thick black line). FIG. 12E shows representative immunofluorescent images of a trial patient used to quantitate $CXCR3^+CD8^+$ cells in FIG. 12D. *=p<0.05, =p<0.01, *=p<0.001. Error bars in each subpanel are standard deviations.

Figure 13A:
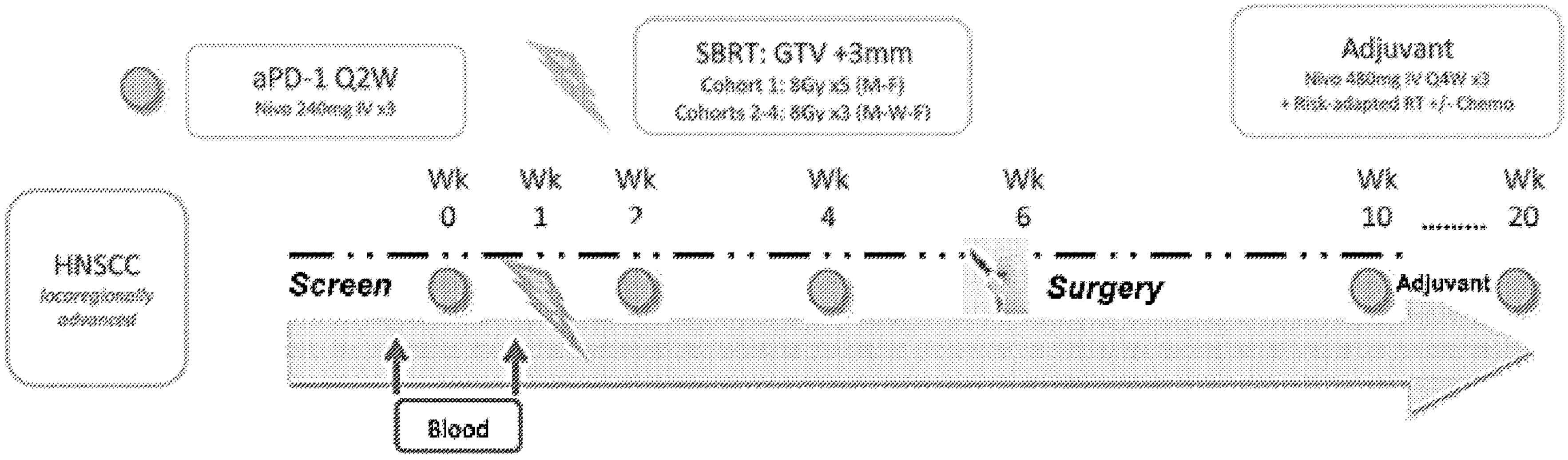
Figure 13D:
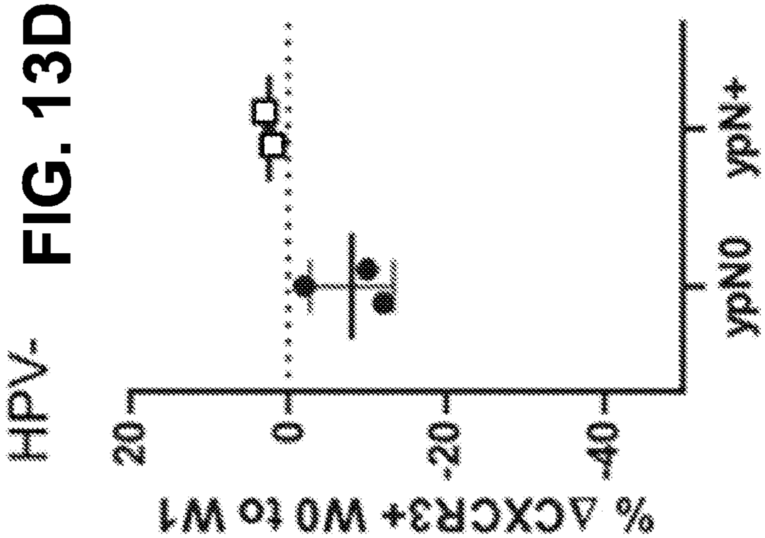
Figure 13C:
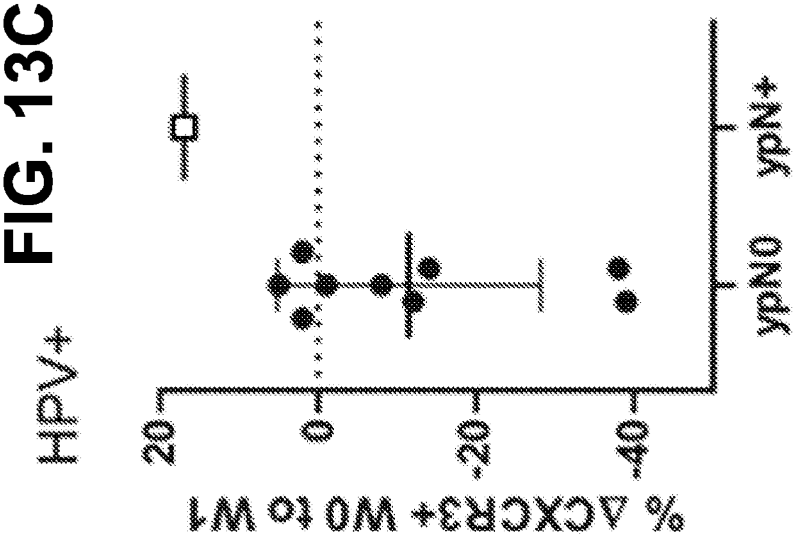
Figure 13B:
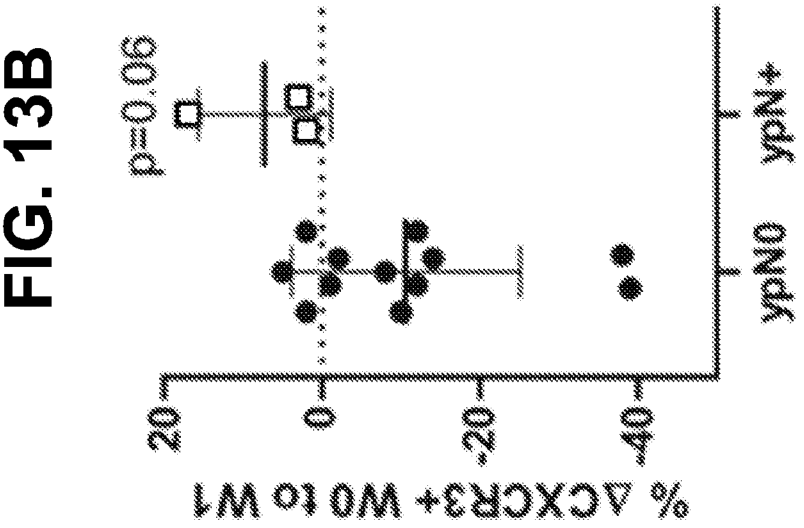

FIGS. 13A-13D are a series of panels showing change in $CXCR3^+$ cells in response to checkpoint blockade. FIG. 13A shows the treatment schema. Peripheral blood was drawn at baseline and one week after anti-PD-1 therapy (nivolumab). Surgery was performed at week six for pathologic assessment. FIG. 13B shows change in peripheral blood $CD3^+CD4^-CXCR3^+$ T cells in a cohort receiving anti-PD-1 therapy. Patients are grouped by nodal status following neoadjuvant treatment (ypN). FIGS. 13C and 13D show HPV+ patients from FIG. 13B and HPV-patients from FIG. 13B, respectively. Given the low number of patient(s) with residual nodal disease (ypN+), statistics could not be accurately performed in the HPV+ and HPV− subgroups.

SEQUENCE LISTING

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Mar. 10, 2022, and is 1,371 bytes, which is incorporated by reference herein.

SEQ ID NOs: 1 and 2 are human CXCR3 forward and reverse primers, respectively.

SEQ ID NOs: 3 and 4 are mouse CXCR3 forward and reverse primers, respectively.

SEQ ID NO: 5 is an ovalbumin peptide (SIINFEKL).

DETAILED DESCRIPTION

Local radiation treatment can lead to activation of tumor-specific immunity, and provides an opportunity to combine with immunotherapy to expand and propagate anti-tumor immunity (Kaur et al., *Front. Oncol.* 2:191, 2012; Formenti et al., *Nat. Med.* 24:1845-1851, 2018). However, radiation simultaneously induces immunosuppressive pathways, most notably, transforming growth factor beta (TGFβ1). TGFβ1 is upregulated following radiation, and contributes to tumor progression via promotion of epithelial to mesenchymal transition (EMT; David et al., *Cell* 164:1015-1030, 2016), stimulation of neoangiogenesis (Sounni et al., *Dis. Model. Mech.* 3:317-332, 2010), enhanced tumor cell motility and metastasis (Friedl et al., *Cell* 147:992-1009, 2011), cancer associated fibroblast (CAF) proliferation (Calon et al., *Cancer Cell* 22:571-584, 2012), and suppression of T cell effector function (Thomas et al., *Cancer Cell* 8:369-380, 2005). Furthermore, high TGF13 gene signatures indicate a unique resistance to checkpoint blockade therapy in colorectal and breast cancer patients (Mariathasan et al., *Nature* 554:544-548, 2018) As has been previously shown, blockade of TGF13 receptor (TGFβR) signaling or neutralization of TGF13 can relieve resistance to cytotoxic therapies as well as synergize with ICB (Garrison et al., *Cancer Immunol. Immunother.* 61:511-521, 2012; Tauriello et al., *Nature* 554:538-543, 2018; Ravi et al., *Nat. Commun.* 9:741, 2018; Holmgaard et al., *J. Immunother. Cancer* 6:47, 2018; Young et al., *Cancer Immunol. Res.* 2:1011-1022, 2014). Although these studies have demonstrated the association of TGF13 blocking therapies with enhanced T cell infiltration and immunity, the precise mechanism for why these therapies are effective remains unknown.

The inventors have shown how TGFβ suppresses anti-tumor immunity through the use of clinical ALK5 small molecule inhibitors and cell-type conditional ALK5-deficient mice. Blockade of ALK5 phosphorylation prior to chemoradiation treatment significantly reduced tumor growth and extended survival. This was associated with and dependent upon increased $CD8^+$ T cell tumor infiltration. The predominant therapeutic effect of ALK5 inhibition was directly on $CD8^+$ T cells; CD8α-specific deletion of ALK5 enhanced CXCR3 expression on $CD8^+$ T cells, resulting in increased CXCR3-dependent migration into tumors. The inventors show that CXCR3 was directly suppressed by TGFβ. Once in the tumor microenvironment, ALK5-deficient T cells exhibited a decreased threshold for T cell receptor (TCR) activation and cytotoxicity. These data demonstrate a novel mechanism by which TGFβ contributes to immunosuppression through downregulation of $CD8^+$ T cell expression of CXCR3, limiting trafficking to the tumor. Data provided herein, that combines ALK5 inhibition with chemoradiation in locally advanced rectal cancer, confirms the preclinical observations; increased $CXCR3^+CD8^+$ T cells infiltrated tumors after ALK5 inhibition, and changes in peripheral blood $CXCR3^+$ expression correlated with treatment response. These findings demonstrate a new mechanism by which TGFβ contributes to immune suppression, a mechanism that can be targeted in clinical trials, and translates these findings with clinical relevance.

I. Terms

Unless otherwise noted, technical terms are used according to conventional usage. Definitions of common terms in molecular biology may be found in *Lewin's Genes X*, ed. Krebs et al., Jones and Bartlett Publishers, 2009 (ISBN 0763766321); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk*

*Reference*, published by Wiley, John & Sons, Inc., 1995 (ISBN 0471186341); and George P. Rédei, *Encyclopedic Dictionary of Genetics, Genomics, Proteomics and Informatics*, 3rd Edition, Springer, 2008 (ISBN: 1402067534), and other similar references.

Unless otherwise explained, all technical and scientific terms used herein have the same meaning as commonly understood by one of ordinary skill in the art to which this disclosure belongs. The singular terms "a," "an," and "the" include plural referents unless the context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of the present disclosure, suitable methods and materials are described below. All publications, patent applications, patents, and other references mentioned herein are incorporated by reference in their entirety, as are the GenBank Accession numbers (for the sequence present on Sep. 12, 2019). In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Cancer: A malignant neoplasm that has undergone anaplasia with loss of differentiation, increased rate of growth, invasion of surrounding tissue, and/or is capable of metastasis. As used herein, cancer includes both solid tumors and hematological malignancies. Residual cancer is cancer that remains in a subject after any form of treatment is given to the subject to reduce or eradicate cancer. Metastatic cancer is a cancer at one or more sites in the body other than the original site of the cancer from which the metastatic cancer is derived. Local recurrence is a reoccurrence of the cancer at or near the same site as the original cancer, for example, in the same tissue as the original cancer.

Control: A sample or standard used for comparison with an experimental sample, such as a sample from a healthy subject, for example, a subject who does not have cancer. In some embodiments, the control is a historical control or standard reference value or range of values (e.g., a previously tested control sample, such as a group of healthy subjects, or group of samples that represent baseline or normal values). In further examples, a control may be one or more samples from a subject prior to a treatment (such as administration of one or more doses of an inhibitor of TGFβR1 signaling or ICB). Laboratory standards and values can be set based on a known or determined population value and can be supplied in the format of a graph or table that permits comparison of measured, experimentally determined values.

C-X-C motif chemokine receptor 3 (CXCR3): A G protein-coupled chemokine receptor that binds the chemokines CXCL4, CXCL9, CXCL10, and CXCL11. Effects of chemokine binding to CXCR3 include integrin activation, cytoskeletal changes, and chemotaxis. CXCR3 nucleic acid and amino acid sequences are publicly available. Nucleic acid sequences include GenBank Accession Nos. XM_017029436, XM_005262257, XM_005262256, XM_017029435, NM_001504, and NM_001142797 (human) and NM_009910 (mouse), all of which are incorporated here by reference as present in GenBank on Sep. 12, 2019 Amino acid sequences include GenBank Accession Nos. XP_016884925, XP_005262314, XP_005262313, XP_016884924, NP_001495, and NP_001136269 (human) and NP_034040 (mouse), all of which are incorporated here by reference as present in GenBank on Sep. 12, 2019. Additional CXCR3 sequences can be identified by one of ordinary skill in the art, for example, based on sequence similarity.

LY2157299 (LY): Also known as galunisertib. A small molecule inhibitor of transforming growth factor β receptor type 1 (TGFβR1), having the structure:

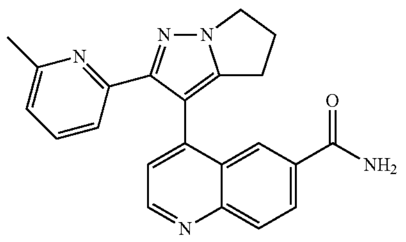 [SMILES: Cc1cccc(-c2nn3c(c2-c2ccnc4ccc(C(N)=O)cc24)CCC3)n1]

T cell: A white blood cell involved in the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, are involved in antibody responses as well as killer T cell responses. In one embodiment, a $CD4^+$ T cell is a $CD4^+$ regulatory T cell. $CD8^+$ T cells carry the "cluster of differentiation 8" (CD8) marker. In one embodiment, a $CD8^+$ T cell is a cytotoxic T lymphocyte (CTL). In another embodiment, a $CD8^+$ T cell is a suppressor T cell.

TGFβR1: TGF-β receptors are serine/threonine protein kinases. The type I and type II TGF-β receptors form a heterodimeric complex when bound to TGF-β, transducing the TGF-β signal from the cell surface to the cytoplasm. TGFBR1 is also known as AATS; ALK5; SKR4; ALK-5; LDS1A; LDS2A; TGFR-1; ACVRLK4; and transforming growth factor beta, receptor 1. Human TGFβR1 nucleic acid sequences include GenBank Accession Nos. XM_011518949, XM_017015063, NM_001306210, NM_004612, NM_001130916, XM_011518950, XM_024447658, and XM_011518948, all of which are incorporated here by reference as present in GenBank on Sep. 12, 2019. Human TGFβR1 amino acid sequences include GenBank Accession Nos. XP_011517251, XP_016870552, NP_001293139, NP_004603, NP_001124388, XP_011517252, XP_011517252, XP_024303426, and XP_011517250, all of which are incorporated here by reference as present in GenBank on Sep. 12, 2019. Additional TGFβR1 sequences can be identified by one of ordinary skill in the art, for example, based on sequence similarity.

Subject: A living multi-cellular vertebrate organism, a category that includes both human and veterinary subjects, including human and non-human mammals.

Tumor: All neoplastic cell growth and proliferation, whether malignant or benign, and all pre-cancerous and cancerous cells and tissues. In particular, non-limiting examples, a tumor is a colorectal tumor, rectal tumor, lung tumor, head and neck squamous cell carcinoma, or melanoma.

II. Methods of Treatment with CD8 T Cell-Mediated Immune Therapy

Disclosed herein are methods of treating a subject with cancer with CD8 T cell-mediated immune therapy. In particular embodiments, the methods include assessing and/or predicting response of a cancer in a subject to treatment with a CD8 T cell-mediated immune therapy (for example, an inhibitor of TGFβR1 signaling or an immune checkpoint inhibitor). The methods permit improved treatment decisions for patients, including continuing a treatment that is effective in treating and/or predicted to be effective in treating the cancer. In addition, if the treatment is not effective and/or is not predicted to be effective in treating the cancer, the treatment can be discontinued and one or more different treatments can be administered.

In some embodiments, the methods include measuring an amount of CXCR3-positive T cells in a peripheral blood sample (e.g. whole blood, plasma, or serum) from a subject following treatment of the subject with at least one dose of a CD8 T cell-mediated immune therapy, comparing the amount of CXCR3-positive T cells in the peripheral blood sample to a control, and predicting that the cancer will respond to the CD8 T cell-mediated immune therapy if the amount of CXCR3-positive T cells in the peripheral blood sample is decreased compared to the control or that the cancer will not respond to the CD8 T cell-mediated immune therapy if the amount of CXCR3-positive T cells in the peripheral blood sample is unchanged or increased compared to the control. In some embodiments, one or more samples is collected from a subject who has been administered one or more doses (e.g., 1-14 doses, such as 1, 2, 3, 4, 5, 6, 7, 8, 9, 10, 11, 12, 13, or 14 doses) of an CD8 T cell-mediated immune therapy. In some examples, the methods include administering at least one additional dose of the CD8 T cell-mediated immune therapy to a subject having a cancer predicted to respond to the therapy. In other examples, the methods include administering a treatment other than the CD8 T cell-mediated immune therapy to a subject having a cancer predicted not to respond to the CD8 T cell-mediated immune therapy. In some examples, the CXCR3-positive T cells are $CD3^+CD4^-$ T cells. In other examples, the CXCR3-positive T cells are $CD3^+CD8^+$ T cells.

In other embodiments, the methods include measuring an amount of CXCR3-positive T cells in a tumor sample from the subject following treatment of a subject with at least one dose of a CD8 T cell-mediated immune therapy, comparing the amount of CXCR3-positive T cells in the tumor sample to a control, and predicting that the cancer will respond to the CD8 T cell-mediated immune therapy if the amount of CXCR3-positive T cells is increased in the tumor sample compared to the control or that the cancer will not respond to the CD8 T cell-mediated immune therapy if the amount of CXCR3-positive T cells in the tumor sample is unchanged or increased compared to the control. In some embodiments, one or more samples is collected from a subject who has been administered one or more doses (e.g., 1-14 doses, such as 1, 2, 3, 4, 5, 6, 7, 8, 9, 10, 11, 12, 13, or 14 doses) of an CD8 T cell-mediated immune therapy. In some examples, the methods include administering at least one additional dose of the CD8 T cell-mediated immune therapy to a subject having a cancer predicted to respond to the therapy. In other examples, the methods include administering a treatment other than the CD8 T cell-mediated immune therapy to a subject having a cancer predicted not to respond to the CD8 T cell-mediated immune therapy. In some examples, the CXCR3-positive T cells are $CD3^+CD4^-$ T cells. In other examples, the CXCR3-positive T cells are $CD3^+CD8^+$ T cells.

In some examples, the CD8 T cell-mediated immune therapy administered to the subject (e.g., before and/or after measuring the amount of CXCR3-positive T cells in the sample) is a composition that inhibits TGFβR1 activity directly, such as LY2157299 (galunisertib), LY3200882, or derivatives or prodrugs thereof. Additional small molecule TGFRβR1 inhibitors include, but are not limited to GW788388, LY2109761, SB431542, SB525334, AZ12601011, and AZ12799734, or derivatives or prodrugs thereof. In other non-limiting examples, the CD8 T cell-mediated immune therapy is an immune checkpoint inhibitor, such as an anti-CTLA-4 antibody (e.g., ipilimumab), an anti-PD-L1 antibody (e.g., atezolizumab, avelumab, durvalumab, or spartalizumab), or an anti-PD-1 antibody (e.g., nivolumab, pembrolizumab, or cemiplimab). In further examples, the CD8 T cell-mediated immune therapy is a neutralizing TGFβ antibody (e.g., fresolimumab), a TGFβ trap (e.g., extracellular domain of TGFβR2) fused to a PD-L1 antibody (e.g., M7824, EMD Serono), or CAR-T cells expressing a dominant-negative TGFβRII. In still further examples, the CD8 T cell-mediated immune therapy is a TGFβ2 antisense nucleic acid (e.g., Trabedersen) or a vaccine that inhibits endogenous TGFβ, directly or indirectly (e.g., belagenpumatucel-L or gemogenovatucel-L).

In some examples the method includes selecting a subject that will benefit from the disclosed therapies, such as selecting a subject having decreased CXCR3-positive T cells in peripheral blood following treatment of a subject with at least one dose of a CD8 T cell-mediated immune therapy. For example, if the subject is determined to have decreased CXCR3-positive T cells in peripheral blood, the subject can be selected to be treated with at least one additional dose of the CD8 T cell-mediated immune therapy. Alternatively, if the subject is determined to have increased CXCR3-positive T cells in a tumor sample, the subject can be selected to be treated with a therapy other than CD8 T cell-mediated immune therapy.

In some examples, the methods include treating the subject by administering at least one additional dose of the CD8 T cell-mediated immune therapy (e.g., 1-14 additional doses) to the subject if the tumor is predicted to respond to the therapy. Dosages of the CD8 T cell-mediated immune therapy administered to the subject (e.g., before and/or after measuring amount of CXCR3-positive T cells in the sample) can be determined by a skilled clinician, depending on the compound, type of the tumor, the condition of the subject, and other factors. In some non-limiting examples, the subject is administered 300 mg of LY2157299 daily (e.g., in a divided dose). In other non-limiting examples, the subject is administered 240 mg of an anti-PD-1 antibody (such as nivolumab) every other week or 480 mg of an anti-PD-1 antibody once a month. In other examples, the subject is also administered chemotherapy and/or radiation treatment, which may be prior to, concurrent with, or after administering the at least one additional dose of the CD8 T cell-mediated immune therapy.

If treatment with the CD8 T cell-mediated immune therapy is discontinued, in some examples, the subject is administered an alternative treatment, including but not limited to, one or more of chemotherapy, radiation treatment, and surgery. In some examples, the chemotherapy is folinic acid, fluorouracil, and oxaliplatin (FOLFOX) chemotherapy, cetuximab, platinum-based chemotherapy (such as cisplatin, oxaloplatin, or carboplatin), 5-fluorouracil, gemcitabine, capecitabine, paclitaxel, docetaxel, irinotecan, or combinations of two or more thereof. A skilled clinician can select appropriate alternative treatment(s) based on the cancer being treated, the condition of the subject, and other clinical factors.

In some embodiments, the sample is peripheral blood from a subject with cancer, such as a subject with cancer who has been administered one or more doses of a CD8 T cell-mediated immune therapy. In some examples, the sample is whole blood, plasma, serum, or peripheral blood mononuclear cells. The sample may be utilized with minimal pre-treatment, or may undergo one or more pre-treatment steps, including one or more purification steps.

In other embodiments, the sample is a tumor sample from a subject with cancer, such as a subject with cancer who has been administered one or more doses of a CD8 T cell-mediated immune therapy. The tumor sample may be collected by any method, including biopsy or surgery. The sample may be utilized with minimal pre-treatment, or may undergo one or more pre-treatment steps, including one or more purification steps.

In some embodiments, measuring an amount of CXCR3-positive T cells in the sample is by positive and/or negative selection methods utilizing antibodies for CXCR3 and one or more T cell specific surface markers. Such methods include flow cytometry methods (such as fluorescence activated cell sorting, FACS) and immunomagnetic separation. In some examples, the methods include flow cytometry that includes detection of one or more T cells markers (such as CD3, CD4, and/or CD8) and detection of CXCR3. In one non-limiting example, $CD45^{+}CD3^{+}CD4^{-}CD8^{+}CXCR3^{+}$ T cells are evaluated by flow cytometry at baseline, and then after one cycle of the CD8 T cell-mediated immune therapy. In some examples, the amount of CXCR3-positive T cells is measured in a sample collected at least 3 days after administration of a CD8 T cell-mediated immune therapy, such as at least 3, 4, 5, 6, 7, 8, 9, 10, 11, 12, 13, 14, 15, 16, 17, 18, 19, 20, or 21 days after administration of the CD8 T cell-mediated immune therapy. In other examples, the amount of CXCR3-positive T cells is measured in a sample collected 3-28 days after administration of a CD8 T cell-mediated immune therapy, such as 3-7, 5-10, 7-14, 10-21, 15-24, or 21-28 days after administration of the CD8 T cell-mediated immune therapy.

The control can be any suitable control against which to compare an amount of CXCR3 expressing (e.g., CXCR3-positive) T cells in a sample from a subject (such as a peripheral blood sample and/or a tumor sample). In some embodiments, the control is a sample, or a plurality of samples, from the same subject prior to treatment with at least one dose of a CD8 T cell-mediated immune therapy (e.g., LY2157299). In other embodiments, the control sample is a sample, or plurality of samples, from a subject(s) known to respond, or known not to respond, to a CD8 T cell-mediated immune therapy (such as LY2157299). In further embodiments, the control is a reference value. For example, the reference value can be derived from the average CXCR3-positive T cells in peripheral blood or tumor samples obtained from a group of subjects known to respond, or known not to respond, to a CD8 T cell-mediated immune therapy (such as LY2157299).

A change in an amount of CXCR3 expressing T cells in a sample includes an increase or decrease compared to a control. An increase an amount of CXCR3 expressing T cells includes any detectable increase in an amount of CXCR3 expressing T cells, for example, compared to a control. In certain examples, an amount of CXCR3 expressing T cells increases by at least 5%, at least 10%, at least 15%, at least 20%, at least 25%, at least 30%, at least 35%, at least 40%, at least 45%, at least 50%, at least 60%, at least 70%, at least 80%, at least 90%, at least 2-fold, at least 3-fold or at least 4-fold, as compared to a control. A decrease an amount of CXCR3 expressing T cells includes any detectable decrease in an amount of CXCR3 expressing T cells, for example, compared to a control. In certain examples, an amount of CXCR3 expressing T cells decreases by at least 5%, at least 10%, at least 15%, at least 20%, at least 25%, at least 30%, at least 35%, at least 40%, at least 45%, at least 50%, at least 60%, at least 70%, at least 80%, at least 90%, at least 2-fold, at least 3-fold or at least 4-fold, as compared to a control).

In the methods described herein the subject may be administered at least one dose of a chemotherapeutic agent (a "chemotherapy") sequentially with (e.g., following) or concurrently with the CD8 T cell-mediated immune therapy (such as a TGFβR1 inhibitor or immune checkpoint inhibitor). Chemotherapeutic agents are selected based on the type of tumor being treated, and include alkylating agents, such as nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine); antimetabolites such as folic acid analogs (such as methotrexate), pyrimidine analogs (such as 5-fluorouracil, floxuridine, cytarabine, gemcitabine, capecitabine, azcitidine, and decitabine), and purine analogs (such as mercaptopurine, thioguanine, cladribine, clofarabine, fludarabine, or nelarabine); or natural products, for example vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase). Additional agents include platinum coordination complexes (such as carboplatin and cis-diamine-dichloroplatinum II, also known as cisplatin), substituted ureas (such as hydroxyurea), methyl hydrazine derivatives (such as procarbazine), and adrenocrotical suppressants (such as mitotane and aminoglutethimide); hormones and antagonists, such as adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testosterone proprionate and fluoxymesterone). Examples of the most commonly used chemotherapy drugs include adriamycin, melphalan (Alkeran®) Ara-C (cytarabine), carmustine, busulfan, lomustine, carboplatinum, cisplatinum, cyclophosphamide (Cytoxan®), daunorubicin, dacarbazine, 5-fluorouracil, fludarabine, hydroxyurea, idarubicin, ifosfamide, methotrexate, mithramycin, mitomycin, mitoxantrone, nitrogen mustard, paclitaxel (or other taxanes, such as docetaxel), vinblastine, vincristine, VP-16, gemcitabine (Gemzar®), irinotecan (CPT-11), leustatin, vinorelbine, imatinib (STI-571), Topotecan (Hycamtin®), capecitabine, and calcitriol.

In the methods disclosed herein the subject may be administered at least one dose of radiation therapy sequentially with (e.g., following) or concurrently with the CD8 T cell-mediated immune therapy (such as a TGFβR1 inhibitor or immune checkpoint inhibitor). In particular examples, the radiation therapy includes external beam therapy (for example, delivery of a beam of high-energy x-rays to the location of the tumor). In other examples, the radiation therapy includes intensity-modulated radiation therapy (IMRT), which is able to focus more precisely so that fewer healthy cells are destroyed than is the case with external beam therapy. IMRT reduces incidental damage to the structures near the tumor that may not be involved. Methods and dosages of radiation therapy can be determined by a skilled clinician, depending on the type and location of the tumor, the condition of the subject, and other factors. In one non-limiting example, the subject is administered about 50-55 Gy of radiation in 1.8 Gy daily doses, for a total of 28-30 fractions. In other examples, the subject is administered five daily doses of 8 Gy or three doses of 8 Gy every other day.

In some examples, the subject has cancer, such as a solid tumor or a metastasis of a solid tumor. Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytoma, sebaceous gland carcinoma, papillary carcinoma, papillary adenocarcinoma, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma, and retinoblastoma). In non-limiting examples, solid tumors that can be treated or inhibited by the methods disclosed herein include colorectal cancer, rectal cancer, lung cancer, head and neck squamous cell carcinoma, renal cell carcinoma, and melanoma. In other examples, the subject has a lymphoma, for example, T-cell large granular lymphocyte leukemia, polycythemia vera, lymphoma, diffuse large B-cell lymphoma, Hodgkin's lymphoma, non-Hodgkin's lymphoma (indolent and high grade forms), mantle cell lymphoma, or follicular cell lymphoma.

EXAMPLES

The following examples are provided to illustrate certain particular features and/or embodiments. These examples should not be construed to limit the disclosure to the particular features or embodiments described.

Example 1

Materials and Methods

Animal studies and cell culture: C57BL/6, BALB/c, CD8Cre, Lyz2Cre, and Foxp3-eGFP-CreERT2 mice were purchased from the Jackson Laboratories (Bar Harbor, Maine). ALK5flox/flox mice were a generous gift from Andrew Weinberg (Providence Cancer Center). All transgenic mice were on C57BL/6 background. CT26, MC38, 4T1 and MCA205-OVA tumor cells were grown in DMEM medium supplemented with 10% heat-inactivated fetal bovine serum and 1% penicillin-streptomycin to 60-90% confluence prior to tumor implantation. All cells were washed 2× with 1×PBS and implanted subcutaneously in a 100 μl volume of 1×PBS in the lower flanks. $1\times10^5$ MC38 cells, $2\times10^5$ CT26 cells, $5\times10^4$ 4 T1 cells, and $5\times10^6$ MCA205-OVA cells were used for tumor induction. Tumors were measured 3×/week until they reached the survival end-point of 144 $mm^2$. Mice were dosed with LY2157299 and LY3200882 via twice daily oral gavage at 105-150 mg/kg with doses spaced 12 hours apart for the indicated durations. 5-fluoruracil (5-FU) chemotherapy was administered at 25 mg/kg i.p. three times per week for one week. Radiation was delivered with a small animal radiation research platform (Xstrahl, Atlanta, GA) with cone beam-CT image guidance as previously described (Gunderson et al., *PLoS One* 14:e0211117, 2019). Anti-CD4 (GK1.5), anti-CD8α (2.43) and anti-CD8b (53-5.8) depleting antibodies were purchased from BioXcell and injected i.p. at 200 μg/mouse at the indicated time-points in the figures. Spleen, lymph nodes and tumors were harvested from animals and single cell suspensions were prepared using mechanical disaggregation for spleen and lymph nodes only or mincing and enzymatic digestion for 30 min. at 37° C. for tumors and lymph nodes for dendritic cell evaluation. Enzyme digest buffer included 1 mg/ml Collagenase A (Roche), 1 mg/ml Hyaluronidase (Sigma) and 50 U/ml DNase (Roche) in DMEM serum free base medium. Following single cell preparation, cells were washed and resuspended in FACS buffer (1×PBS, 1% BSA, 2 mM EDTA) and counted prior to FACS staining using a Guava EasyCyte cytometer (Millipore). Primary T cells were cultured in complete RPMI media (10% heat-inactivated FBS, 1% Na-P, 1% NEAA, 10 mM HEPES, 55 μM β-mercaptoethanol, and 1% Pen/Strep).

Clinical trial analysis: Patients enrolled in clinical trial NCT02688712 provided consent prior to tissue collection as designed and approved in PHS IRB #15-050. Whole blood from patients was collected at the indicated time-points in heparin coated tubes and stained for flow cytometry analysis by the Immune Monitoring Lab (Earle A. Chiles Research Institute, Providence Cancer Center) as previously described (Koguchi et al., *J. Vis. Exp.* 8:e53485, 2016). Pathological assessment for neoadjuvant treatment response was evaluated in the surgical resection specimen including excised lymph nodes. Neoadjuvant rectal (NAR) score was calculated by the published, validated formula (George et al, *Curr. Colorectal Cancer Rep.* 11: 275-280): $[5*ypN-3(cT-ypT)+12]^2/9.61$.

Immunofluorescence: Human rectal cancer biopsies were fixed in 10% NBF overnight and mouse tumors were fixed in zinc fixative overnight prior to tissue processing and paraffin embedding followed by sectioning cut at 5 microns for immunofluorescent staining. All primary antibodies were sequentially stained for 1 hour at RT diluted in a blocking/diluent buffer (Perkin Elmer) at the following concentrations: anti-CXCR3 (1:2000, MAB160), anti-human CD8 (1:400, SP16), anti-mouse CD8 (1:200, 4SM15), and anti-phosphoSMAD2 (1:10,000, EPR2856) followed by MACH-2 anti-Rabbit or Mouse HRP-conjugated polymer (Biocare Medical) or for 10 min at RT or anti-Rat/HRP polymer (Vector labs) for 30 min. at RT. Fluorescent signal was produced by staining with TSA-conjugated Opal dyes (Perkin Elmer) for 10 min at RT using OPAL-520, OPAL-540, and OPAL-620. Sections were then counterstained in DAPI and mounted. Images were acquired on a Vectra 3.0 automated pathology imaging system (Perkin Elmer).

Flow Cytometry: For ex vivo cytokine analysis, cells were first treated with a 1× cell activation cocktail of PMA/ionomycin/Brefeldin A (Biolegend) for 5 hours in complete RPMI media. One million cells from single cell suspensions were stained with anti-CD16/CD32 Fc block (1:200, BD Biosciences) and fixable viability 700 dye (1:10,000, BD Biosciences) in 1×PBS for 15 min. at 37° C. prior to surface and intracellular staining with primary antibodies. Surface staining commenced in 200 μl FACS buffer supplemented with a 1:4 dilution of Brilliant Violet stain buffer (BD Biosciences) and fluorescently conjugated antibodies (Table 1) for 30 min at 4° C. in the dark; all are mouse reactive antibodies unless otherwise indicated. Following surface staining cells were washed and fixed in either 2% PFA or Fix/Perm buffer (eBioscience) for 20 min at 4° C. for intracellular stain. Fix/perm buffer was washed with 1× perm wash buffer (eBioscience) and intracellular proteins were stained with fluorescently conjugated ICS antibodies in perm wash buffer for 30 min. at 4° C. in the dark. Cells were washed and resuspended in 1×PBS prior to acquisition on a BD Fortessa or LSRII flow cytometer (BD Biosciences).

TABLE 1

Antibodies for Flow Cytometry

| Antigen | Fluorescent conjugate | Dilution | Vendor |
|---|---|---|---|
| CD4 | BV605 | 1:400 | BD Biosciences |
| CD8a | APC-Cy7 | 1:400 | BD Biosciences |
| CD3e | PerCP-EF710 | 1:200 | eBioscience |
| CD45 | BV510 | 1:400 | BD Biosciences |
| CD11b | PE-Cy7, BV605 | 1:5000, 1:1000 | BD Biosciences |
| MHCII (IA-IE) | EF450 | 1:1000 | eBioscience |
| CD11c | APC-Cy7, PE-Cy7 | 1:400 | BD Biosciences |
| IFNγ | APC | 1:400 | BD Biosciences |
| Ki67 | APC | 1:400 | eBioscience |
| GnzB | FITC | 1:200 | BD Bioscience |
| P15E tetramer | PE | 1:2000 | NIH tetramer core |
| TNFα | PE-Cy7 | 1:400 | BD Bioscience |
| CD103 | PE, APC | 1:400 | BD Biosciences |
| F4/80 | APC | 1:400 | BD Biosciences |
| CD44 | BV711 | 1:800 | BD Biosciences |
| CD62L | PE-Cy7 | 1:800 | eBioscience |
| Ly6C | PerCP-Cy5.5 | 1:400 | eBioscience |
| Ly6G | FITC | 1:500 | BD Biosciences |
| PD1 | BV786 | 1:200 | BD Biosciences |
| Tbet | BV650 | 1:200 | BD Biosciences |
| EOMES | PE | 1:200 | eBioscience |
| CD80 | PE-CF594 | 1:400 | eBioscience |
| CD40 | FITC | 1:200 | BD Biosciences |
| Foxp3 | EF450 | 1:200 | eBioscience |
| GATA3 | EF660 | 1:200 | eBioscience |
| CXCR3 | BV421 | 1:200 | BD Biosciences |
| CXCR6 | BV711 | 1:200 | Biolegend |
| KLRG1 | PE-DAZZLE 594 | 1:200 | Biolegend |
| CD4 (human) | PerCP-Cy5.5 | 1:50 | BD Biosciences |
| CD3 (human) | AF700 | 1:75 | BD Biosciences |
| CXCR3 (human) | PE-CF594 | 1:150 | BD Biosciences |
| CD45 (human) | FITC | 1:100 | BD Biosciences |

Chromatin Immunoprecipitation: Mouse primary $CD8^+$ T cells were isolated and purified from spleens by magnetic negative selection using a mouse $CD8\alpha^+$ T cell isolation kit (Miltneyi Biotec). Cells were then plated in complete media on αCD3/αCD28 (1 μg/ml) coated 6 well plates at $2\times10^6$ cells/well to initiate rapid expansion. Seventy-two hours later, cells were harvested and plated in T-75 flasks in fresh RPMI complete supplemented with 60 units/ml hIL-2. Media was exchanged with new IL-2 media every 48 hours thereafter until cultures reached $>180\times10^6$ cells. Cells were harvested and exchanged with serum starvation media (RPMI complete+0.2% FBS) overnight and then stimulated with or without 2 ng/ml mouse recombinant TGFβ1 (R&D systems) for 1.5 hours. Jurkat cells were cultured and serum starved with 0.2% FBS RPMI media for overnight and stimulated with or without 10 ng/ml human recombinant TGFβ1 (PeproTech) for 1.5 hours. Four million Jurkat cells were used for each immunoprecipitation and $1.5\times10^7$ mouse $CD8^+$ T cells were used for one immunoprecipitation. ChIP was performed following SimpleChIP Enzymatic Chromatin IP Kit (Cell Signaling Technology) per manufacturer's instructions. Briefly, chromatin from fixed cells was sonicated by Vibra-cell VC130 (Sonics&Materials) for 2 cycles of 6 sec ON and 30 sec OFF at 6-9 output watt. Chromatin was incubated with anti-rabbit IgG (1:500), anti-Smad2 (1:50), or anti-Smad3 (1:50) (Cell Signaling Technology) at 4° C. overnight with rotation Immunoprecipitated samples were eluted and the DNA cross-links were reversed at 65° C. for 5 hours or overnight. Sheared chromosomal DNA was subjected to quantitative RT-PCR using FastStart Universal SYBR Green Master (Roche) and StepOnePlus Real-Time PCR system (Thermo Scientific). Primer sequences (5' to 3') used were as follows: human CXCR3 FOR: AAGCTGGGCCTGATTCTGTC (SEQ ID NO): 1), REV: AAGTCTGTGGTGGGCTTCTG SEQ ID NO: 2). mouse CXCR3 FOR: GGCTCCTCCTGACAACAGAC (SEQ ID NO: 3), REV: TGCCCAGGCTGACTTCATAC (SEQ ID NO: 4).

T Cell Adoptive Transfer Experiments: $CD8^+$ T cells were purified from spleens of naïve CD45.1 C57BL/6 and CD45.2 $ALK5^{\Delta CD8}$ mice, mixed in equal ratios, and labeled with 1 μM CFSE (Molecular Probes) prior to adoptive transfer into C57BL/6 mice bearing MC38 tumors 14 days post-implant. Seven days following transfer, tumors, spleens, and draining lymph nodes were harvested for FACS analysis.

Cytotoxicity assay: C57BL/6 and $ALK5^{\Delta CD8}$ mice were vaccinated with a replication deficient *Listeria monocytogenes* vaccine vector engineered to express ovalbumin (ΔActA-OVA). Mice were primed with $10^7$ bacteria intravenously followed by a boost 3 weeks later. Seven days following the vaccine boost $CD8^+$ T cells were purified from spleens via magnetic negative selection and labeled with 10 μM CFSE prior to co-culture with various ratios of unlabeled MCA205-OVA or Panc02 tumor cells. Realtime co-cultures were monitored with the IncuCyte S3 Live-Cell Analysis system (Sartorius) in the presence of Cytotox Red reagent (Essen Biosciences) for the detection of dead cells. The percent specific tumor cell cytotoxicity was calculated as follows [(total dead cells−dead CFSE+ T cells)/total # of tumor cells plated]×100.

In vitro T cell activation: $CD8^+$ T cells were purified from spleens of naïve C57BL/6 and $ALK5^{\Delta CD8}$ mice via magnetic negative selection and labeled with 1 μM CFSE prior to culture. Cells were cultured at $1\times10^5$ cells/well on αCD3/αCD28 (1 μg/ml, 10 μg/ml) coated 96 well plate in RPMI complete medium. Following 72 hours of culture, cells were harvested for FACS analysis of CFSE dye dilution and analyzed using the proliferation plug-in on FlowJo software (BD Biosciences). Supernatants were also collected from these cultures for cytokine analysis by cytokine bead array using the mouse inflammation kit (BD Biosciences) per manufacturer's instructions. In some assays, certain groups received recombinant mouse TGFβ1 (R&D systems) at 1 ng/ml at the initiation of the experiment.

T cell migration assay: $CD8^+$ T cells were purified from spleens of naïve CD45.1 C57BL/6 and CD45.2 $ALK5^{\Delta CD8}$ mice and mixed in equal ratios of $1\times10^5$ cells/genotype prior to plating in the top well of a 96 well transwell plate with a 3 micron pore size. Complete RPMI media with or without increasing concentrations of CXCL10 or CXCL16 was placed in the bottom chamber of the transwell plate. Cells were collected from the bottom portion of the well following 24 hours culture and analyzed by FACS for the number of WT or KO T cells.

PCR for Cre Excision of ALK5: $CD4^+$ T cells, B cells, $CD8^+$ T cells, $Foxp3^+$ Tregs, and macrophages were FACS sorted with an Aria II (BD Biosciences) and collected directly into cell lysis solution for genomic DNA isolation. gDNA was subsequently isolated using a DNeasy blood and tissue kit (Qiagen). PCR was performed with a 3-primer system as originally described (Larsson et al., *The EMBO Journal* 20:1663-1673, 2001) using Terra PCR direct polymerase mix (Clontech). PCR products were electrophoresed on a 1.5% agarose gel stained with GelRed DNA stain.

TCGA Data: RNAseq data was mined from TCGA—colorectal PanCancer Atlas data set on the cBioPortal for cancer genomics (cbioportal.org). SMAD2 and CXCR3 normalized mRNA expression levels were compared by linear regression analysis.

Statistics and Data Analysis: Graphpad Prism 7.0 software was used to construct all graphs and calculate statistical significance. FlowJo software was used to analyze FACS data and generate tSNE plots. When comparing two groups within an experiment the student's T test was used to determine statistical significance. When more than two biological or treatment groups were compared, one-way Anova was used to calculate p values. Significance from Kaplan-Meier survival curves were calculated with the Log-Rank test.

Example 2

TGFβ Inhibition Sensitizes Mouse Rectal Tumors to Chemoradiation

Figure 1A:
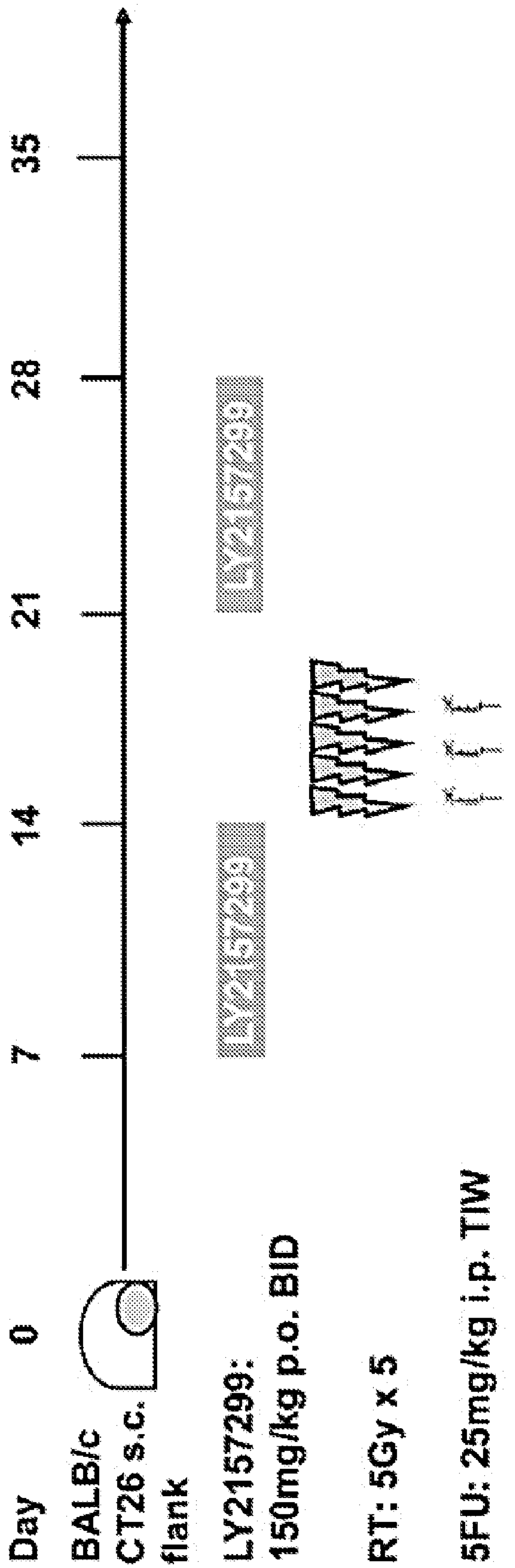
FIGS. 1A-1D are a series of panels showing that the TGFβR1 antagonist LY2157299 enhances chemo-radiation efficacy dependent on CD8α$^+$ cells in CT26 tumors.
Figure 1B:
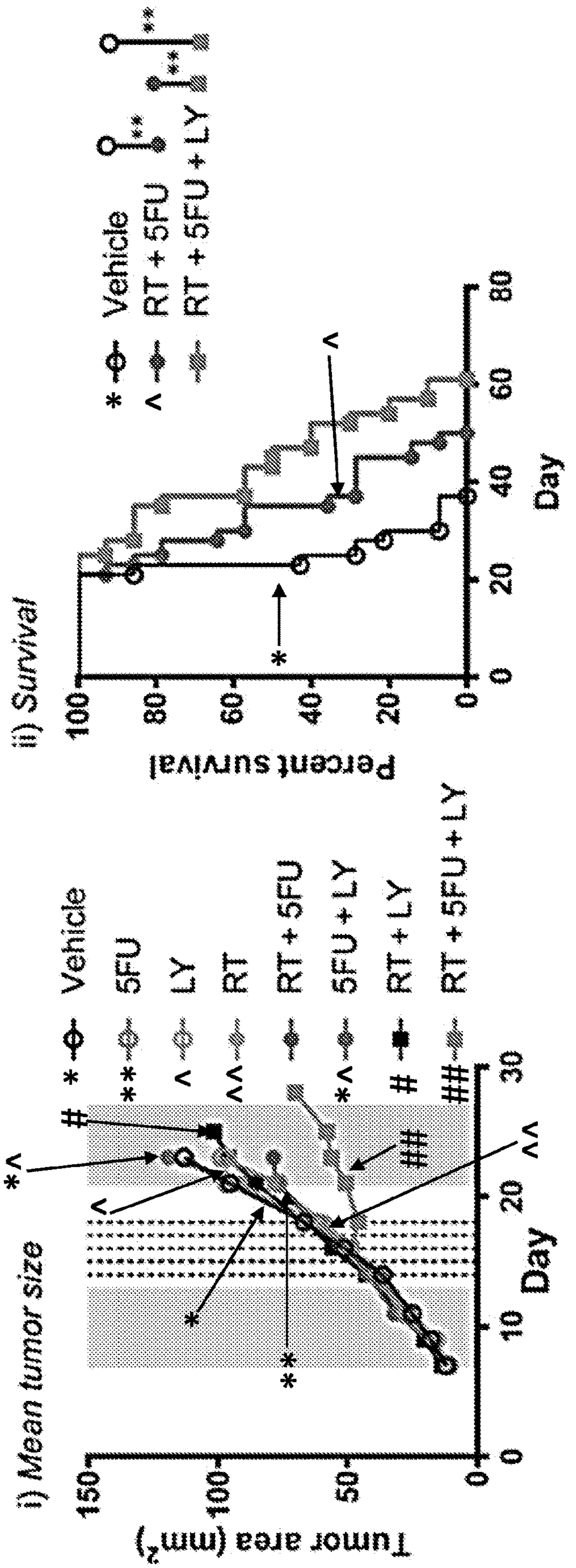

As previously shown (Bouquet et al., Clin. Cancer Res., 2011; Garrison et al., Cancer Immunol. Immunother., 2012; Young et al., Cancer Immunol. Res., 2014; Vanpouille-Box et al., Cancer Res., 2015), TGFβ blockade combined with radiation reduces tumor growth in various murine models. This therapeutic strategy was tested using a clinically relevant small molecule inhibitor of ALK5, LY2157299 (LY, also known as Galunisertib), administered prior to chemoradiation in mice bearing established colorectal tumors. LY was evaluated in combination with 5-FU chemotherapy and radiation (RT), either 2 Gy×15 ($BED_{10}$ 36) or 5 Gy daily for 5 consecutive days ($BED_{10}$ 37.5), mirroring standard of care clinical dosing schedules for neoadjuvant treatment of rectal cancer patients. As no difference was seen between 2 Gy×15 and 5 Gy×5 (data not shown), for practicality, 5 Gy×5 was used for the remainder of the preclinical modeling (FIG. 1A). Although RT+5FU alone provided a modest survival advantage over vehicle control (median survival 35 d vs 23d, p<0.01; FIG. 1B), the addition of LY significantly slowed tumor growth and provided the greatest survival benefit to tumor-bearing mice (FIG. 1B, median survival 45d, p<0.01). In order to understand whether adaptive immunity contributed to this therapeutic effect, $CD4^+$ cells and $CD8\alpha^+$ cells were depleted prior to treatment, beginning day 4. The data demonstrated that $CD8\alpha^+$ cells were required for efficacy, but $CD4^+$ cellular depletion prior to chemoradiation improved the efficacy over RT+5FU alone and recapitulated the RT+5FU+LY efficacy, however it did not provide any additional benefit beyond that seen with RT+5FU+LY (FIG. 1D). These data indicate that $CD8\alpha^+$ cells, but not $CD4^+$ cells, are necessary for the improved efficacy of chemoradiation plus ALK5 inhibition in CT26 tumors.

Figure 1C:
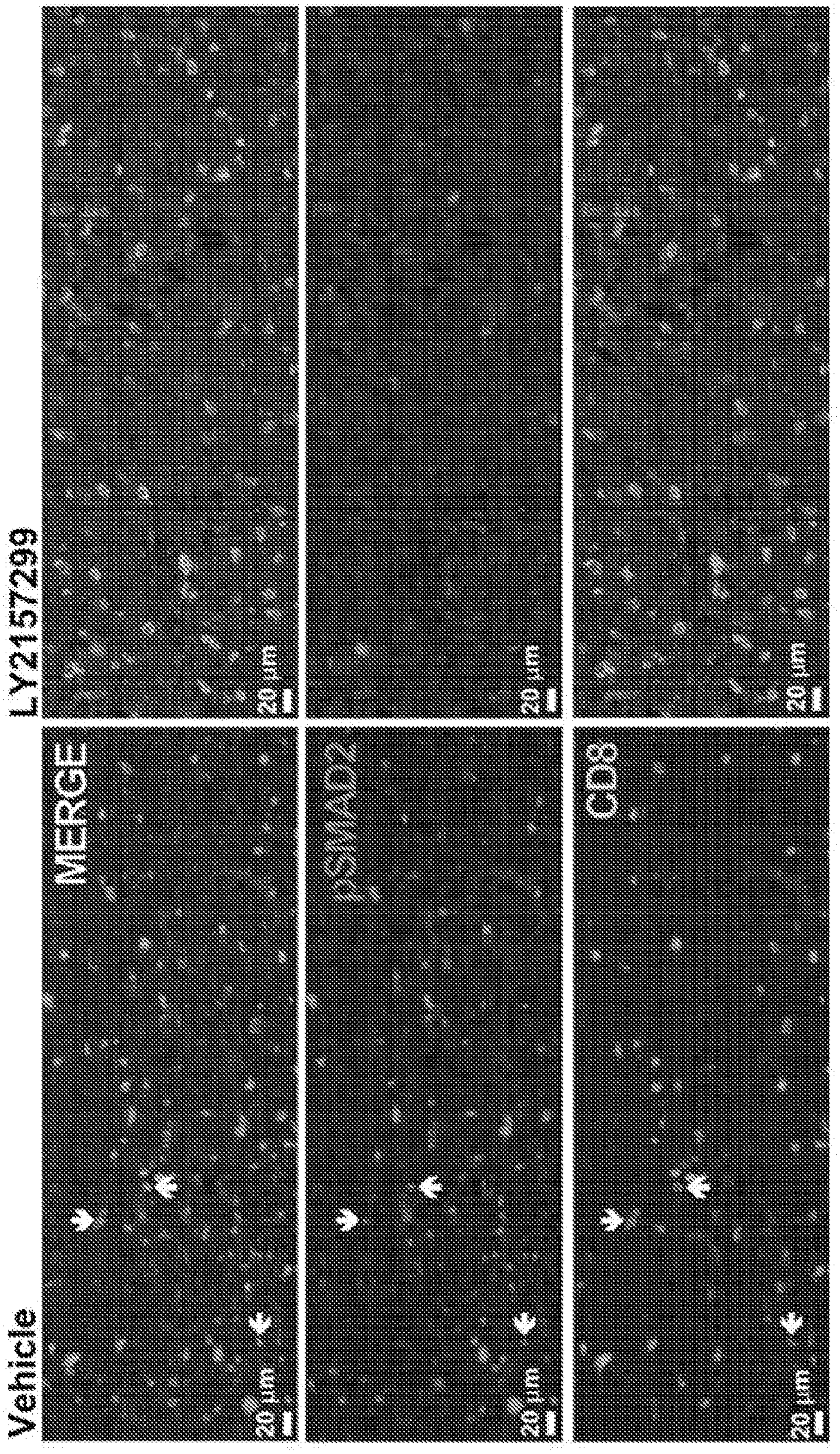
Figure 1D:
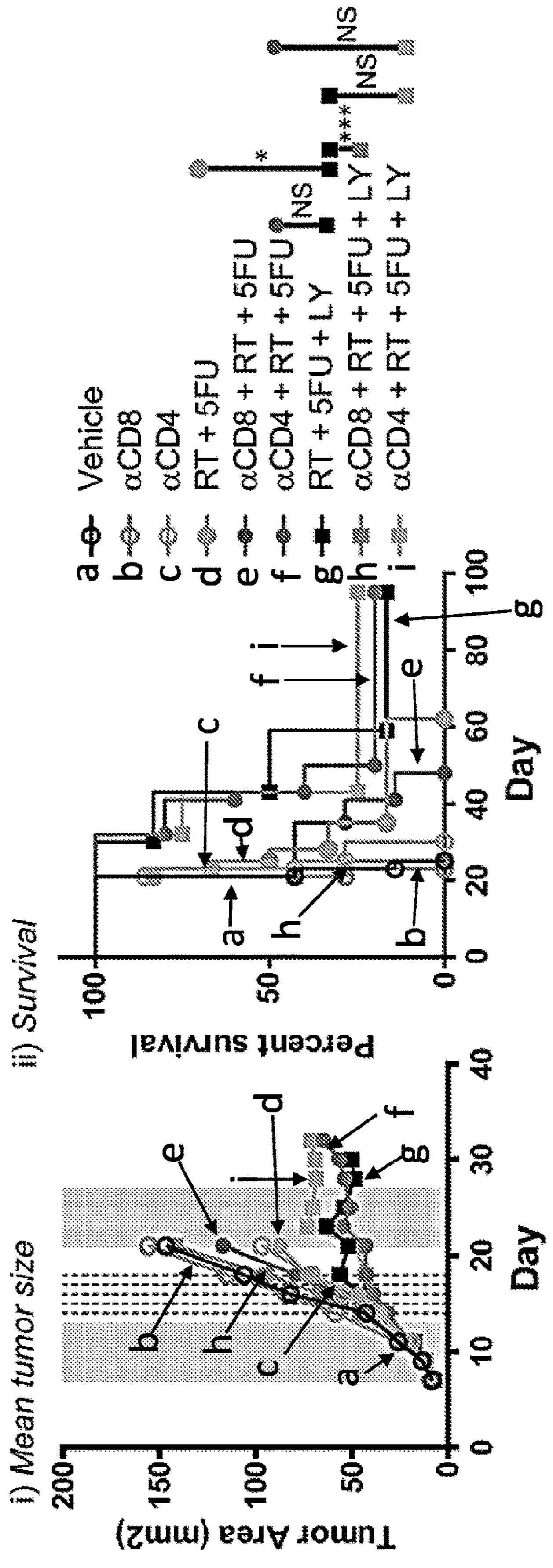

Evaluation of tumor sections harvested from mice at day 14 (one day post-LY treatment) demonstrated reduced phosphorylation and nuclear translocation of the TGFβ signaling mediator, Smad2, indicating ALK5 signaling was attenuated in tumor tissue, specifically in the $CD8\alpha^+$ cells (FIG. 1C). The slight improvement in tumor control with $CD4^+$ T cell depletion (FIG. 1D) suggests that $CD4^+$ T regulatory cells (Treg) may also be a target of LY leading to less inhibition of $CD8\alpha^+$ T cells, or may be a major source of the TGFβ that inhibits $CD8\alpha^+$ T cells, such that CD4-depletion abrogates the immunosuppressive effects of these cell types. Production of TGFβ by cells within the tumor was evaluated. Tregs, which expressed the highest baseline levels of latent TGFβ1/LAP protein, also increased in frequency following RT (FIG. 2A-B); however, TGFβ was expressed by all cell types. Neutrophils and macrophages significantly increased TGFβ production following radiation consistent with their role in wound healing and phagocytosis following tumor cell apoptosis (FIG. 2A) (Xiao et al., *J. Immunol.* 181:3575-3585, 2008; Madeddu et al., *Circulation* 103:41-50, 2001).

Example 3

$CD8\alpha^+$ T Cells are the Direct Target of TGFβ Inhibitor

Figure 3A:
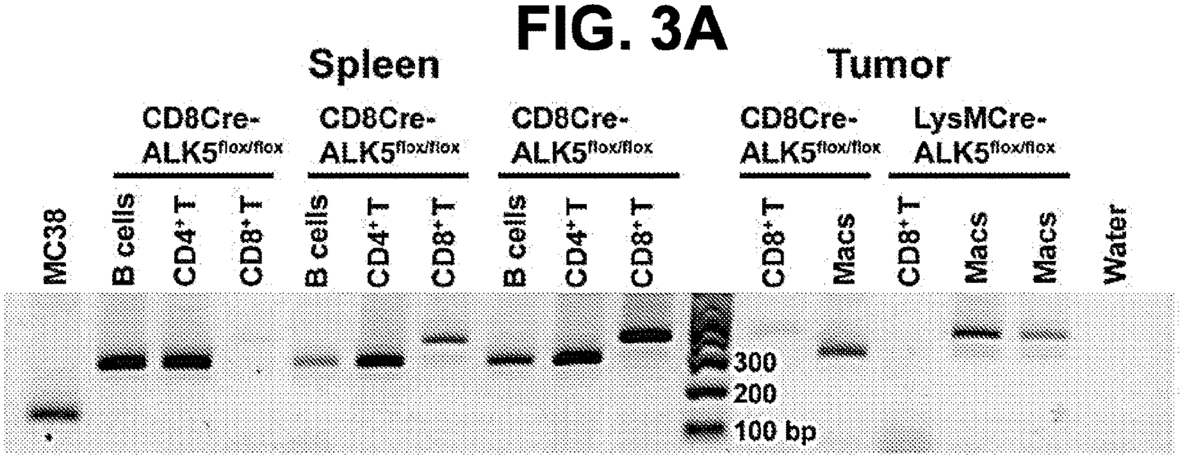
FIGS. 3A-3C illustrate cell-type specific ALK5 gene excision following conditional Cre expression. PCR analysis of ALK5 gene regions following cell sorting for CD19$^+$ B cells, CD4$^+$ T cells, CD8$^+$ T cells and macrophages in spleens and MC38 tumors in CD8Cre-ALK5$^{flox/flox}$ (n=3) and Lyz2Cre-ALK5$^{flox/flox}$ mice (n=2) (FIG. 3A). DNA from MC38 tumor cells and water blank are negative controls.
Figure 3B:
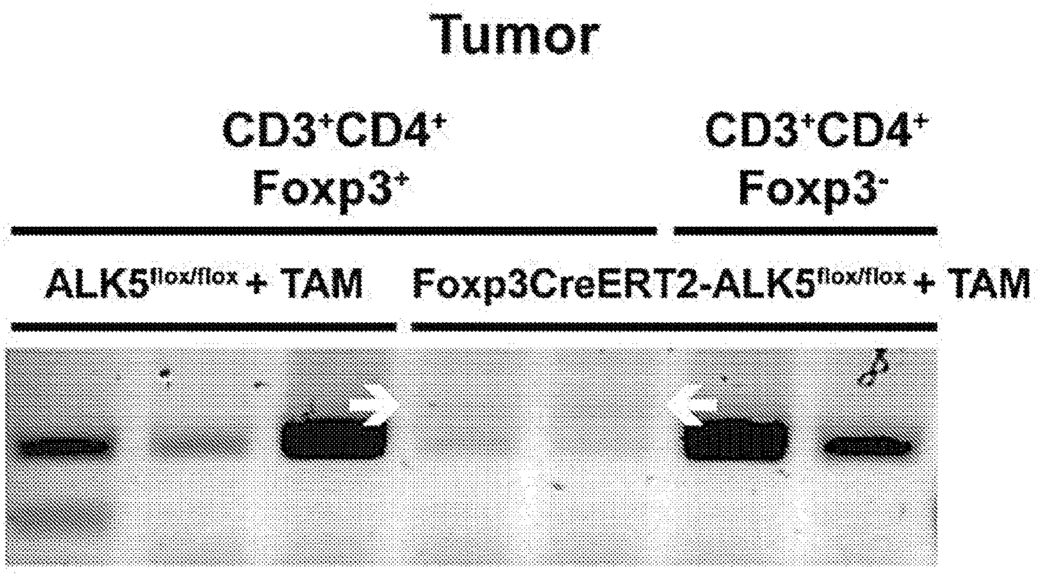
Figure 4A:
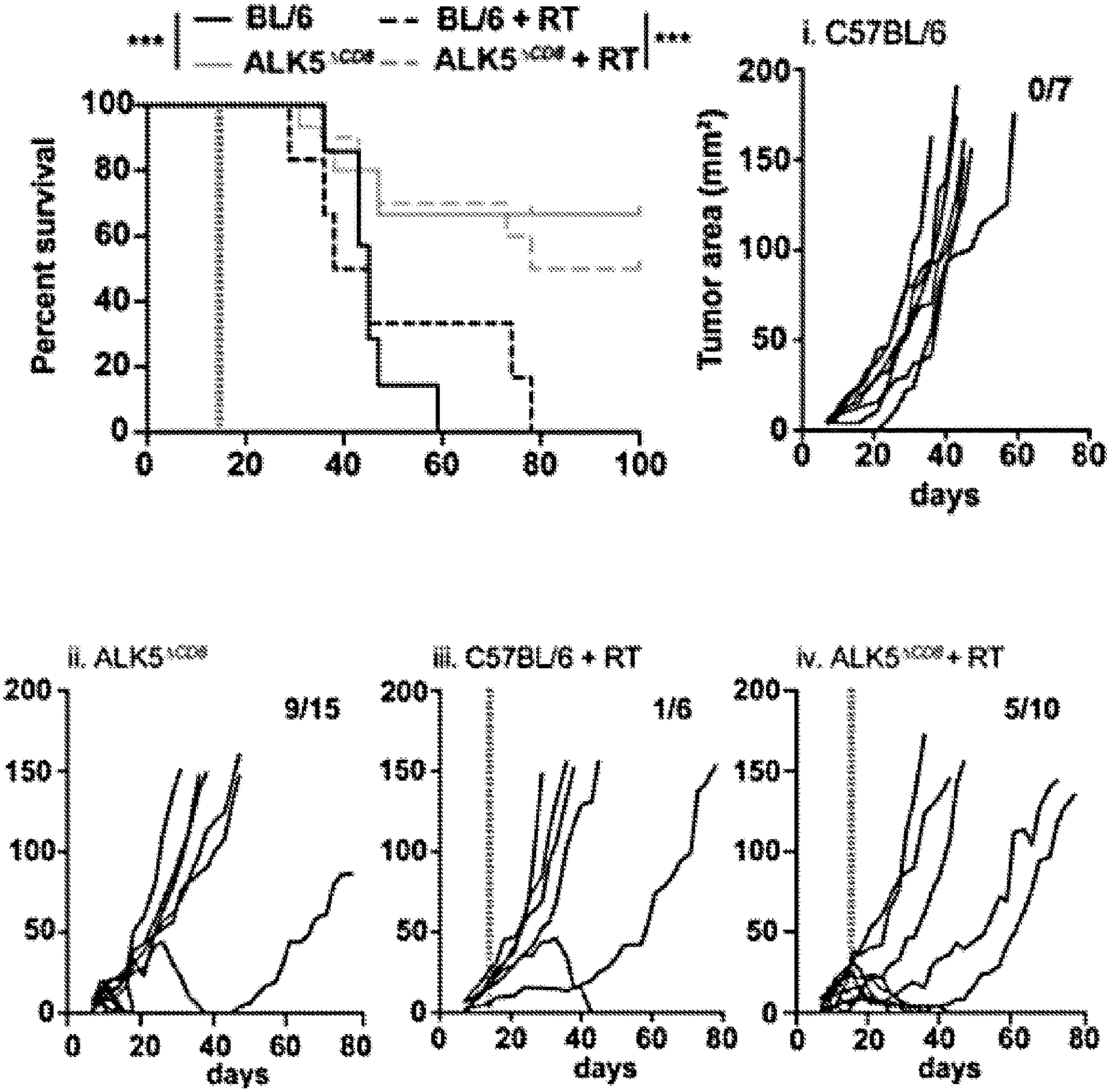
FIGS. 4A-4C demonstrate that CD8α-expressing cells are a direct target for TGFβR1 mediated immune suppression in rectal cancer mouse models.

To clarify further the primary target of LY2157299, the Cre-Lox system was utilized to generate double transgenic mice via cell-type specific Cre expression. Lyz2-Cre (Clausen et al., *Transgenic Res.* 8:265-277, 1999) (monocytes/macrophages), Foxp3-CreERT2-eGFP (Rubtsov et al., *Science* 329:1667-1671, 2010) (regulatory T cells), and CD8α-Cre (Maekawa et al., *Nat. Immunol.* 9:1140-1147, 2008) ($CD8\alpha^+$ T cells) animals were crossed with $ALK5^{flox/flox}$ mice (Larsson et al., *EMBO J.* 20:1663-1673, 2001) to excise exon 3 of the ALK5 gene. Double transgenic mice demonstrated specific ALK5 excision by PCR evaluation of flow cytometry isolated immune cells from tumors and spleens (FIGS. 3A-3B). These animals were subsequently challenged with syngeneic colorectal MC38 tumors, as all transgenic animals shared the C57BL/6 background. Tumors took uniformly in $ALK5^{\Delta Lyz2}$ animals, and tumor growth and survival were similar to C57BL/6J controls (FIG. 4C). There was a non-significant increase in cured animals following radiation in the $ALK5^{\Delta Lyz2}$ animals compared to control (0% vs 20% cure rate, p=0.2 by Fischer's exact).

Figure 3C:
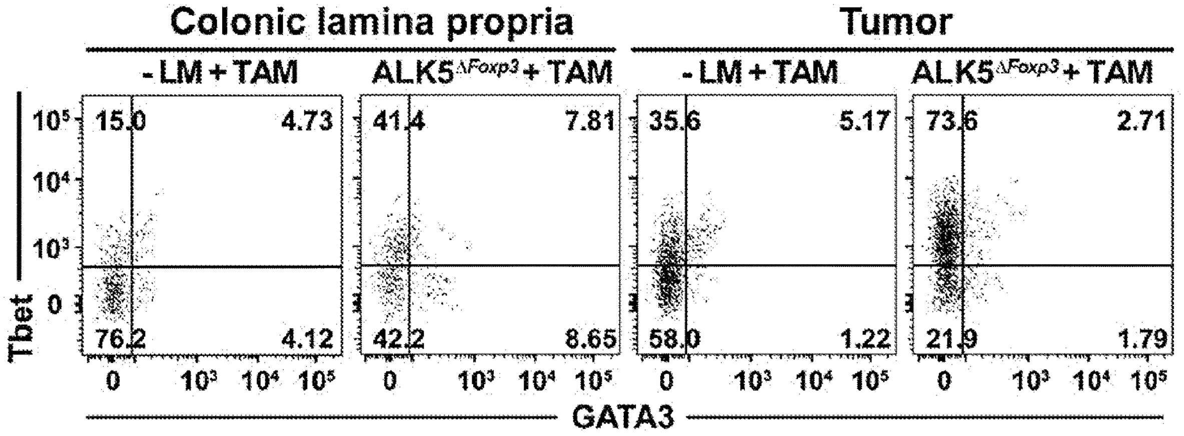
Figure 4B:
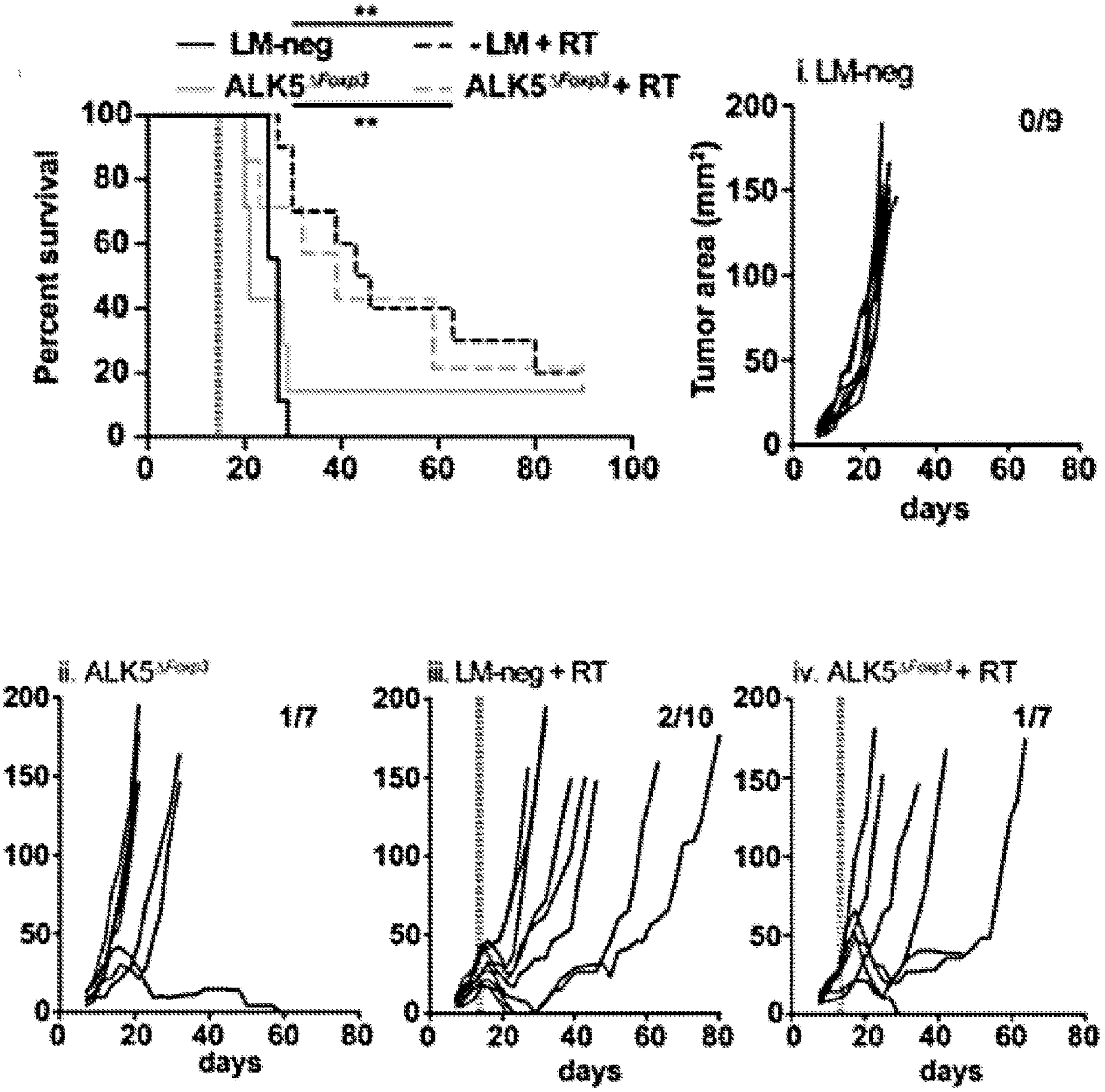
Figure 4C:
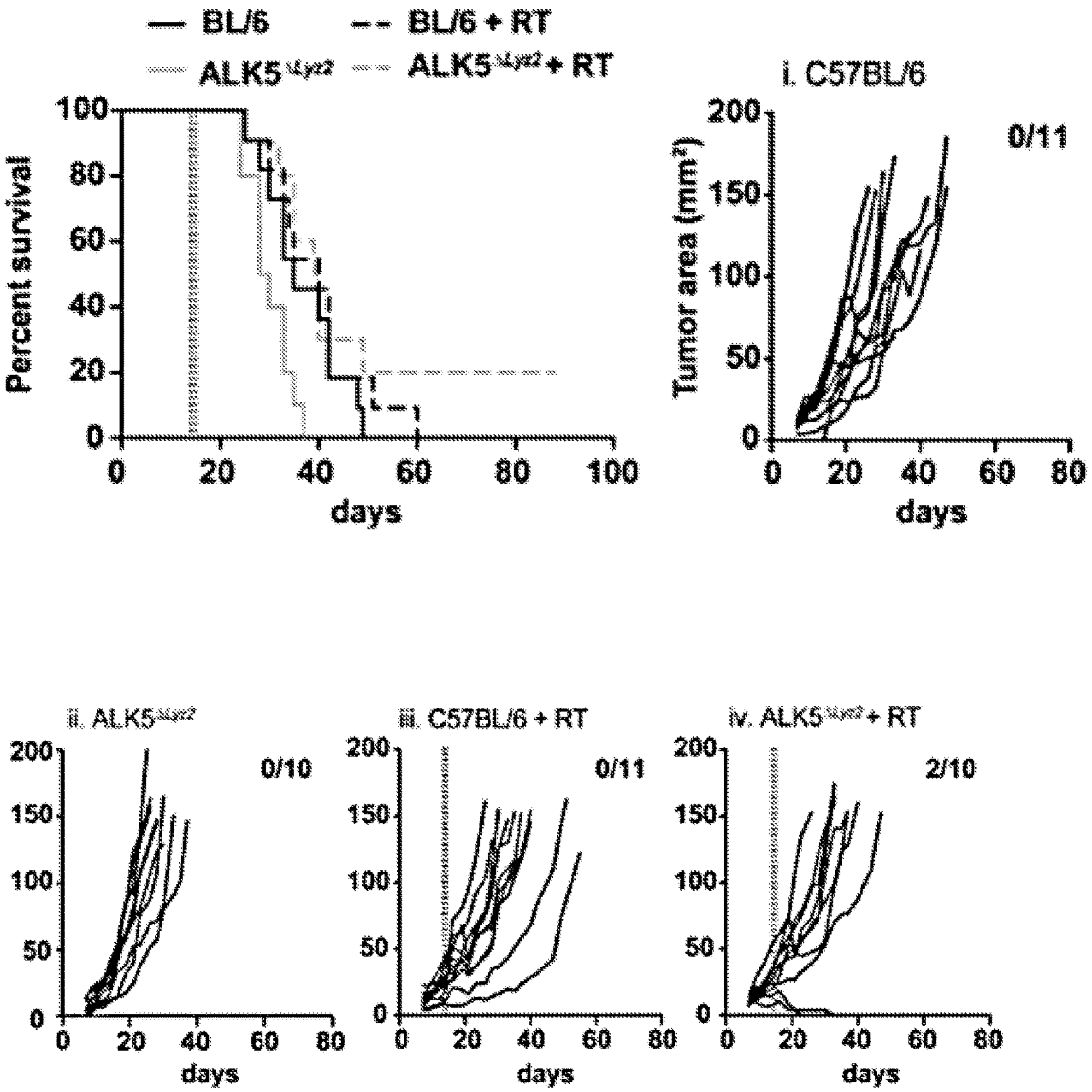

Surprisingly, there was more rapid tumor growth in $ALK5^{\Delta Foxp3}$ animals (31 vs 55 $mm^2$ at day 16, p<0.05, FIG. 4B(v)), but no difference in survival or radiation response (FIG. 4B). A previous publication utilizing the $ALK5^{\Delta Foxp3}$ mice found $FoxP3^+$ Tregs of the colonic lamina propria were better able to suppress $CD8^+$ T cell IFN-γ production when ALK5 was lost due to enhanced Treg expression of the transcription factor Tbet (Konkel et al., *Immunity* 46:660-674, 2017). Therefore, to determine if tumor infiltrating Tregs harbored a similar, more suppressive phenotype, regulatory T cell Tbet expression in MC38 tumors was evaluated. More tumor-infiltrating $Foxp3^+$ Tregs expressed Tbet in $ALK5^{\Delta Foxp3}$ mice compared to littermate control (LM) (FIG. 3C), suggesting a more suppressive regulatory T cell phenotype in $ALK5^{\Delta Foxp3}$ mice may be contributing to the more rapid tumor growth.

Figure 2A:
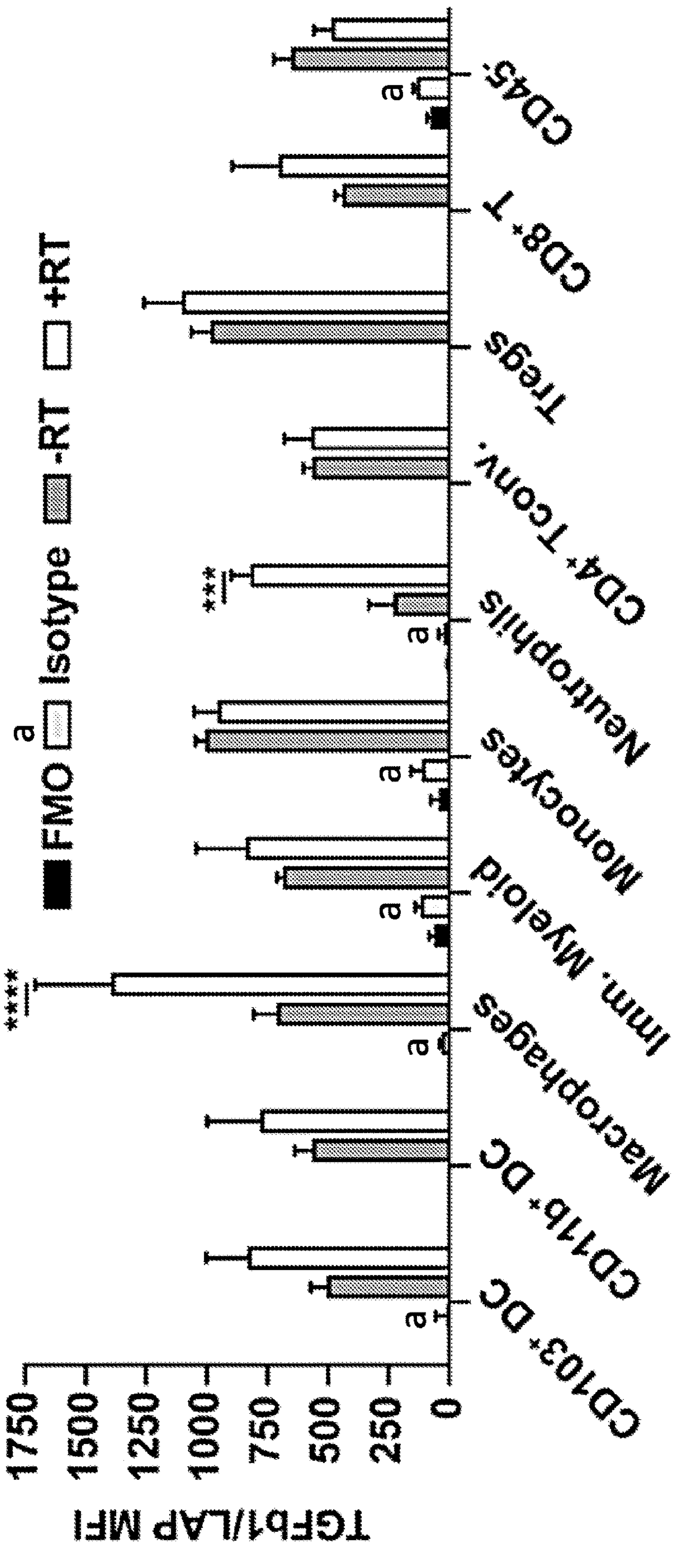
FIGS. 2A and 2B show that TGFβ1 is highly expressed in tumor Tregs which are increased following radiation therapy (RT). Intracellular TGFβ1/LAP expression was determined by FACS analysis of MC38 tumors 21 days post implant from untreated mice and mice treated with RT at 10 Gy×2 on days 14 and 15 (FIG. 2A). Cells were gated on the indicated populations and average TGFβ1/LAP MFI calculated in each subset. The frequency of CD3$^+$CD4$^+$Foxp3$^+$ Tregs in MC38 tumors was determined by FACS analysis 7 days following +/−RT at 10 Gy×2 (FIG. 2B). Shown is one experiment reflective of two independent experiments. *=p<0.001, ** p<0.0001. Error bars in each subpanel are standard deviations.
Figure 2B:
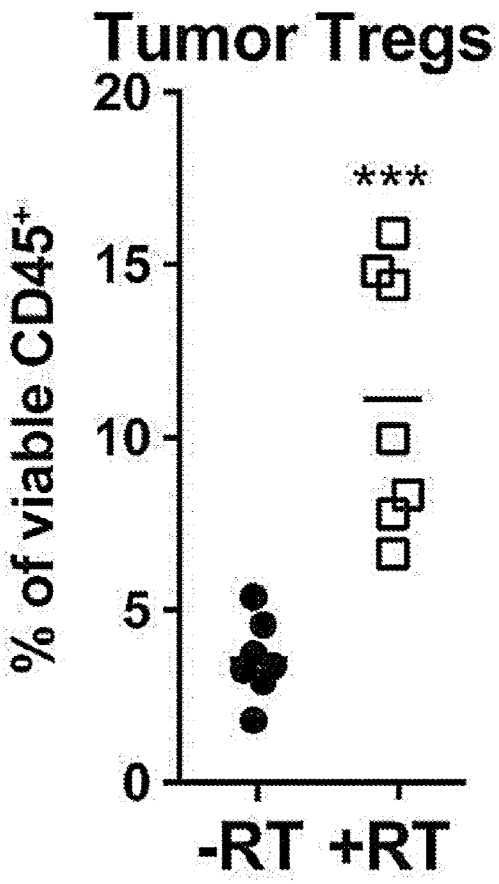

MC38 tumors grew to comparable sizes by 10-14 days post implant in $ALK5^{\Delta CD8}$ and wildtype (WT) animals (FIG. 4A), however, tumors were subsequently rejected in >60% of $ALK5^{\Delta CD8}$ transgenic animals (FIG. 4A). This translated to improved survival of $ALK5^{\Delta CD8}$ mice (median survival not reached vs 45 days in WT mice, $p<0.01$, FIG. 4C). Whether the effects of radiation were different in WT vs ALK5$^{\Delta CD8}$ mice was next tested. When mice were randomized at day 14 to receive radiation, all tumors in ALK5$^{\Delta CD8}$ mice were eradicated (data not shown), but it was difficult to determine whether that was due to radiation, or whether those tumors would have been rejected regardless. Therefore, in order to better assess response to radiation, animals whose tumors were not rejected were selected, presumably a more aggressive, immunosuppressed phenotype. Hypofractionated radiation (10 Gy×2) significantly improved survival of ALK5$^{\Delta CD8}$ animals compared to control (median survival 89d vs 41.5d, $p<0.05$, FIG. 2A). In addition, a non-significant increase in cure rates among ALK5$^{\Delta CD8}$ animals receiving radiation was observed, 50% versus 13.6% in WT mice (FIG. 2A, p=0.18 by $\chi^2$). Thus, CD8α-specific loss of ALK5 results in high rates of tumor rejection, improved survival, and enhanced response to radiation.

Figure 5A:
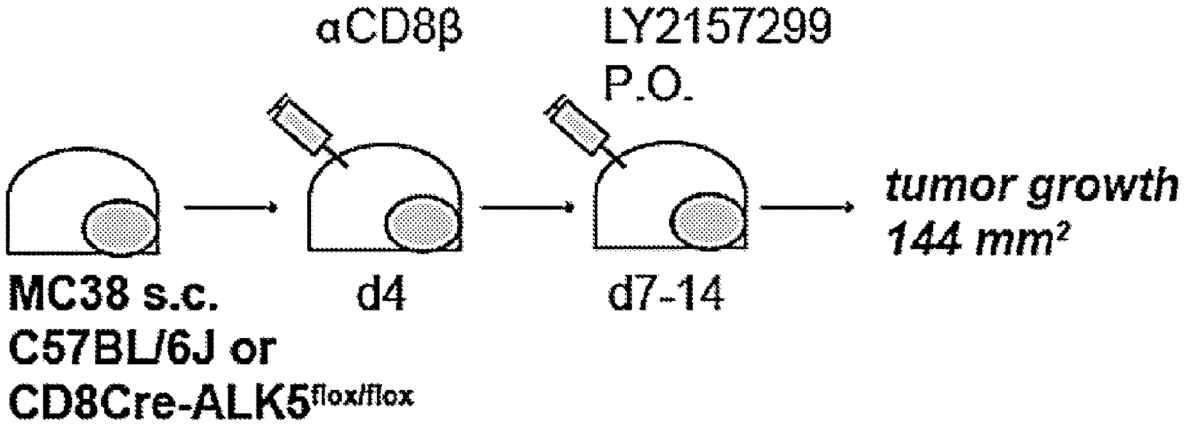
FIGS. 5A-5C show that tumor control in ALK5$^{\Delta CD8}$ mice is CD8$^+$ T cell dependent and LY2157299 preferentially targets ALK5 in CD8$^+$ T cells.
Figure 5B:
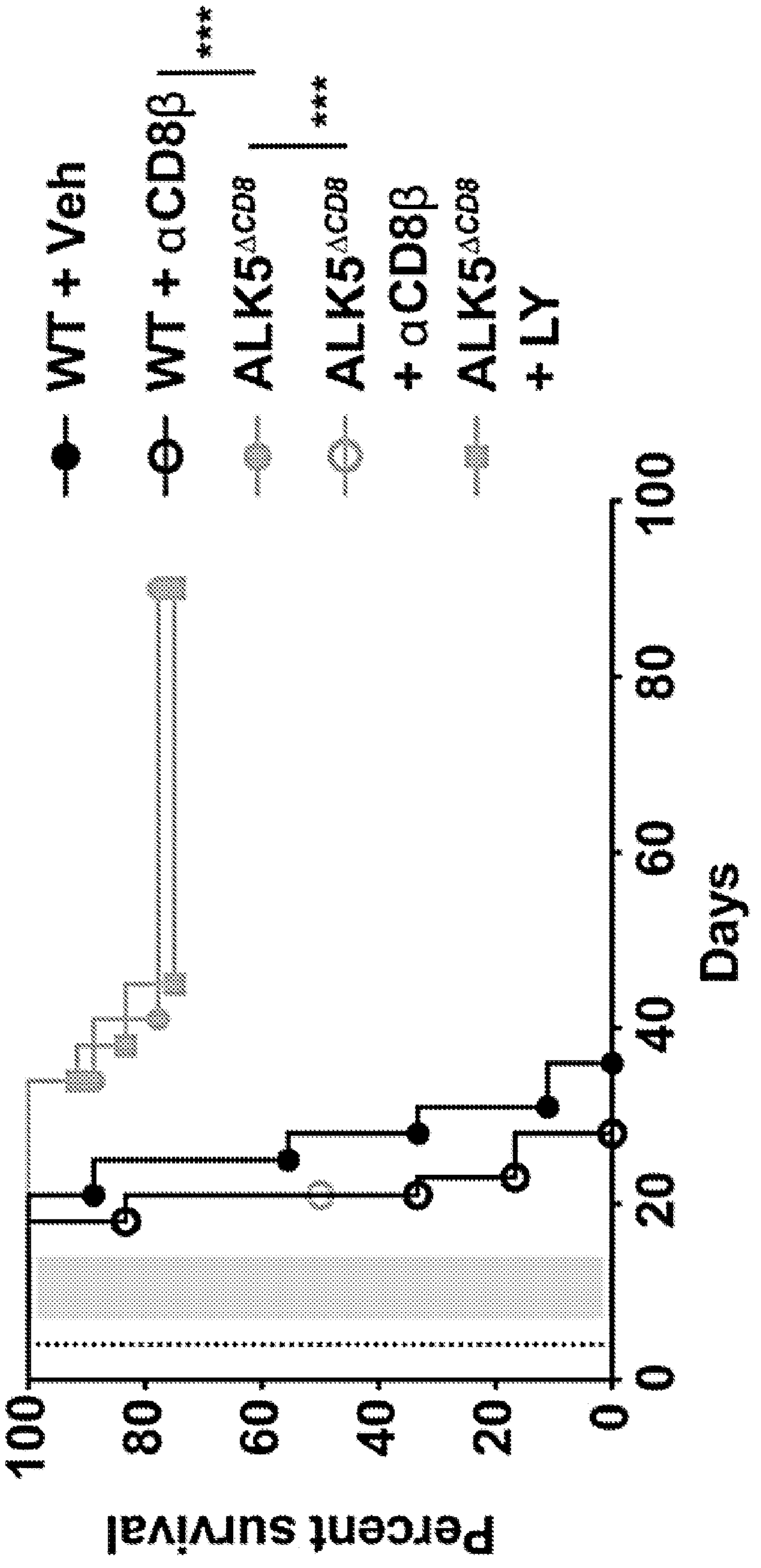
Figure 5C:
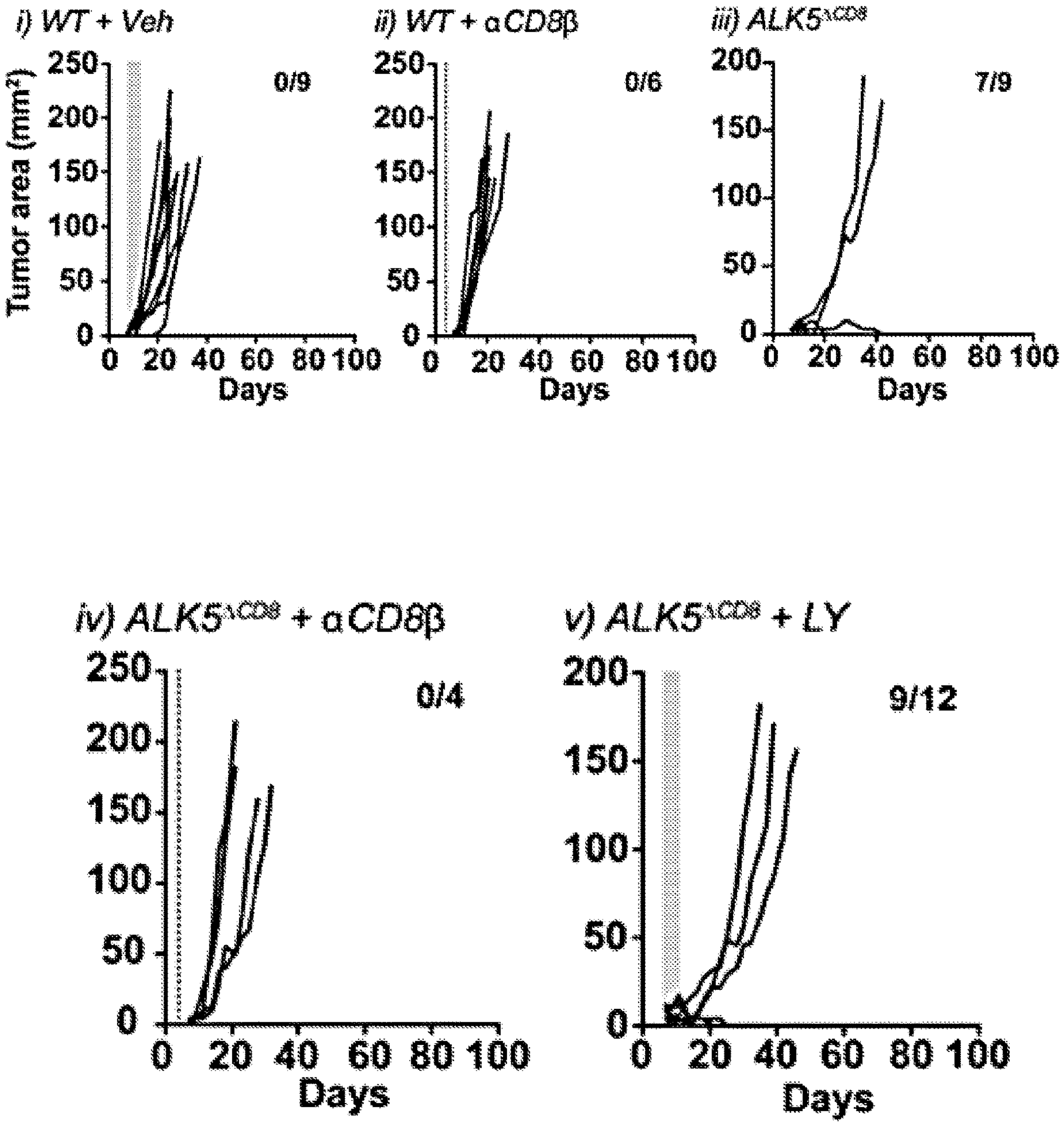
Figure 6A:
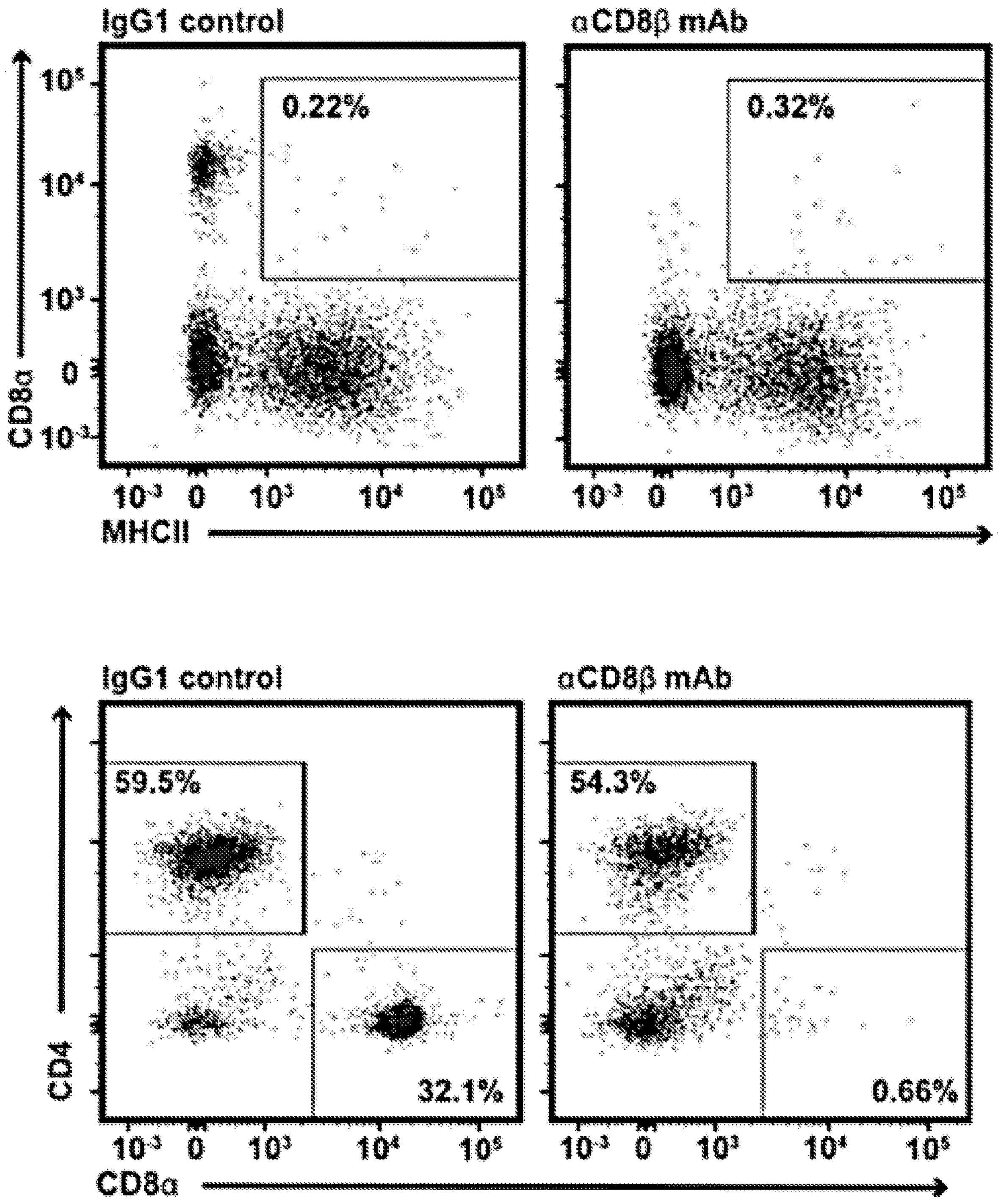
FIGS. 6A-6D are a series of panels showing generation of tumor-specific immune memory following tumor eradication with TGFβ inhibition with chemoradiation.

Whether the improved survival and radiosensitivity observed in ALK5$^{\Delta CD8}$ mice was dependent on CD8$^+$ T cells was next evaluated. MC38 tumor-bearing mice were treated with an anti-CD8β antibody on day 4 (FIG. 5A), which depletes CD8$^+$ T cells, but not CD8α-expressing dendritic cells (FIG. 6A). ALK5$^{\Delta CD8}$ mice treated with anti-CD8β grew tumors with similar kinetics and survival as wildtype control mice (median survival 24.5d versus 28d, p=0.24, FIGS. 5B and 5C). These data demonstrate that CD8$^+$ T cells are necessary for the improved survival and tumor rejection observed in ALK5$^{\Delta CD8}$ mice.

Figure 6B:
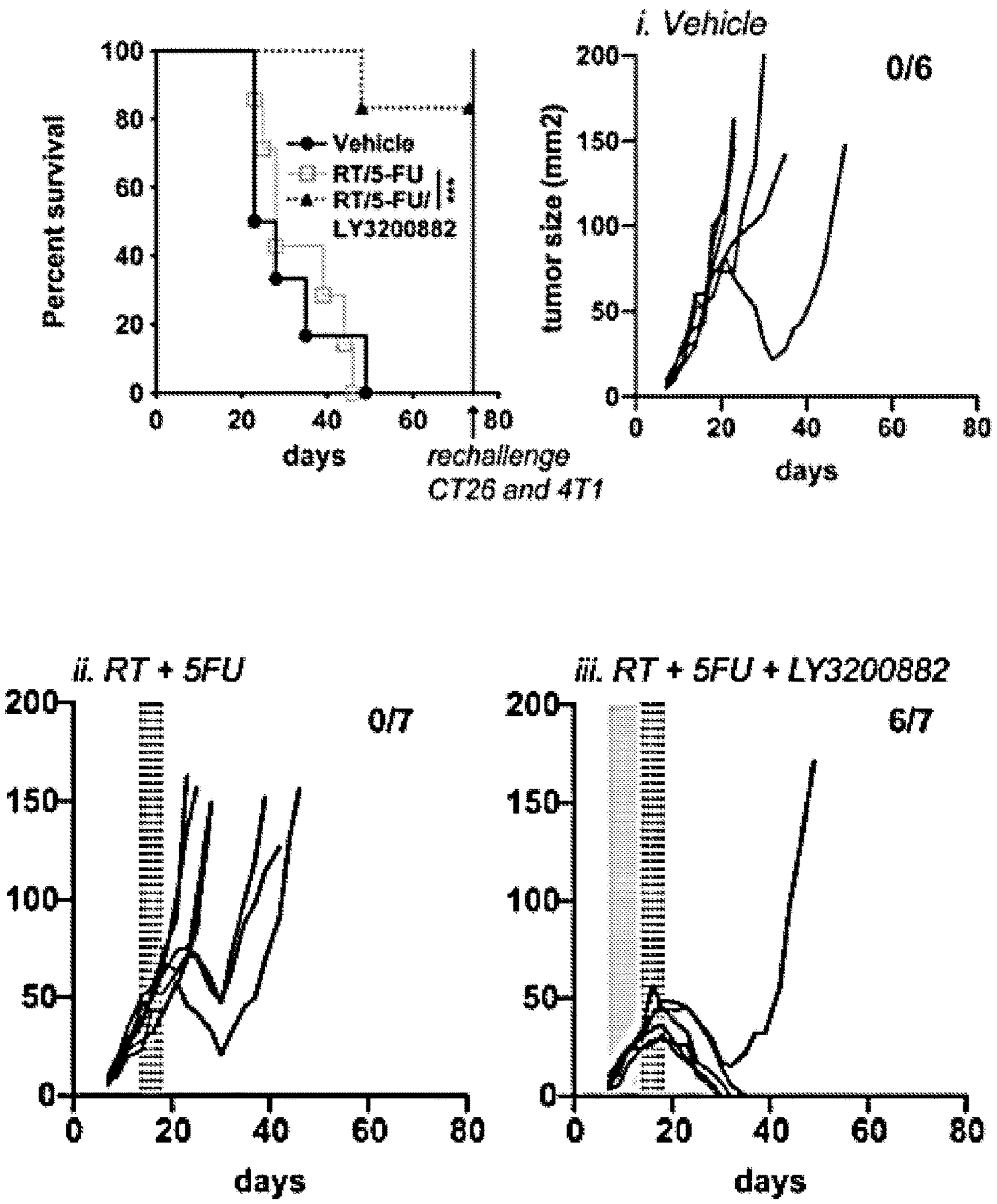
Figure 6C:
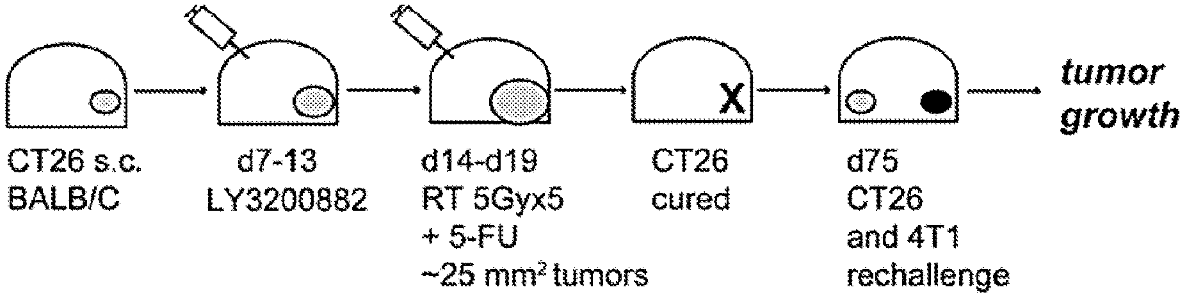
Figure 6D:
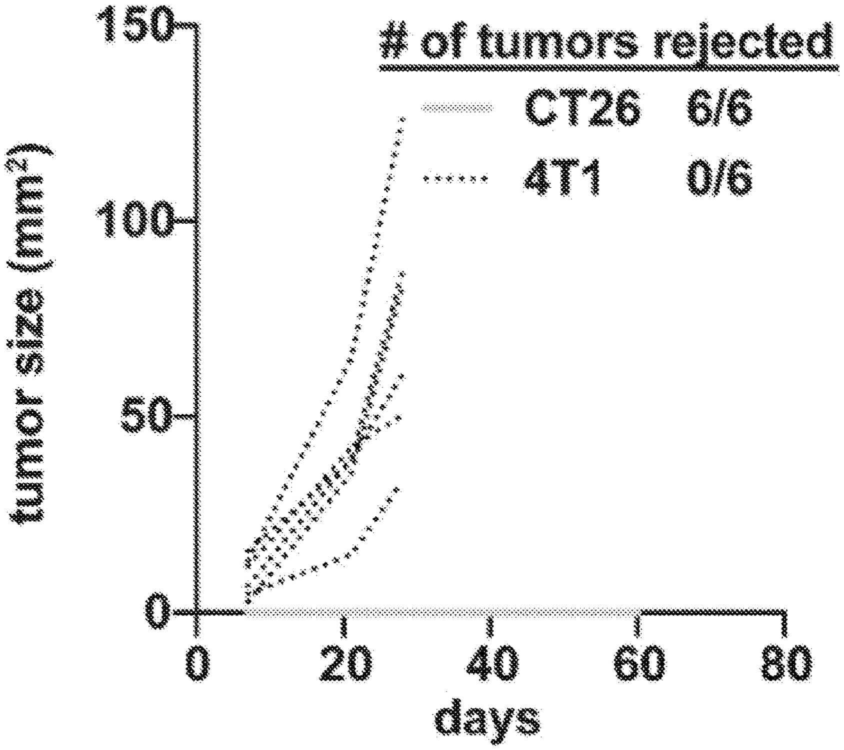

In order to evaluate whether the improved efficacy of RT+5FU+LY (FIG. 1B) was due to the direct effect of ALK5 inhibition on CD8$^+$ T cells, LY treatment in ALK5$^{\Delta CD8}$ mice was tested. There was no improvement in survival or tumor growth kinetics with the addition of LY2157299 (FIGS. 5B and 5C). These data suggest the primary target of LY2157299 is directly on CD8$^+$ T cells, via inhibition of ALK5. This is significant, as it has been reported that LY2157299 has a lower Kd for ALK4 than ALK5, raising the possibility that bone morphogenic protein (BMP) signaling through ALK4 may have been contributing to the efficacy observed with RT+5FU+LY therapy (Lahn et al., *Drug Des. Devel. Ther.* 9:4479, 2015). To further demonstrate that ALK5 inhibition is the primary mechanism for efficacy, a more selective second generation ALK5 inhibitor, LY3200882 (Pei et al., *Cancer Res.* 77:955, 2017) was tested. Using this more potent ALK5 inhibitor with chemoradiation, greater efficacy was observed than was seen with LY2157299, achieving tumor cures in 6 of 7 animals (median survival not reached vs 28d RT+5FU, $p<0.001$, FIG. 6B). Further, cured animals rejected tumor rechallenge at day 73 post-implant with CT26 cells but not the immunologically distinct 4T1 cell line implanted simultaneously on the opposite flank (FIG. 6C-D), demonstrating the generation of tumor-specific immune memory. Together, these data demonstrate that LY2157299 acts primarily via ALK5 inhibition of CD8$^+$ T cells.

Example 4

Figure 7A:
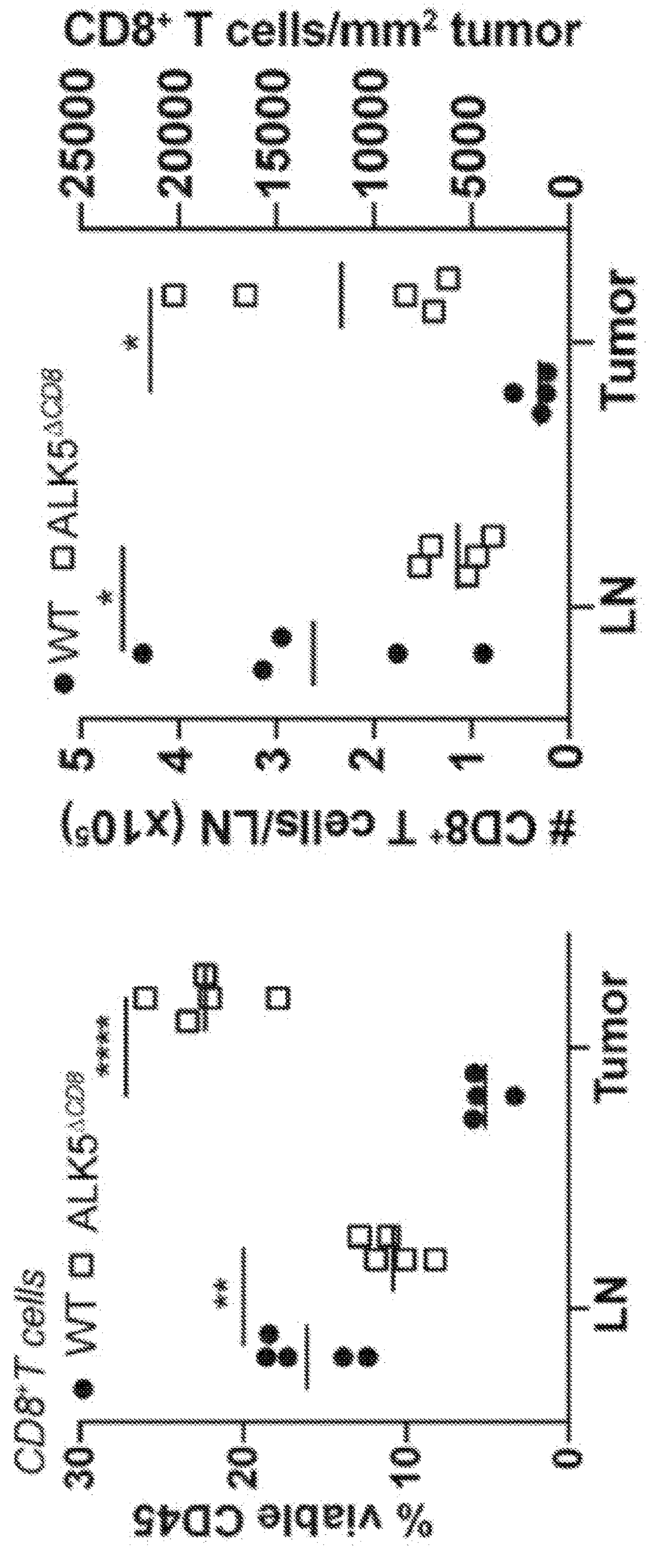
FIGS. 7A-7H are a series of panels showing ALK5 loss lowers the TCR activation threshold and enhances effector function of $CD8^+$ T cells. On day 14 following MC38 implantation into WT (n=6) and $ALK5^{\Delta CD8}$ (n=7) mice, tumors were harvested and digested into a single cell suspension for analysis by flow cytometry. Each symbol is the value of an individual animal within each immune subset and displayed as the mean of each group.
Figure 7B:
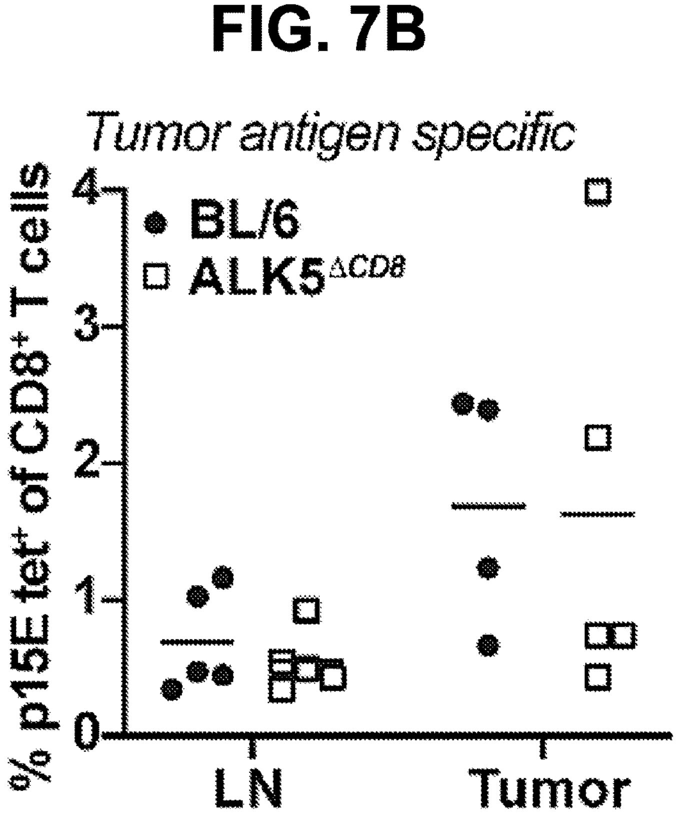
Figure 7C:
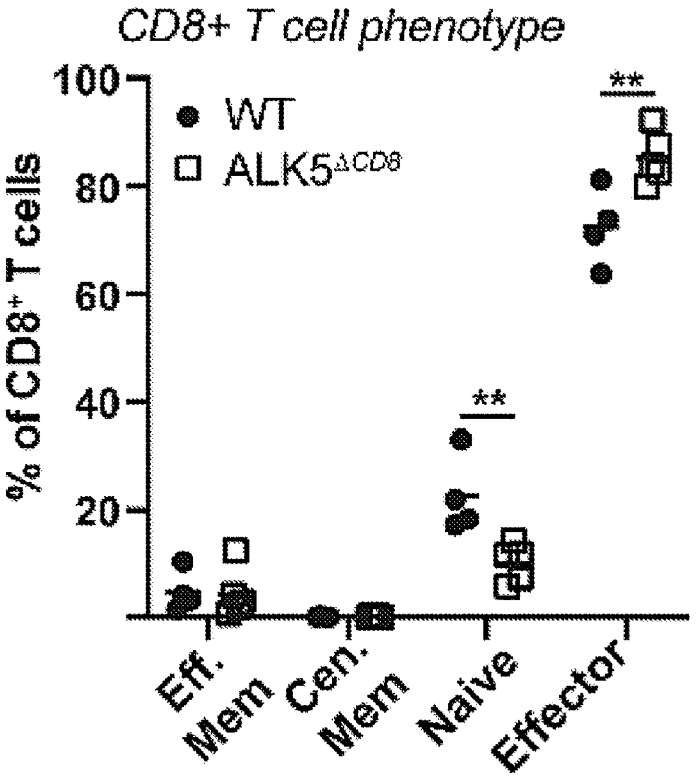
Figure 7D:
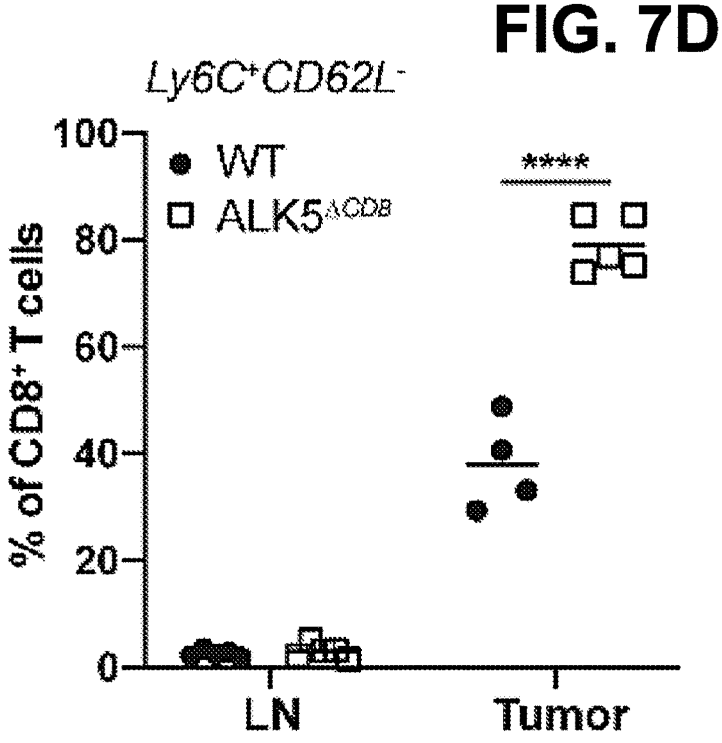
Figure 7E:
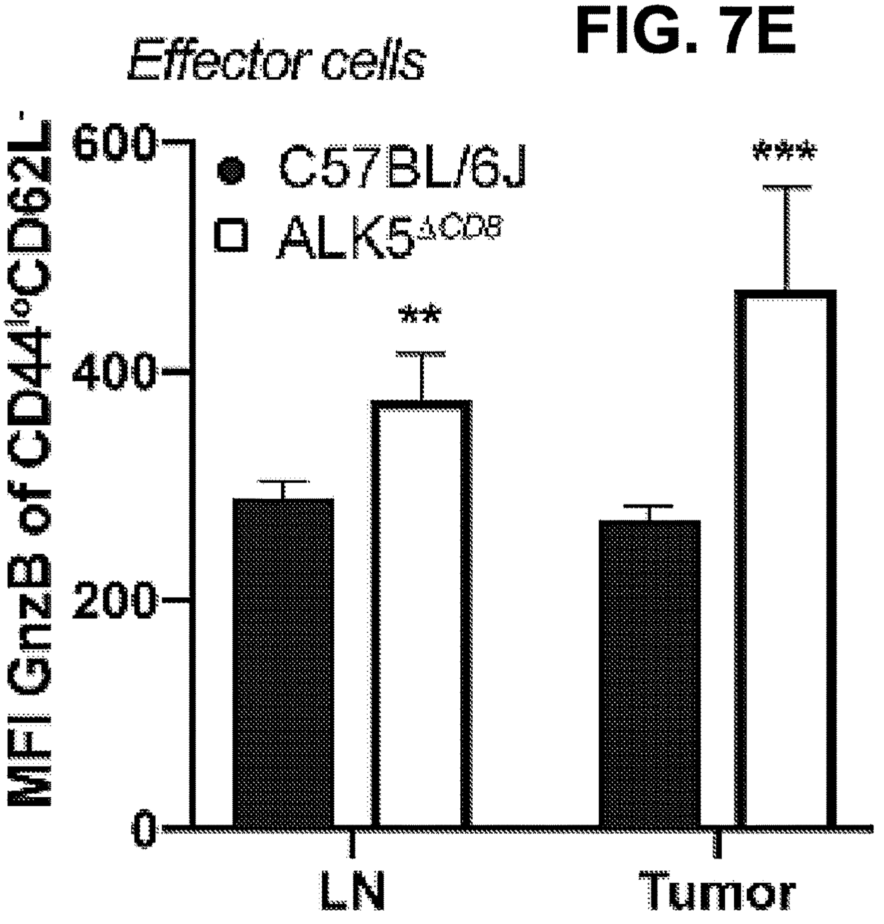
Figure 7F:
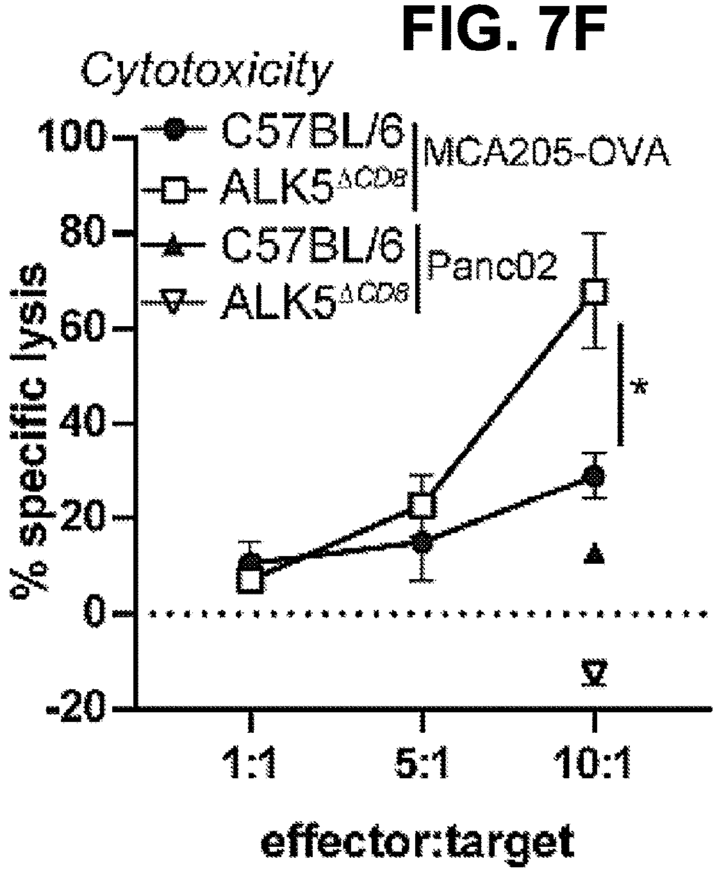
Figure 7G:
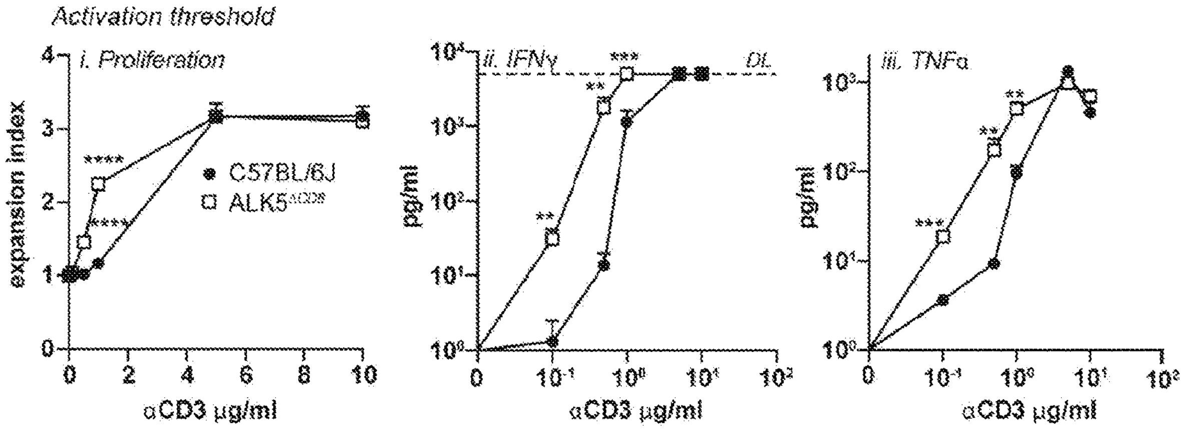
Figure 7H:
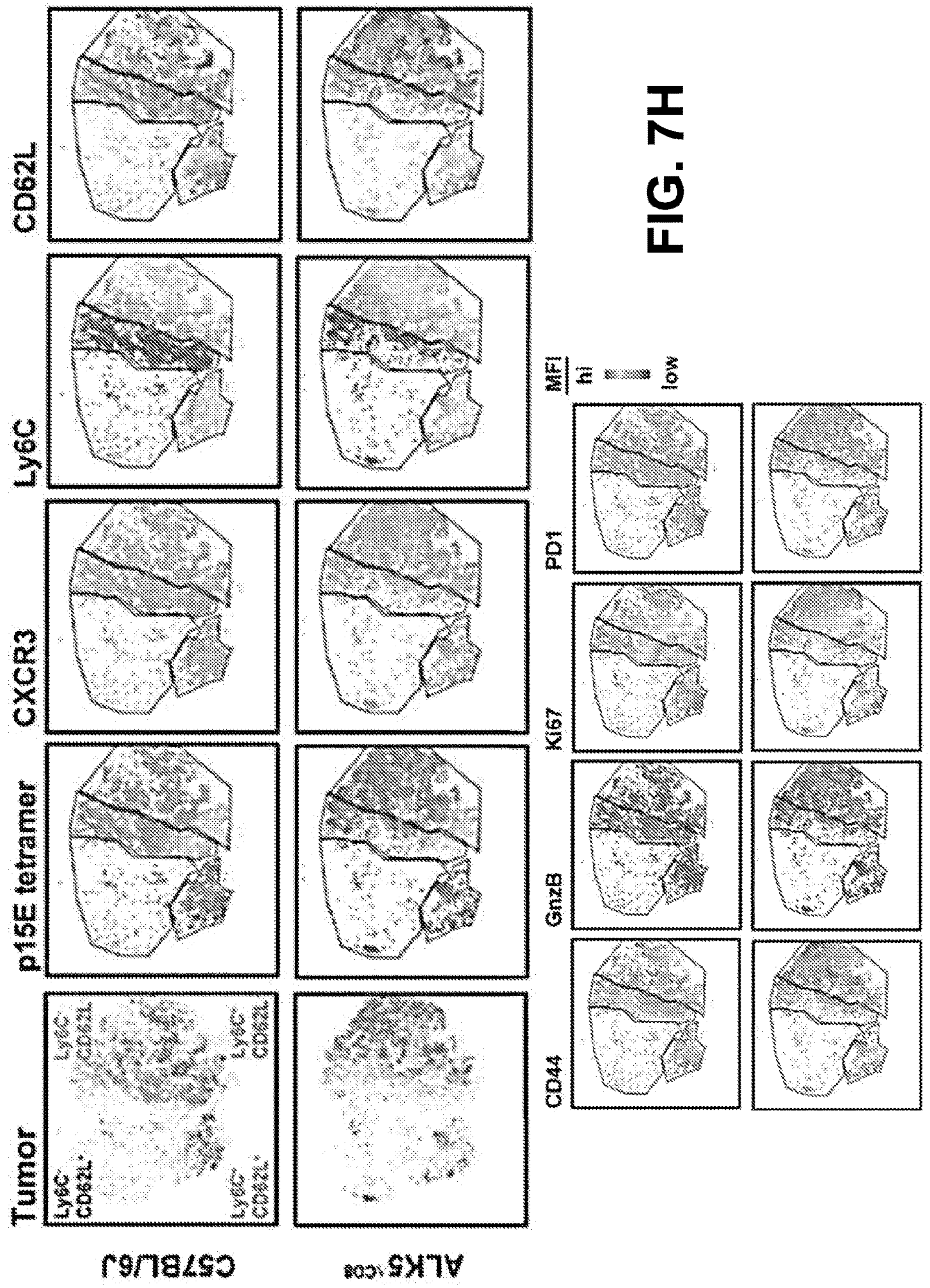
Figure 8A:
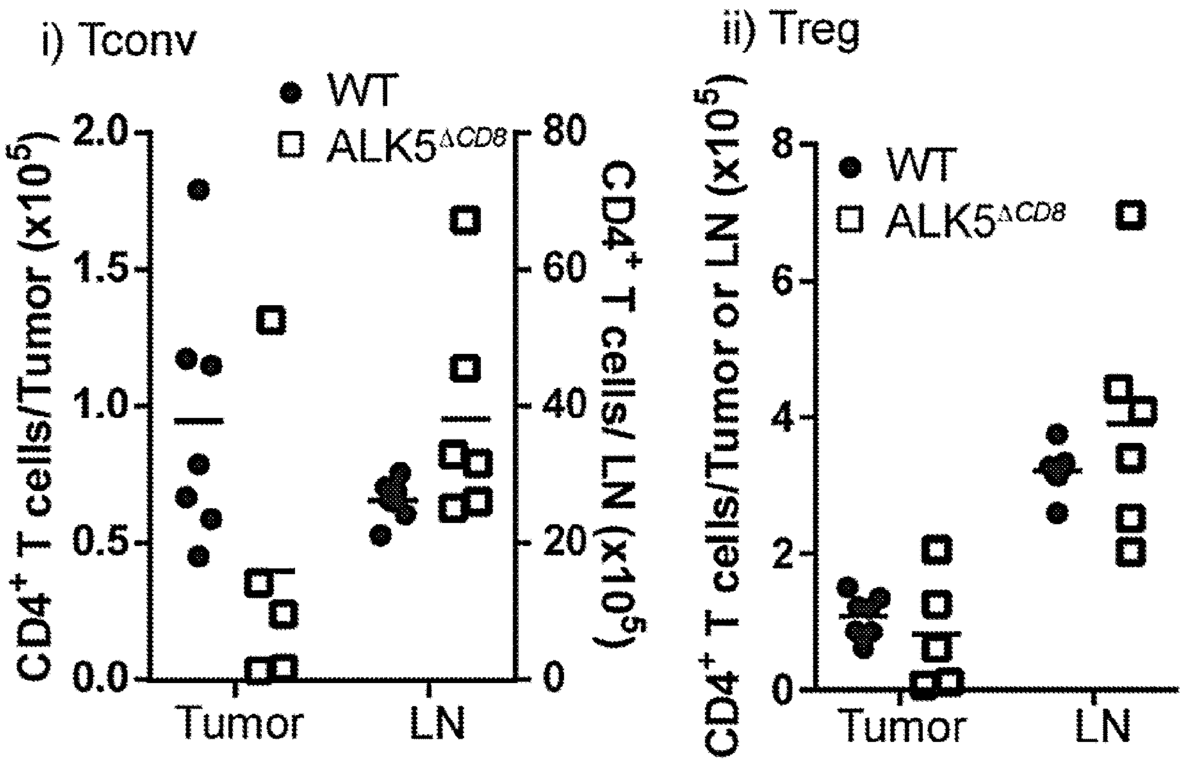
FIGS. 8A-8F are a series of panels demonstrating $CD8^+$ T cells deficient in TGFβ signaling alter the tumor microenvironment. FACS analysis of day 14 MC38 tumor digests from WT and $ALK5L^{\Delta CD8}$ mice. Shown in FIG. 8A are the absolute numbers of i) $CD4^+Foxp3^-$ T conventional cells and ii) $CD4^+Foxp3^+$ T regulatory cells in the tumor (left) and draining lymph node (right).
Figure 8B:
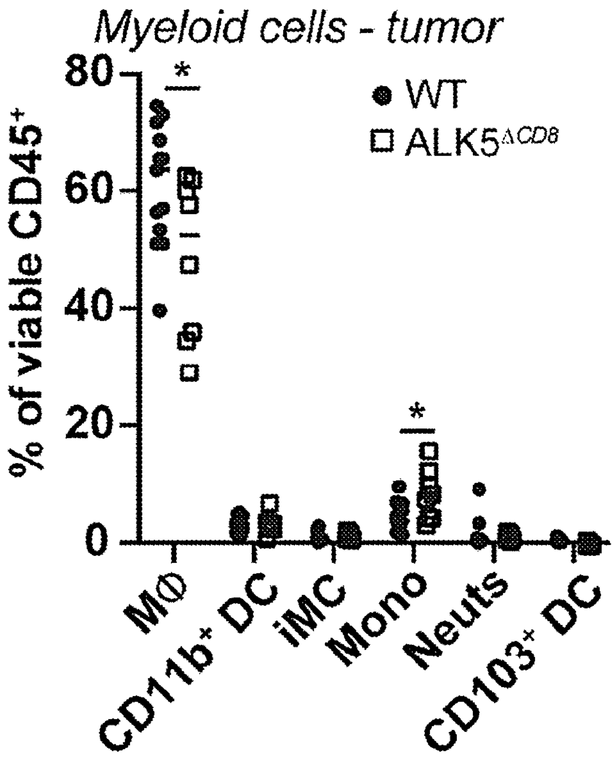

TGFβR1 Loss in CD8$^+$ T Cells Improves Cytotoxicity and Reduces Threshold for TCR Activation Next, the mechanism by which CD8 T cell-specific ALK5 loss improved anti-tumor immunity was evaluated. First, differences in immune cell populations in the periphery and the tumor microenvironment of ALK5$^{\Delta CD8}$ mice was evaluated. Flow cytometric evaluation of MC38 tumors derived from ALK5$^{\Delta CD8}$ or WT mice at day 14 post implant (prior to rejection) was performed. An increase in total CD8$^+$ T cells in tumors and a corresponding decrease in CD8$^+$ T cells in tumor draining lymph nodes from ALK5$^{\Delta CD8}$ mice (FIG. 7A) was observed. However, no difference was observed in the percentage of CD8$^+$ T cells reactive against the MC38 trackable antigen p15E (FIG. 7B). Whether CD8$^+$ T-cell subsets varied between tumors in ALK5$^{\Delta CD8}$ and WT animals was evaluated next. A decrease in tumor infiltrating naïve CD8$^+$ T cells and an increase in effector CD8$^+$ T cells as defined by CD44$^{low}$CD62L (FIG. 7C) or Ly6C$^+$CD62L$^-$ (FIG. 7D) phenotypes in ALK5$^{\Delta CD8}$ mice was observed. To determine whether ALK5 loss contributed to the development of a novel T cell subset or enriched an existing subset, a tSNE plot was generated from the flow cytometry staining markers (FIG. 7G). Using next-nearest neighbor clustering, an enrichment of the effector population without generation of a novel subset of tumor-infiltrating T cells (FIG. 7G) was observed. No significant differences were observed in CD4$^+$ T cells or T helper conventional and regulatory T cell subsets in tumors or lymph nodes (FIG. 8A). Macrophage frequency was reduced in tumors from ALK5$^{\Delta CD8}$ mice (FIG. 8B).

Figure 8C:
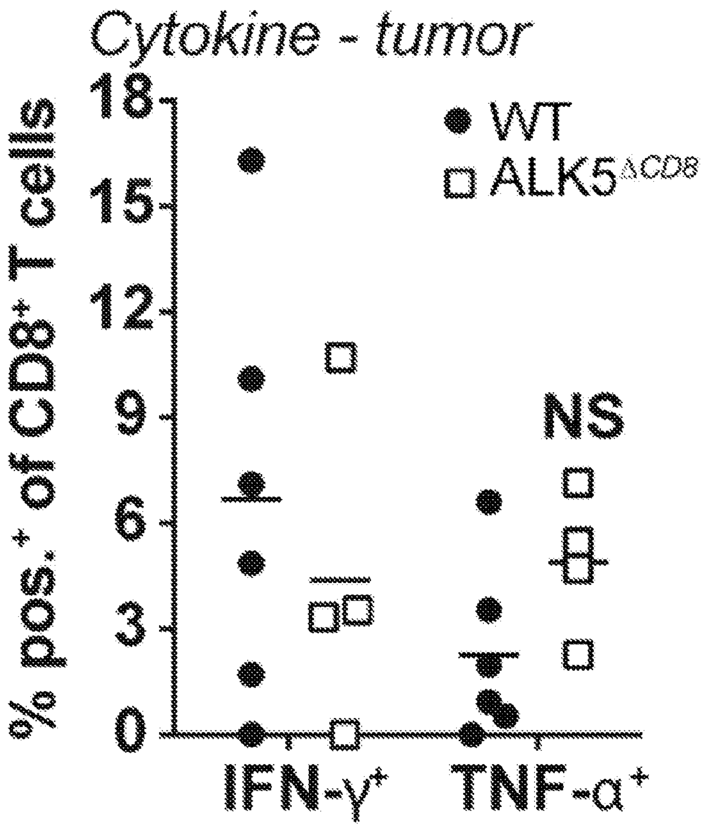

The function of infiltrating CD8$^+$ T cells in WT and ALK5$^{\Delta CD8}$ animals was then evaluated. The percent of tumor infiltrating CD8$^+$ cells that expressed IFN-γ or TNF-α were similar in ALK5$^{\Delta CD8}$ and WT mice (FIG. 8C). However, within the effector CD8$^+$ T cell subset, there was an increase in granzyme B expression (FIG. 7E), consistent with previous reports of TGFβ-mediated transcriptional suppression of granzyme (Thomas et al., *Cancer Cell* 8:369-380, 2005). Tumor-specific cytotoxicity of ALK5$^{\Delta CD8}$ and WT CD8$^+$ T cells ex vivo was subsequently tested. OVA-specific CD8$^+$ T cells were generated by vaccination with a replication deficient *L. monocytogenes*, engineered to express the ovalbumin peptide SIINFEKL (OVA; SEQ ID NO: 5). CD8$^+$ T cells were isolated from splenocytes and co-cultured at increasing ratios of effector to tumor cell, with an OVA-expressing tumor cell line (MCA205-OVA) or a control Panc02 tumor cell line, which does not express OVA (FIG. 7F) Enhanced tumor specific cytotoxicity of ALK5$^{\Delta CD8}$CD8$^+$ T cells compared to WT control, and no difference in non-specific cytotoxicity (FIG. 7F) was observed. ALK5 expression in CD4$^+$ T cells is regulated by TCR signal strength (Tu et al., *Immunity* 48:745-759.e6, 2018). Whether the reciprocal was true in CD8$^+$ T cells was therefore interrogated; whether ALK5 loss altered the threshold for TCR stimulation was tested. Splenocyte-derived, purified naïve CD8$^+$ T cells were cultured with a fixed concentration of αCD28 antibody and increasing amounts of plate-bound agonist αCD3 antibody (FIG. 7G). Increased proliferation and cytokine production of IFNγ and TNFα was observed at lower concentrations of αCD3 antibody suggesting that loss of ALK5 decreased the threshold for TCR-mediated CD8$^+$ T cell activation. These are the first data to indicate that TGFβ suppresses anti-tumor CD8$^+$ T cell function by raising the threshold for naïve T cell activation through TCR stimulation, resulting in decreased effector differentiation and cytotoxicity.

Figure 8D:
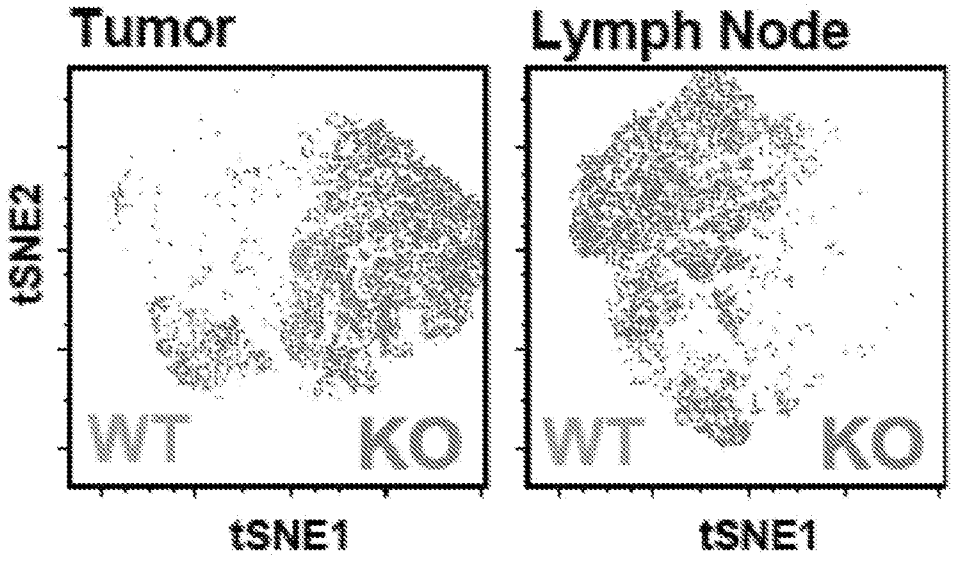
Figure 8E:
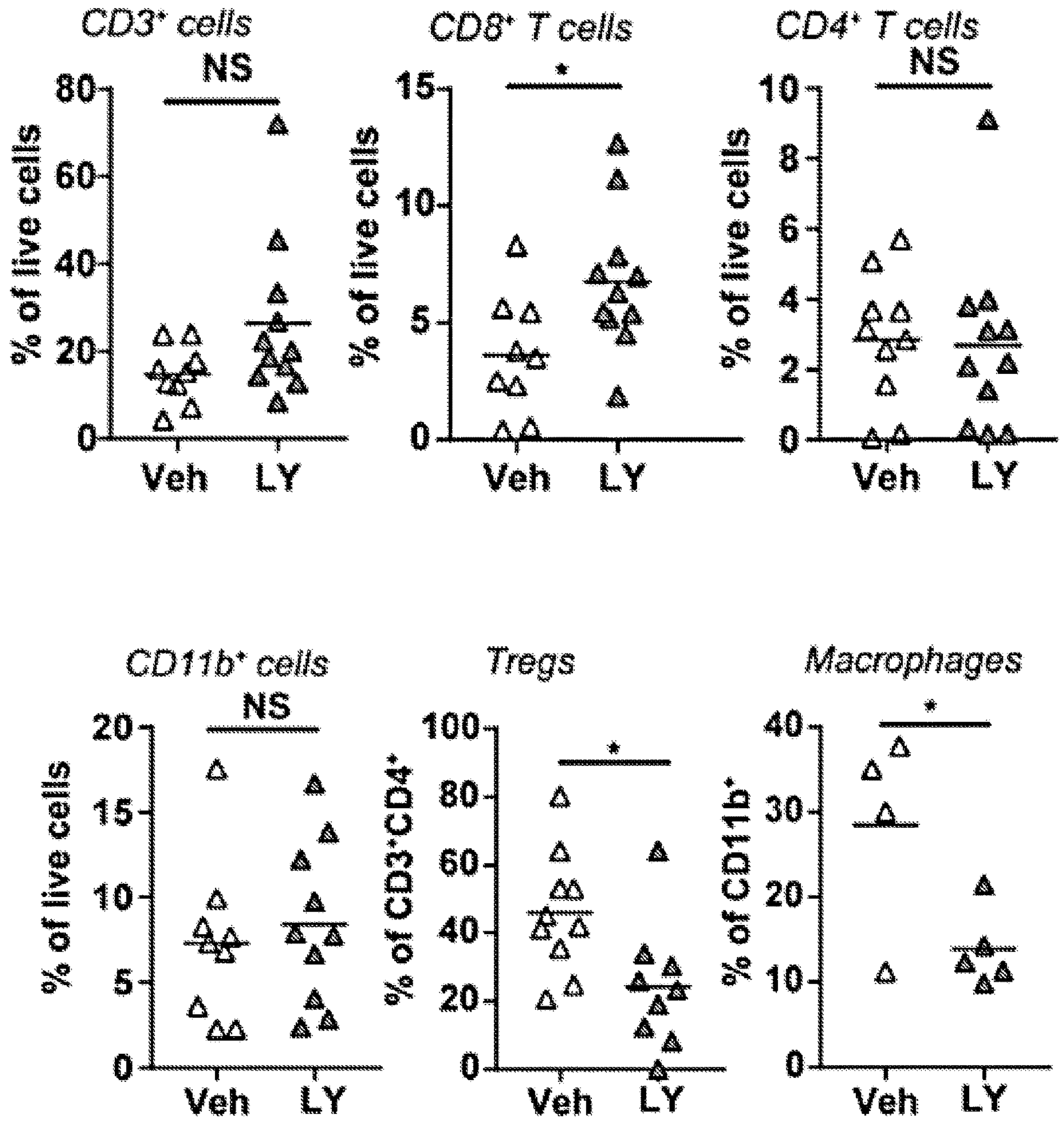
Figure 8F:
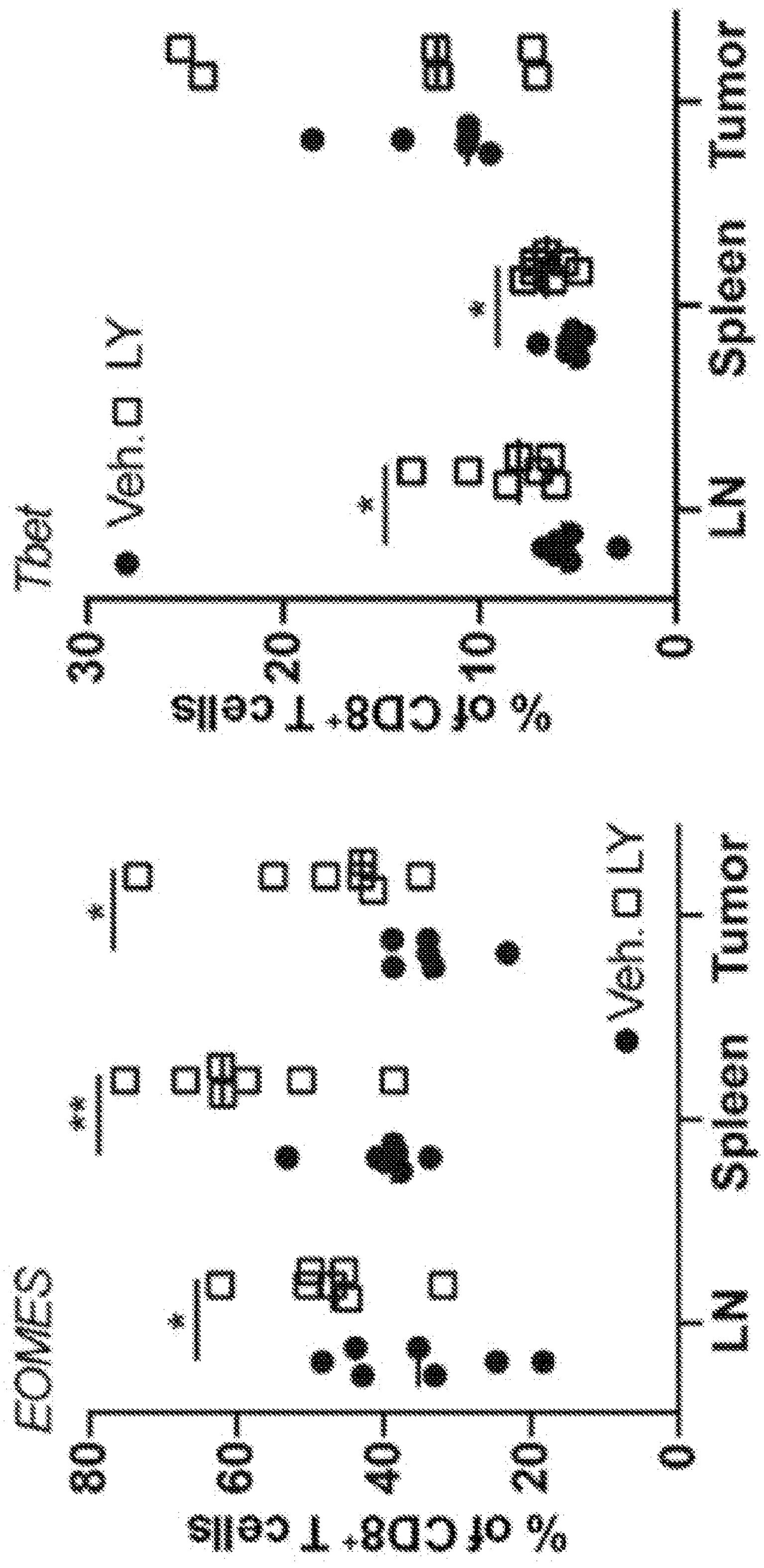

LY2157299, which inhibits TGFβ signaling, altered CD8 T cell function and tumor infiltrating immune cells similar to what was observed in tumors from ALK5$^{\Delta CD8}$ animals. There were more CD8$^+$ T cells and fewer macrophages and Tregs infiltrating tumors from LY-treated animals (FIG. 8E), consistent with changes observed in ALK5$^{\Delta CD8}$ animals. There was also an increase in the percentage of CD8$^+$ T cells expressing T-Box transcription factors EOMES and Tbet from spleens, lymph nodes and CT26 tumors of LY-treated mice consistent with enhanced $CD8^+$ T cell effector differentiation (FIG. 8F). tSNE plots generated from flow cytometric data from LY versus vehicle control treated animals demonstrated no novel cell populations in the tumor, draining lymph node, or spleen following ALK5 inhibition, but showed an enrichment of the tumor-infiltrating effector population (data not shown), consistent with that observed in the $ALK5^{\Delta CD8}$ animals (FIG. 8D). Together these data suggest that ALK5 inhibition with LY2157299 is capable of generating an increase in tumor-infiltrating effector $CD8^+$ T cells.

Example 5

Figure 9A:
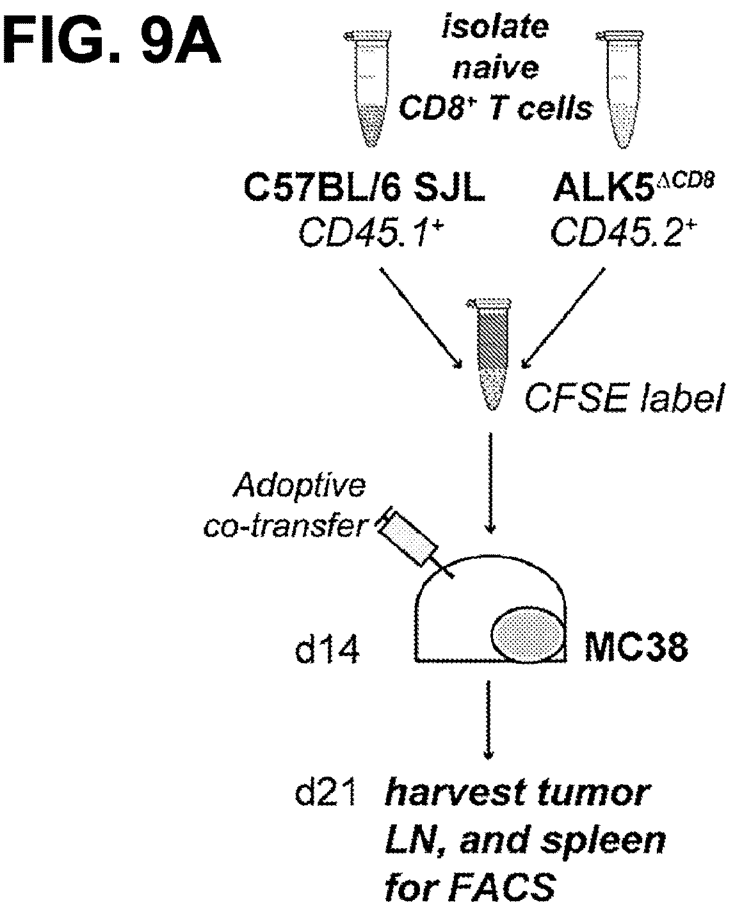
FIGS. 9A-9H show $ALK5^{\Delta CD8}$T cells upregulate CXCR3 and preferentially migrate to the tumor.
Figure 9B:
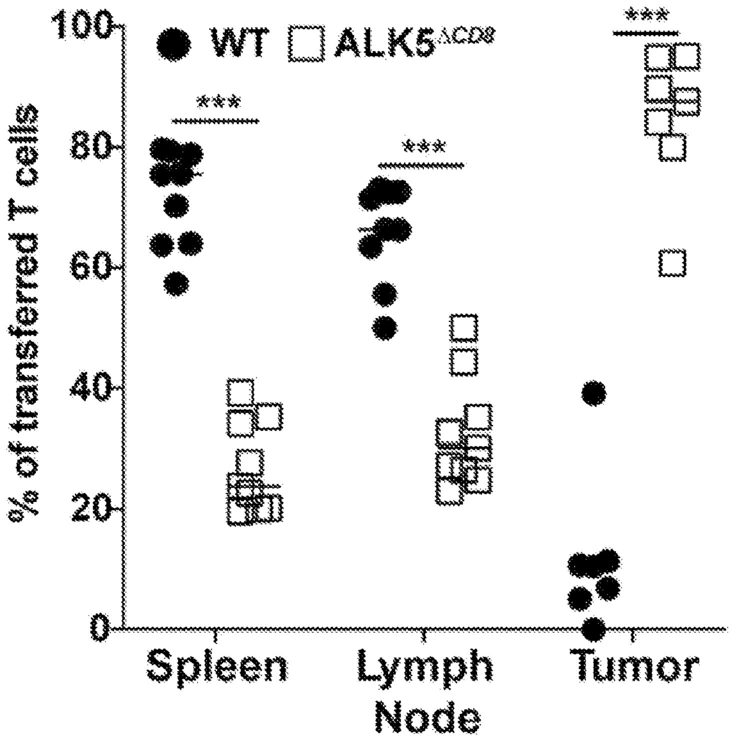
Figure 9C:
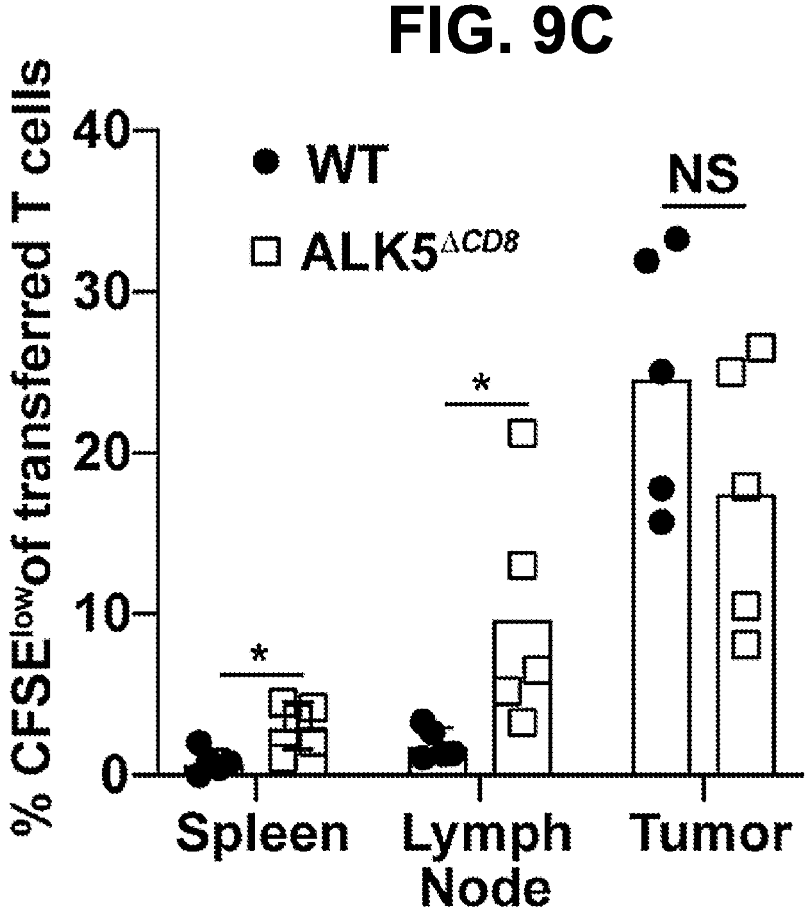
Figure 9D:
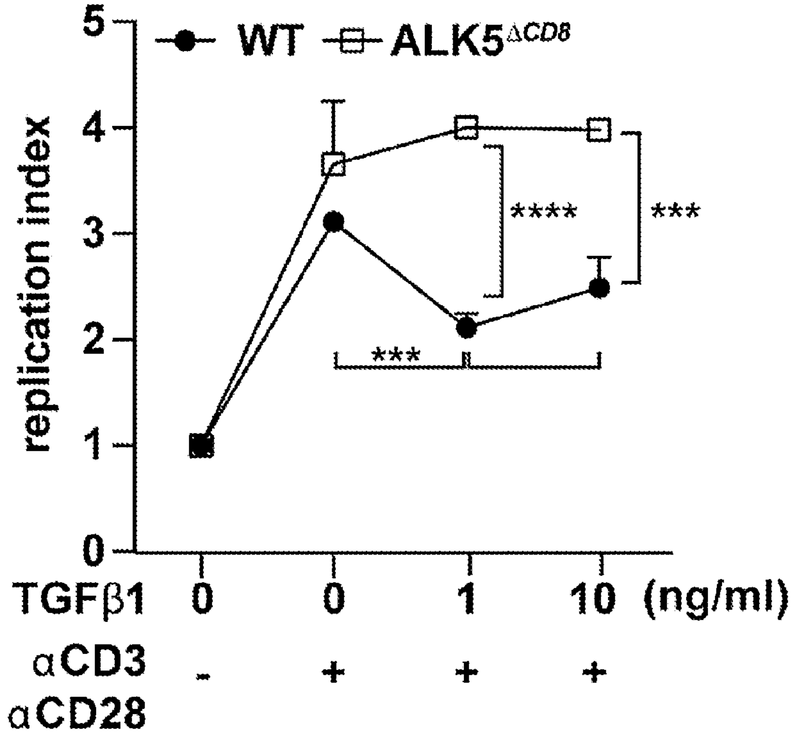
Figure 10A:
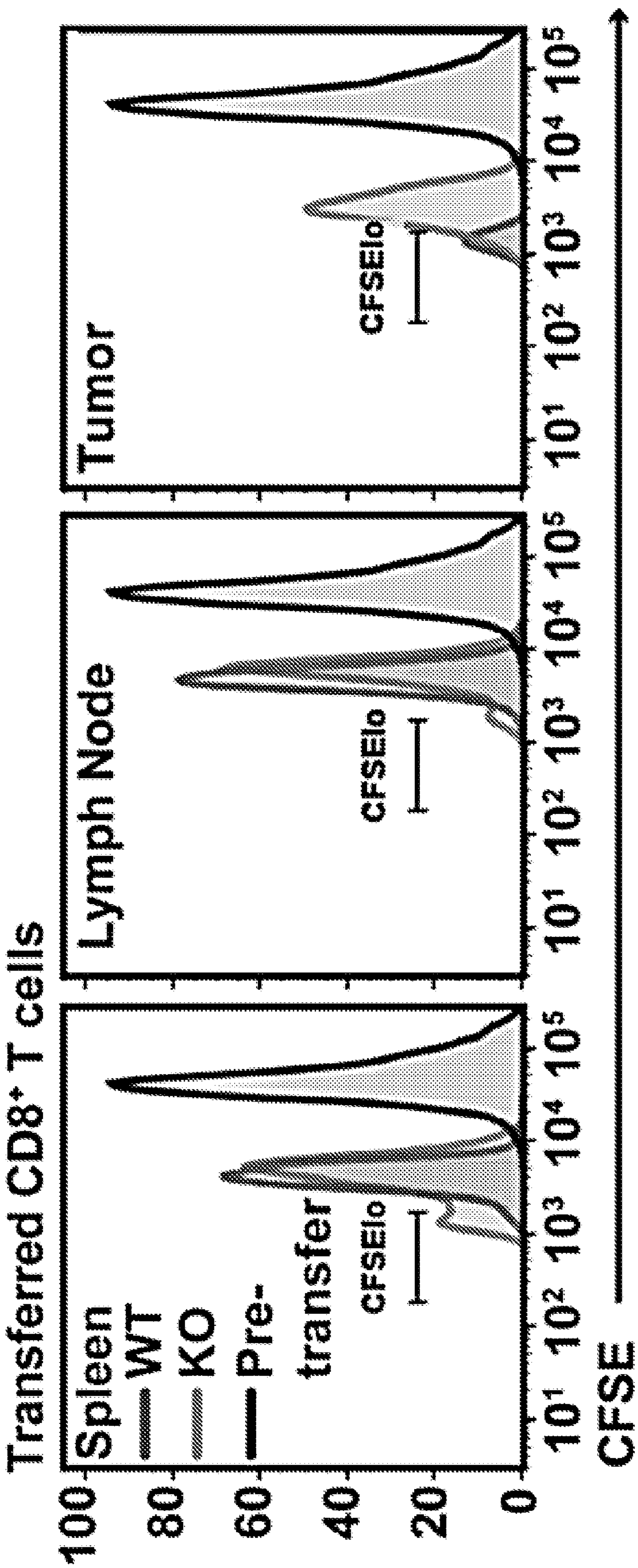
FIGS. 10A-10E show $CD8^+$ T cell proliferation is suppressed by the tumor microenvironment, but TGF13 inhibition can increase tumor trafficking.
Figure 10B:
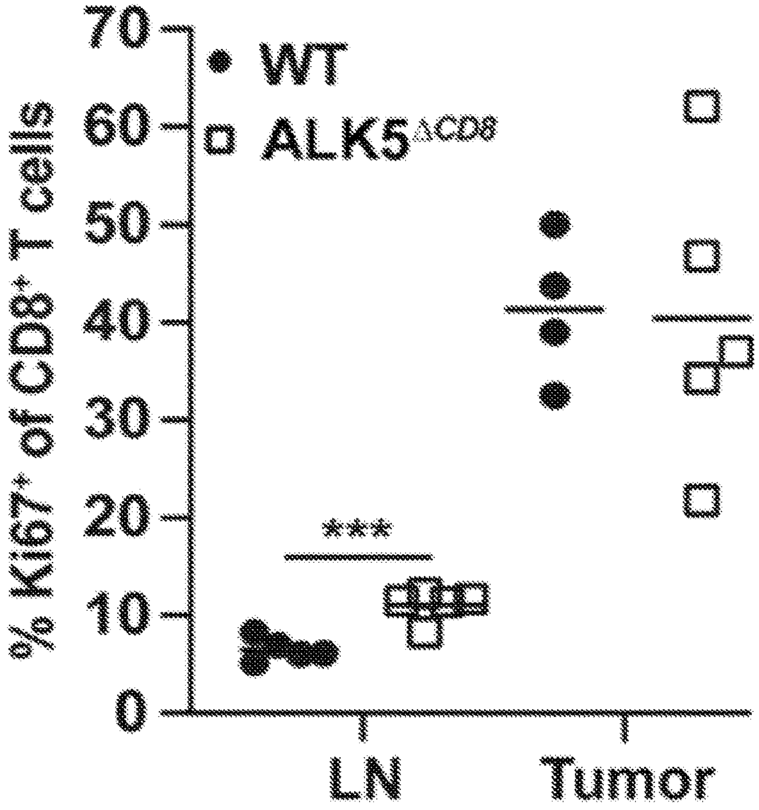

TGFβ Inhibits Tumor Infiltration by $CD8^+$ T Cells Via Suppression of CXCR3 Expression Based on the detection of increased tumor-infiltrating $CD8^+$ T cells in $ALK5^{\Delta CD8}$ and LY-treated mice, it was hypothesized that TGFβ may inhibit either in situ proliferation or tumor trafficking of $CD8^+$ T cells, or both. To evaluate these possibilities simultaneously, we adoptively co-transferred CFSE-labeled congenic WT and $ALK5^{\Delta CD8}$ $CD8^+$ T cells, at a 50:50 ratio, into WT mice with established day 14 MC38 tumors. Seven days following transfer, spleens, tumor draining lymph nodes, and tumors were harvested for flow cytometric analysis (FIG. 9A). A significantly higher percentage of WT cells could be detected in the spleen and lymph nodes, with a significantly greater proportion of $ALK5^{\Delta CD8}$ T cells in tumors (FIG. 9B). To determine whether the increased infiltration of $ALK5^{\Delta CD8}$ T cells into tumors was due to a proliferative advantage, CFSE reduction was assessed in the infiltrating cells. There was no significant difference in CFSE labeling between tumor-infiltrating WT versus $ALK5^{\Delta CD8}$ $CD8^+$ T cells, though increased proliferation of $ALK5^{\Delta CD8}$ $CD8^+$ T cells was observed in the spleen and lymph node (FIG. 9C and FIG. 10A). Consistent with these findings, the percentage of $Ki67^+CD8^+$ T cells was increased in the draining lymph nodes of $ALK5^{\Delta CD8}$ mice (FIG. 10B). As TGFβ has a known role in suppressing proliferation, we tested whether $ALK5^{\Delta CD8}$ $CD8^+$ T cells had a proliferative advantage ex vivo. Naïve splenocytes were cultured in vitro with TGFβ1 with and without CD3/CD28 stimulation and evaluated for proliferation. TGFβ-mediated suppression of proliferation was observed in WT $CD8^+$ T cells, but not in the $ALK5^{\Delta CD8}$ $CD8^+$ T cells (FIG. 9D). Taken together, these data suggest: a) proliferation may be suppressed by means other than TGFβ in the tumor microenvironment, and b) improved tumor trafficking was responsible for the increased $CD8^+$ T cell infiltration.

Figure 9E:
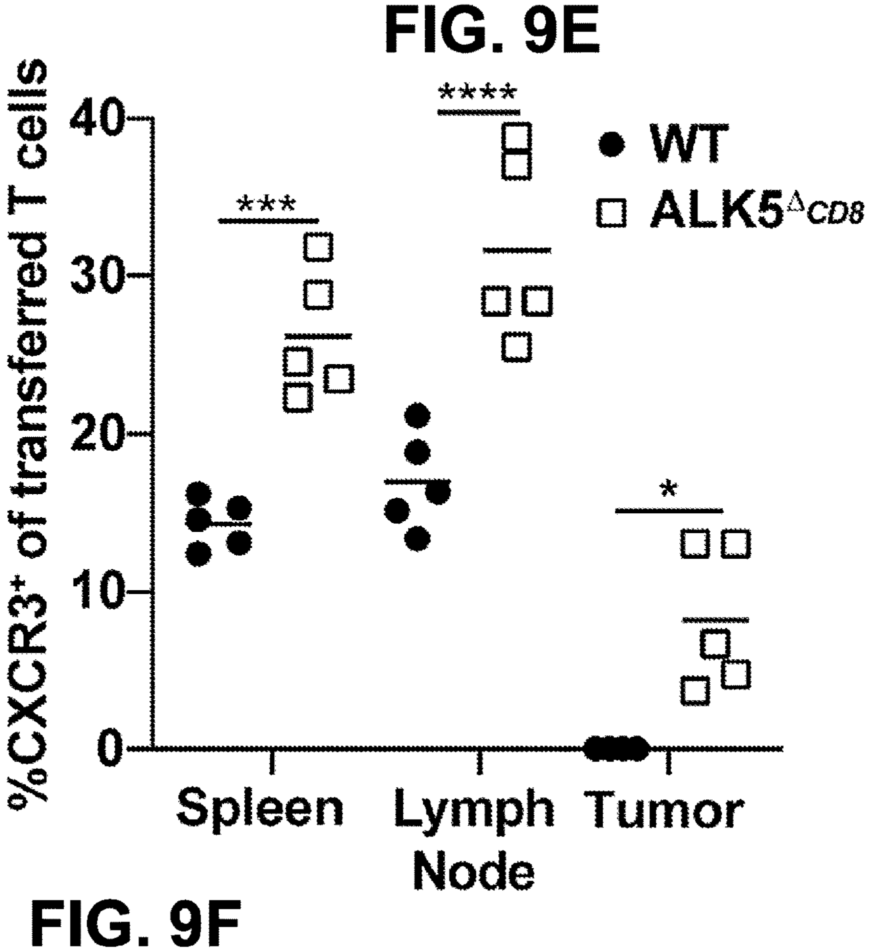
Figure 9F:
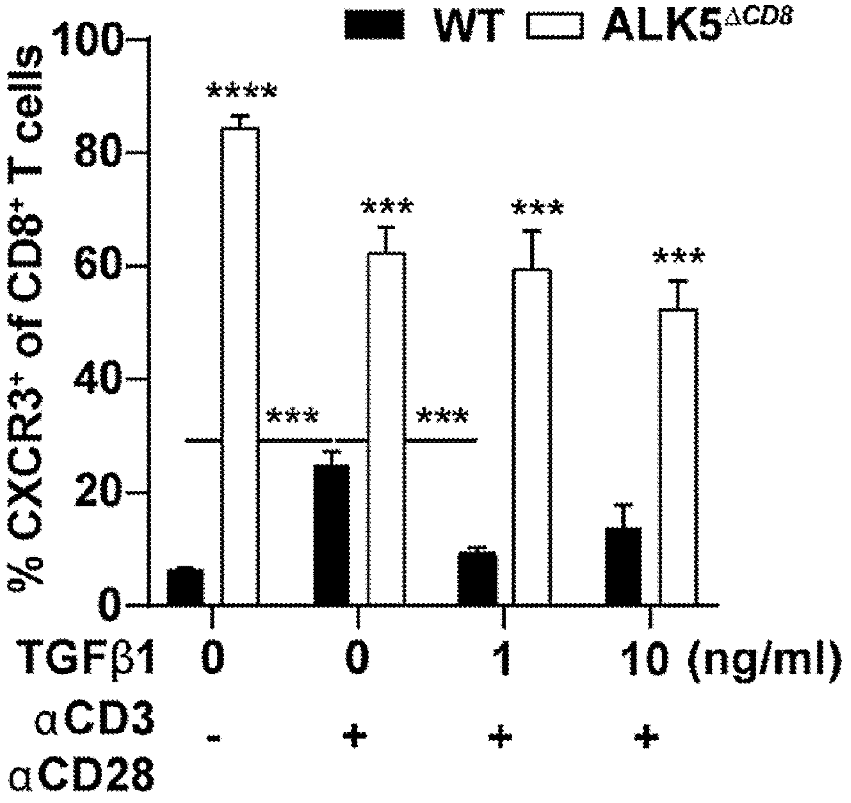
Figure 9G:
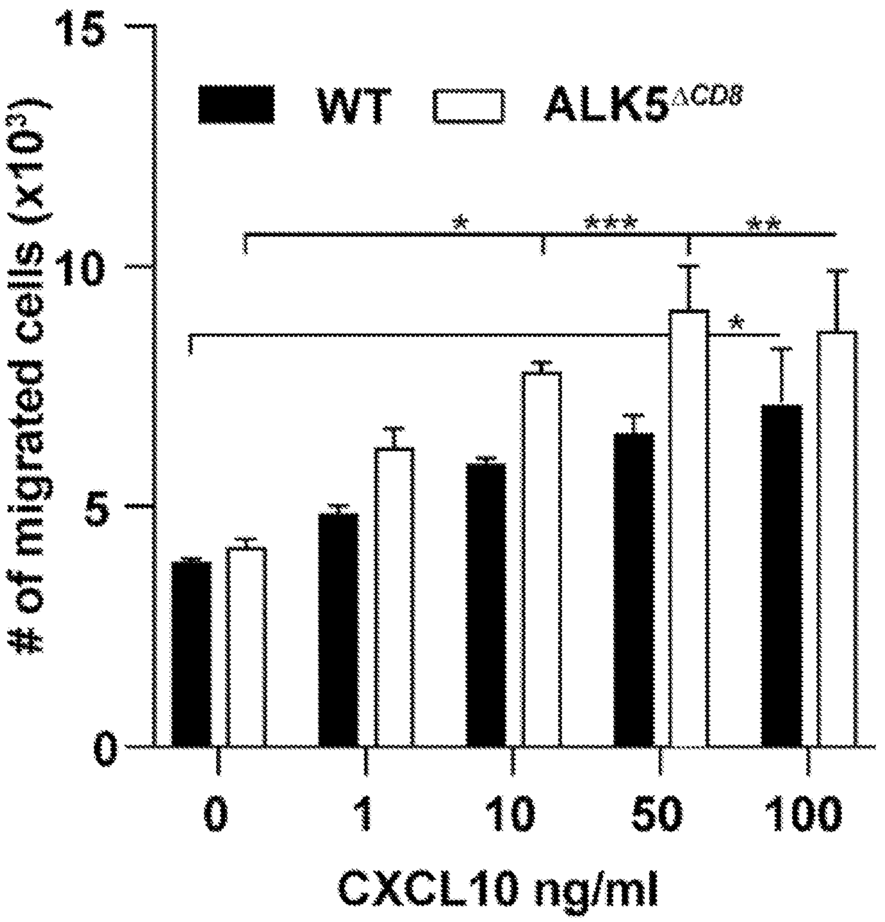
Figure 10C:
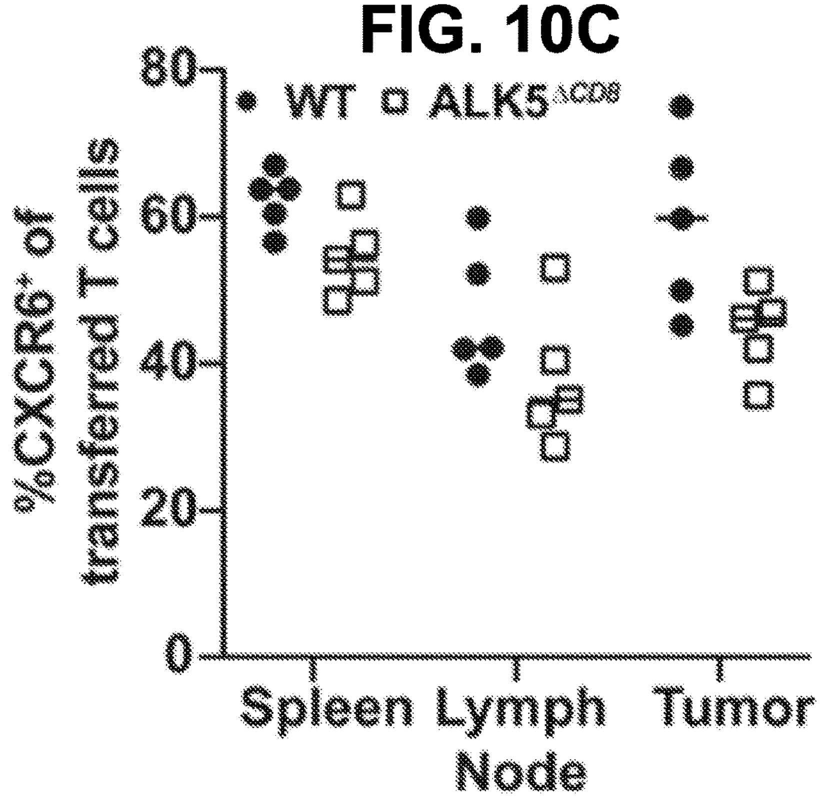
Figure 10D:
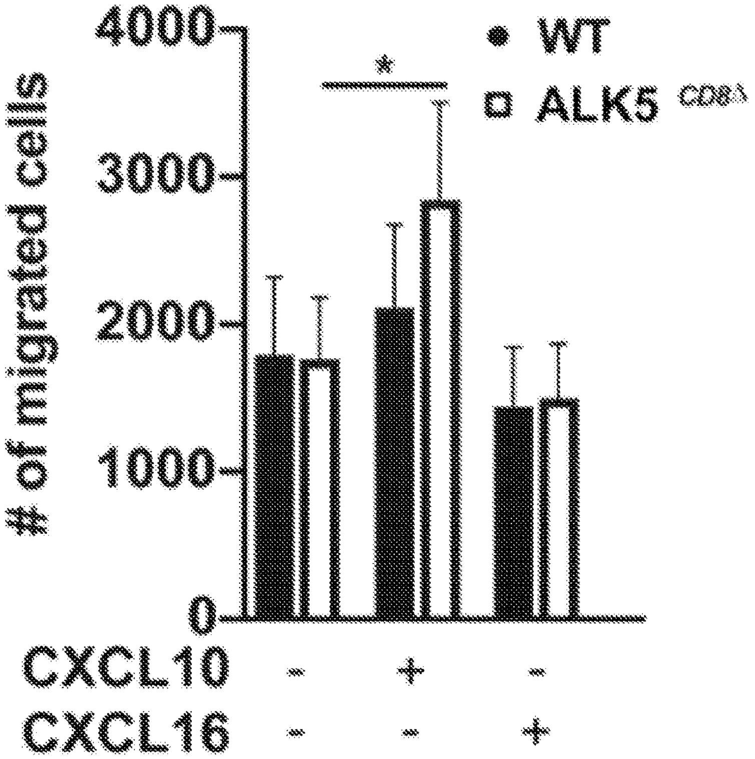

Therefore, mechanisms of increased tumor trafficking that could be attributed to changes in the $CD8^+$ T cells harboring ALK5 deletion were evaluated. Given the enhanced cytotoxicity of $ALK5^{\Delta CD8}$ $CD8^+$ T cells and diminished macrophage infiltrate into tumors, differences in cytokines and chemokines from digested tumors grown in WT and $ALK5^{\Delta CD8}$ animals was assessed by multiplex cytokine bead array. Minimal differences in tumor cytokines were observed (data not shown). To determine whether the expression of chemokine receptors on CD8 T cells could explain the differential infiltration of WT and $ALK5^{\Delta CD8}$ T cells, expression of CXCR3 and CXCR6 were evaluated, which are dominant chemokine receptors for $CD8^+$ T cell trafficking into tumors (Vignali & Kallikourdis, *Cytokine Growth Factor Rev.* 36:107-116, 2017), particularly following radiation (Matsumura et al., *J. Immunol.* 181:3099-3107, 2008; Marciscano et al., *Clin. Cancer Res.* 24:5058-5071, 2018). An increase in CXCR3 expression in transferred $ALK5^{\Delta CD8}$ $CD8^+$ T cells in the co-transfer assay (FIG. 9E), but not CXCR6 (FIG. 10C) was observed. Whether CXCR3 expression was altered by TGFβ treatment ex vivo was then tested. Splenocyte-derived $CD8^+$ T cells from WT animals demonstrated an increase in CXCR3 expression with CD3/CD28 stimulation, which was inhibited by TGFβ1 (FIG. 4F). However, $CD8^+$ T cells from $ALK5^{\Delta CD8}$ animals demonstrated a very high baseline expression of CXCR3, which was minimally decreased by αCD3/CD28 stimulation, while TGFβ1 treatment had no effect (FIG. 4F). Consistent with increased CXCR3 expression, an increase in $ALK5^{\Delta CD8}$ $CD8^+$ T cell in vitro migration towards CXCR3 ligand CXCL10 was observed compared to WT (FIG. 9G and FIG. 10D), but migration towards CXCR6 ligand CXCL16 was not observed in either WT or $ALK5^{\Delta CD8+}$ T cells (FIG. 10D). In the MC38 tumor model utilized, CXCL10 protein levels were equivalent between tumors implanted in $ALK5^{\Delta CD8}$ and WT animals at day 14 (data not shown). Thus, the enhanced $CD8^+$ T cell trafficking appears to be result of the modulation of CXCR3 expression on $CD8^+$ T cells.

Figure 9H:
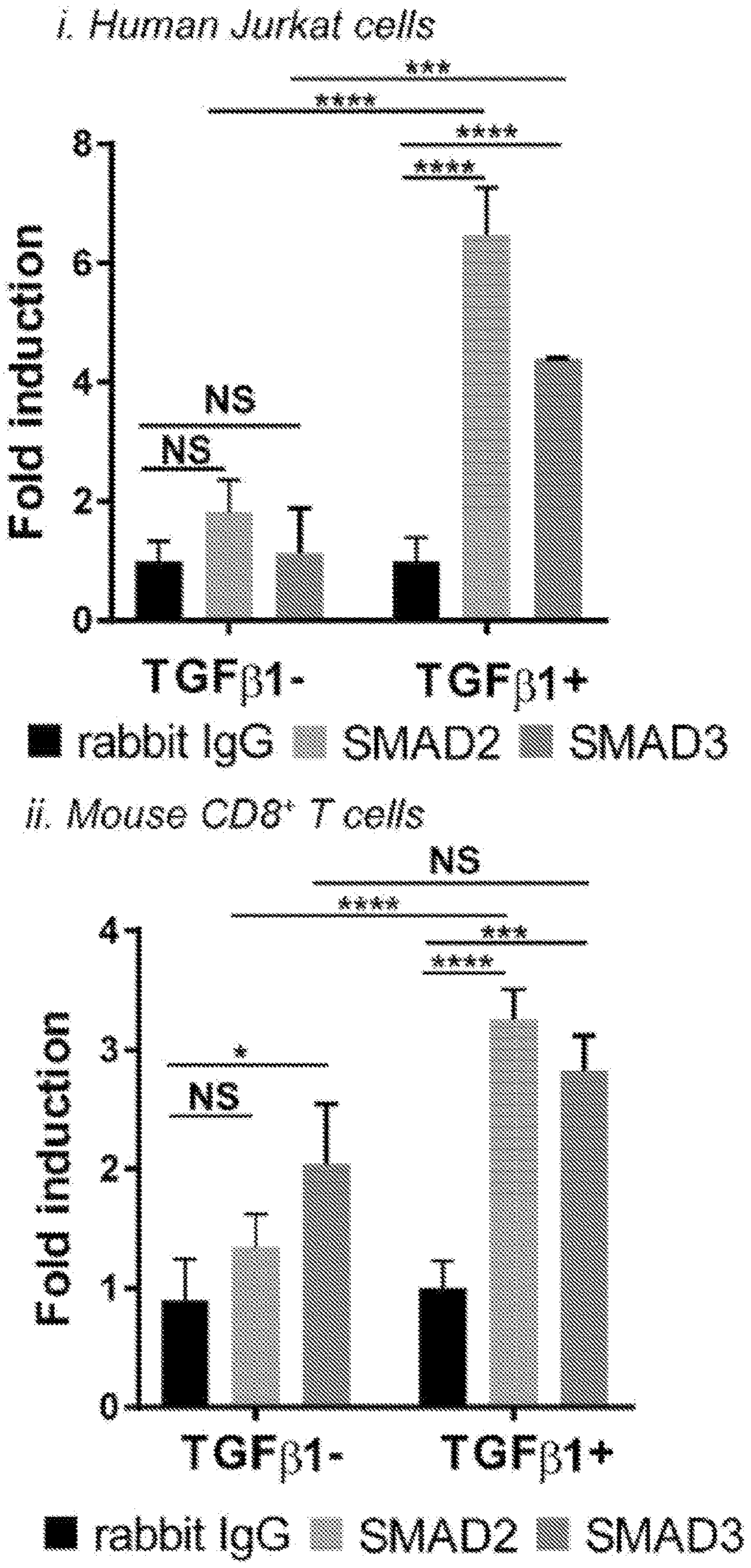

In order to assess whether CXCR3 was a direct transcriptional target of TGFβ in T cells, chromatin immunoprecipitation for the TGFβ signaling mediators Smad2 and Smad3, and qPCR of the CXCR3 promoter region identified to contain Smad-binding elements, up to 5000 bp upstream of the transcriptional start site were performed. The human CXCR3 promoter in the human Jurkat cell line exhibited a significant increase in Smad2 and Smad3 binding approximately 4000 bp upstream of the transcriptional start site, 1.5 hours after TGFβ treatment (FIG. 9H(i)). Similarly, increased Smad2 binding the murine CXCR3 promoter approximately 3800 bp upstream of the TSS in splenocyte-derived purified $CD8^+$ T cells following TGFβ stimulation (FIG. 9H(ii)) was observed, while Smad3 bound the promoter constitutively and did not increase with TGFβ stimulation (FIG. 9H(ii)). These data suggest that CXCR3 is transcriptionally suppressed by TGFβ, leading to decreased CXCR3 expression on $CD8^+$ T cells and impaired chemotaxis to its ligands.

To test whether enhanced CXCR3 expression is necessary for the rejection of MC38 tumors and extended survival observed in tumor-bearing $ALK5^{\Delta CD8}$ mice, CXCR3 was blocked in vivo with an anti-CXCR3 blocking antibody delivered on days 4, 8, and 12 after tumor challenge (FIG. 11A-B). The majority of $ALK5^{\Delta CD8}$ mice rejected MC38 tumors, whereas all tumors progressed in WT animals (FIG. 11A). However, anti-CXCR3 interfered with the anti-tumor activity, with 67% of $ALK5^{\Delta CD8}$ mice treated with αCXCR3 antibody developing tumors (FIG. 11A). Consistent with this, tumor infiltration by $CD8^+$ T cells was significantly reduced by administration of αCXCR3 antibody (FIG. 11B). The tumors that developed in the $ALK5^{\Delta CD8}$ mice grew with delayed growth kinetics, likely attributed to the enhanced effector function of $ALK5^{\Delta CD8}CD8^+$ T cells that infiltrating the tumors, albeit at lower frequencies due to CXCR3 blockade.

Figure 10E:
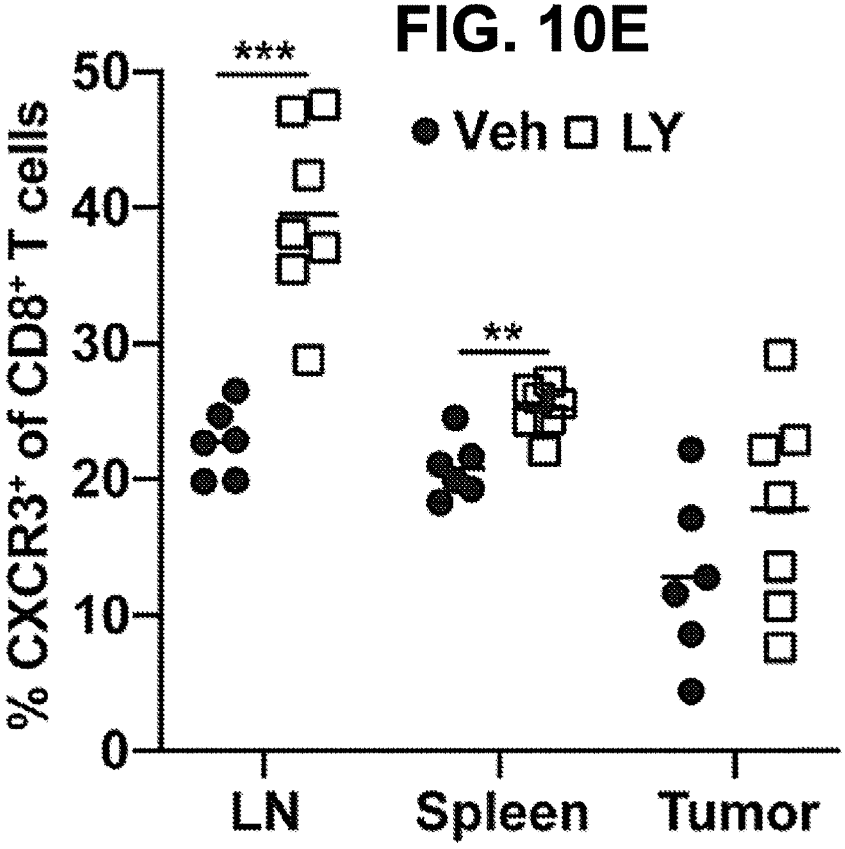

Whether CXCR3-dependent chemotaxis could be increased by utilizing an ALK5 inhibitor was then tested. In preclinical modeling, an increase in $CXCR3^+CD8^+$ T cells following treatment with LY2157299 was observed (FIG. 10E), indicating increased CXCR3 expression was not a developmental artifact of $ALK5^{\Delta CD8}$ transgenic mice. Of note, the frequency of tumor-infiltrating $CXCR3^+CD8^+$ T cells steadily decreased over time, with complete loss of $CXCR3^+$ cells 21 days post implantation in CT26 and 14 days post-implantation in MC38 (FIG. 10E and data not shown), which may reflect the development of an exhausted phenotype where CXCR3 is known to be downregulated (Subramaniam et al., *Immunity* 27:670-684, 2007). These data demonstrate that inhibition of TGFβ with a small molecule inhibitor can increase CXCR3 expression.

Example 6

TGFβ Inhibition Increases $CXCR3^+CD8^+$ T Cell Infiltration into Human Rectal Cancers and is Associated with Neoadjuvant Treatment Response To determine the clinical relevance of our data, the expression of CXCR3 in human patients was interrogated. Analysis of the TCGA colorectal database revealed an inverse correlation between SMAD2 and CXCR3 expression (FIG. 12A), consistent with the data implicating TGFβ as a suppressor of CXCR3 expression. An ongoing clinical trial of LY2157299 prior to standard of care chemoradiation in locally advanced rectal cancer allowed assessment of CXCR3 expression (NCT02688712, FIG. 12B). Enrolled patients undergo peripheral blood immune monitoring at baseline and at day 15, after two weeks of treatment with LY2157299 (FIG. 12B). For this study five standard panels were run, which assess for T effector and memory, $CD4^+$ T cell, dendritic cell, natural killer cell, and B cell populations. The only panel that includes CXCR3 is the $CD4^+$ panel, which also includes CD45, CD3, CD4, CD25, CD127, CCR4, CCR5, CCR6, CD45RO, HLA-DR, CD38, ICOS, PD-1, GITR, NKG2D, CD69, CD27, BTLA4, Perforin, Granzyme B, and Ki67. The T effector and memory panel, which includes CD8, does not include CXCR3. Therefore, the $CD4^+$ T cell panel was used and back gated on $CD45^+CD3^+CD4^-$ T cells, the majority of which are $CD8^+$ T cells (on average 65% of $CD45^+CD3^+CD4^-$ cells were $CD8^+$ T cells using the T effector and memory panel which has CD45, CD3, CD4, and CD8, but not CXCR3), and calculated CXCR3 expression. The frequency of $CXCR3^+CD45^+CD3^+CD4^-$ T cells and the CXCR3 MFI in the peripheral blood changed from day 0 to day 15, following LY2157299 administration, in patients (FIG. 12B-C, and data not shown). The majority of patients on study had a decrease in peripheral blood CXCR3 expression (FIG. 12C). All patients enrolled on study were clinically node positive by MRI and/or EUS evaluation prior to starting therapy. Interestingly, patients rendered pathologically node negative after neoadjuvant therapy demonstrated a reduction in peripheral blood $CXCR3^+$ cells (FIG. 12C) and MFI ($p<0.05$, data not shown). Additionally, the percent change in $CXCR3^+$ cells significantly correlated with pathologic treatment response, as measured by the neoadjuvant rectal (NAR) score (FIG. 12C), a validated surrogate for overall survival (George et al., *Curr. Colorectal Cancer Rep.* 11:275-280, 2015). We hypothesized this was due to $CXCR3^+CD8^+$ T cells migrating to the tumor tissue. Therefore, forceps-biopsy specimens obtained by proctoscopy at baseline and day 15 were evaluated for alterations in $CXCR3^+CD8^+$ T cells. There was an increase in the percentage $CXCR3^+CD8^+$ T cells in the tumor microenvironment after LY2157299 treatment (FIG. 12D-E). Taken together, these data demonstrate a novel mechanism by which the response to cytotoxic therapy can be improved: TGFβ acts locally to suppress the transcription of CXCR3 thereby limiting tumor-infiltration; $CD8^+$ T cells that do reach the tumor have an increased threshold for activation, decreased cytotoxicity, and decreased proliferation. These data demonstrate that TGFβ inhibition is capable of altering chemokine receptor expression on T cells to promote chemotaxis to the tumor, and improve response to neoadjuvant therapy.

Example 7

Checkpoint Inhibition Decreases Peripheral Blood $CXCR3^+$ T Cells in Head and Neck Squamous Cell Carcinoma Patients The effect of checkpoint inhibition on CXCR3+ T cells was assessed using the treatment schema shown in FIG. 13A. Patients with locoregionally advanced HNSCC were treated with anti-PD-1 (nivolumab, 240 mg, IV) three times Q2W. Radiation was administered following the first anti-PD-1 treatment, and surgery was performed at week 6 to assess pathologic status. Patients also received stereotactic body radiation therapy (SBRT) following the first dose of nivolumab. Peripheral blood was drawn at baseline and one week after administration of the first dose of nivolumab. CXCR3+ T cells were analyzed and the percentage change following nivolumab is shown in FIG. 13B. These data demonstrate a decrease in $CD3^+CD4^-CXCR3^+$ T cells following neoadjuvant nivolumab correlated with clearance of nodal disease, while stable to increased $CD3^+CD4^-CXCR3^+$ T cells was associated with persistent nodal disease. As HPV+ and HPV-HNSCC have marked differences in natural history and/or behavior, these cohorts were also analyzed separately (FIGS. 13C and 13D). When comparing response to neoadjuvant therapy in the HPV+ and HPV− cohorts separately, the change in percent $CXCR3^+CD3^+CD4^-$ T cells was more distinct.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of assessing or predicting response of a solid tumor to treatment with an inhibitor of transforming growth factor beta receptor type 1 (TGFβR1) signaling in a subject, comprising:

measuring an amount of C-X-C motif chemokine receptor 3 (CXCR3)-positive T cells in a peripheral blood sample from the subject following administration of at least one dose of the inhibitor to the subject;

measuring an amount of CXCR3-positive T cells in a peripheral blood sample from a control;

comparing the amounts in the samples, wherein the amount is higher in the control sample;

predicting that the cancer will respond to the inhibitor; and subsequently administering at least one dose of galunisertib, LY3200882, GW788388, LY2109761, SB431542, SB525334, AZ12601011, or AZ12799734 to the subject, thereby treating the subject.

2. The method of claim 1, wherein the peripheral blood sample comprises whole blood, plasma, serum, or peripheral blood mononuclear cells.

3. The method of claim 1, wherein the inhibitor of TGFβR1 signaling is galunisertib, LY3200882, GW788388, LY2109761, SB431542, SB525334, AZ12601011, or AZ12799734.

4. The method of claim 1, wherein the inhibitor of TGFβR1 signaling is galunisertib or LY3200882, and the final administration step comprises administering at least one dose of galunisertib or LY3200882.

5. The method of claim 1, wherein the solid tumor is a colorectal tumor, lung tumor, head and neck squamous cell carcinoma, renal cell carcinoma, or melanoma.

6. The method of claim 1, wherein measuring the amount of CXCR3-positive T cells comprises using flow cytometry.

7. The method of claim 1, wherein the control comprises an amount of CXCR3-positive T cells in a peripheral blood sample obtained from the subject prior to initial treatment with the inhibitor of TGFβR1 signaling.

8. A method of assessing or predicting a response of a solid tumor to treatment with an inhibitor of transforming growth factor beta receptor type 1 (TGFβR1) signaling in a subject, comprising:

measuring an amount of C-X-C motif chemokine receptor 3 (CXCR3)-positive T cells in a solid tumor sample from the subject following administration of at least one dose of the inhibitor to the subject;

measuring an amount of CXCR3-positive T cells in a solid tumor sample from a control;

comparing the amounts in the samples, wherein the amount is lower in the control sample;

predicting that the cancer will respond to the inhibitor; and subsequently administering at least one dose of galunisertib, LY3200882, GW788388, LY2109761, SB431542, SB525334, AZ12601011, or AZ12799734 to the subject, thereby treating the subject.

9. The method of claim 8, wherein the inhibitor of TGFβR1 signaling is galunisertib, LY3200882, GW788388, LY2109761, SB431542, SB525334, AZ12601011, or AZ12799734.

10. The method of claim 8, wherein the inhibitor of TGFβR1 signaling is galunisertib or LY3200882, and the method comprises administering the at least one dose of galunisertib or LY3200882.

11. The method of claim 8, wherein the solid tumor is a colorectal tumor, lung tumor, head and neck squamous cell carcinoma, renal cell carcinoma, or melanoma.

12. The method of claim 8, wherein measuring the amount of CXCR3-positive T cells comprises using flow cytometry.

13. The method of claim 8, wherein the control comprises an amount of CXCR3-positive T cells in a sample of the solid tumor obtained from the subject prior to treatment with the inhibitor of TGFβR1 signaling.

14. A method of assessing or predicting a response of a solid tumor to treatment with an inhibitor of transforming growth factor beta receptor type 1 (TGFβR1) signaling in a subject, comprising:

measuring an amount of C-X-C motif chemokine receptor 3 (CXCR3)-positive T cells in a peripheral blood sample from the subject following administration of at least one dose of the inhibitor to the subject;

measuring an amount of CXCR3-positive T cells in a peripheral blood sample from a control;

comparing the amounts in the samples, wherein the amount is lower in the control sample;

predicting that the cancer will not respond to the inhibitor; and subsequently administering a chemotherapy or radiation treatment to the subject, thereby treating the subject.

15. The method of claim 14, comprising administering the chemotherapy, wherein the chemotherapy comprises an anti-metabolite chemotherapy.

16. The method of claim 15, wherein the antimetabolite chemotherapy comprises one or more of 5-fluorouracil and capecitabine.

17. The method of claim 14, wherein:

(i) the peripheral blood sample comprises whole blood, plasma, serum, or peripheral blood mononuclear cells;

(ii) the inhibitor of TGFβR1 signaling is galunisertib or LY3200882;

(iii) the solid tumor is a colorectal tumor, lung tumor, head and neck squamous cell carcinoma, renal cell carcinoma, or melanoma; and/or (iv) the control comprises an amount of CXCR3-positive T cells in a peripheral blood sample obtained from the subject prior to treatment with the inhibitor of TGFβR1 signaling.

18. A method of assessing or predicting a response of a solid tumor to treatment with an inhibitor of transforming growth factor beta receptor type 1 (TGFβR1) signaling in a subject, comprising:

measuring an amount of C-X-C motif chemokine receptor 3 (CXCR3)-positive T cells in a solid tumor sample from the subject following administration of at least one dose of the inhibitor to the subject;

measuring an amount of CXCR3-positive T cells in a solid tumor sample from a control; comparing the amounts in the samples, wherein the amount is higher in the control sample;

predicting that the cancer will not respond to the inhibitor; and subsequently administering a chemotherapy or radiation treatment to the subject, thereby treating the subject.

19. The method of claim 18, comprising administering the chemotherapy, wherein the chemotherapy comprises an anti-metabolite chemotherapy.

20. The method of claim 19, wherein the antimetabolite chemotherapy comprises one or more of 5-fluorouracil and capecitabine.

21. The method of claim 18, wherein:

(i) the inhibitor of TGFβR1 signaling is galunisertib or LY3200882;

(ii) the solid tumor is a colorectal tumor, lung tumor, head and neck squamous cell carcinoma, renal cell carcinoma, or melanoma; and/or (iii) the control comprises an amount of CXCR3-positive T cells in a sample of the solid tumor obtained from the subject prior to treatment with the inhibitor of TGFβR1 signaling.

* * * * *

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide primer
```

-continued

```
<400> SEQUENCE: 1

aagctgggcc tgattctgtc                                                 20


<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 2

aagtctgtgg tgggcttctg                                                 20


<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 3

ggctcctcct gacaacagac                                                 20


<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 4

tgcccaggct gacttcatac                                                 20


<210> SEQ ID NO 5
<211> LENGTH: 8
<212> TYPE: PRT
<213> ORGANISM: Artificial Sequence
<220> FEATURE:
<223> OTHER INFORMATION: Ovalbumin peptide

<400> SEQUENCE: 5

Ser Ile Ile Asn Phe Glu Lys Leu
1               5
```